(12) United States Patent
Igarashi

(10) Patent No.: US 7,466,490 B2
(45) Date of Patent: Dec. 16, 2008

(54) OBJECTIVE OPTICAL SYSTEM FOR AN ENDOSCOPE

(75) Inventor: Tsutomu Igarashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 11/898,524

(22) Filed: Sep. 13, 2007

(65) Prior Publication Data
US 2008/0180809 A1 Jul. 31, 2008

(30) Foreign Application Priority Data
Oct. 23, 2006 (JP) .............................. 2006-287437

(51) Int. Cl.
*G02B 3/00* (2006.01)
(52) U.S. Cl. ...................... 359/651; 359/645; 359/661; 359/740; 359/781; 359/784
(58) Field of Classification Search ......... 359/643–645, 359/656–661, 740, 781, 784
See application file for complete search history.

(56) References Cited

U.S. PATENT DOCUMENTS

| | | | |
|---|---|---|---|
| 4,042,295 A | 8/1977 | Yamasita et al. | |
| 4,059,344 A | 11/1977 | Yamasita | |
| 4,403,837 A * | 9/1983 | Nakahashi | 359/770 |
| 4,764,001 A | 8/1988 | Yokota | |
| 5,087,989 A * | 2/1992 | Igarashi | 359/692 |
| 5,198,931 A * | 3/1993 | Igarashi | 359/660 |
| 6,252,723 B1 | 6/2001 | Nagaoka | |
| 6,327,101 B1 | 12/2001 | Miyano | |
| 6,433,937 B1 | 8/2002 | Konno | |
| 6,582,362 B2 | 6/2003 | Konno | |
| 6,943,966 B2 | 9/2005 | Konno | |
| 2001/0007511 A1* | 7/2001 | Minami et al. | 359/689 |
| 2007/0047103 A1* | 3/2007 | Fujisaki | 359/691 |

FOREIGN PATENT DOCUMENTS

JP 7-181377 7/1995

* cited by examiner

*Primary Examiner*—Evelyn A. Lester
(74) *Attorney, Agent, or Firm*—Arnold International; Jon W. Henry; Bruce Y. Arnold

(57) ABSTRACT

An objective optical system is disclosed that is suitable for a high-precision endoscope that performs focusing by moving a single lens component. The objective optical system includes, in order from the object side, a front lens group, a middle lens group, and a rear lens group. The middle lens group is composed of two or more lens components, at least two of which have positive refractive power, and the lens component that is moved for focusing is in the middle lens group. Additionally, the objective optical system satisfies two specified conditions, and other conditions may apply.

19 Claims, 41 Drawing Sheets

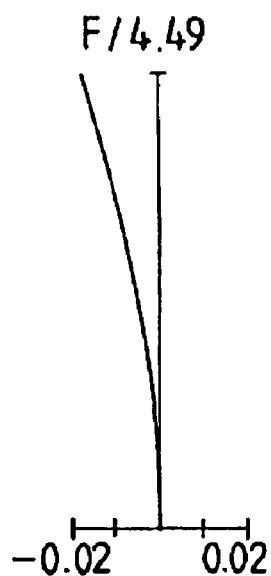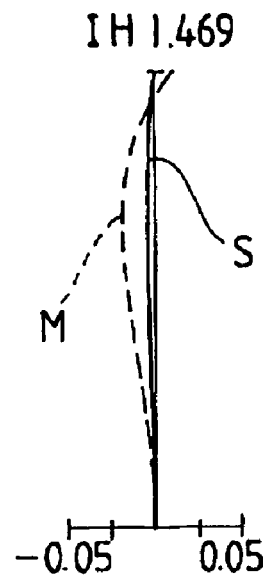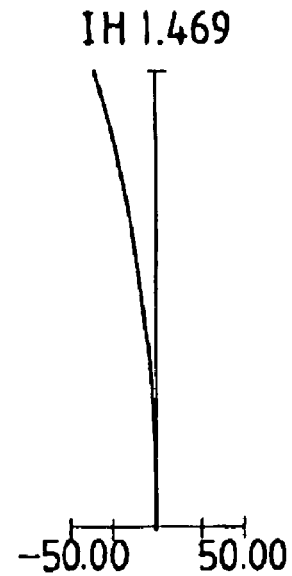
Fig. 36A　　　　　　Fig. 36B　　　　　　Fig. 36C
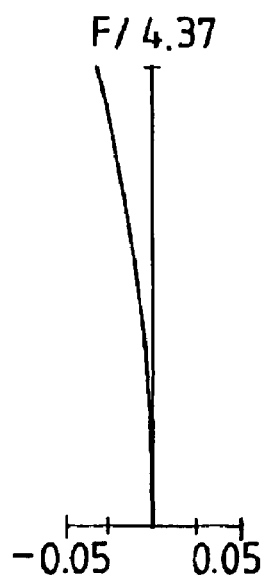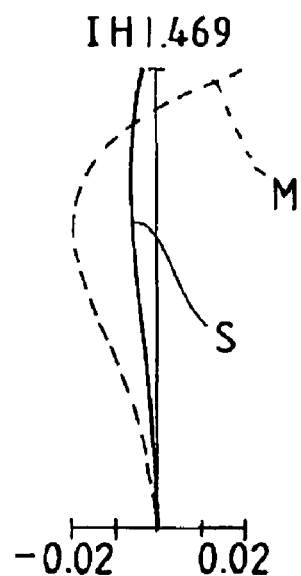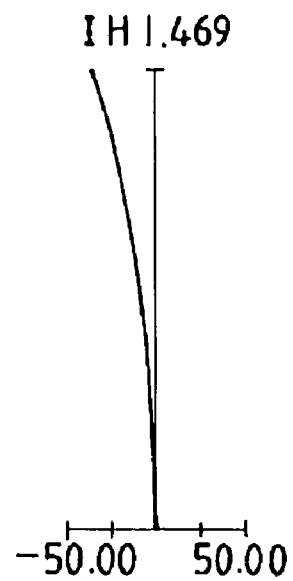
Fig. 36D　　　　　　Fig. 36E　　　　　　Fig. 36F

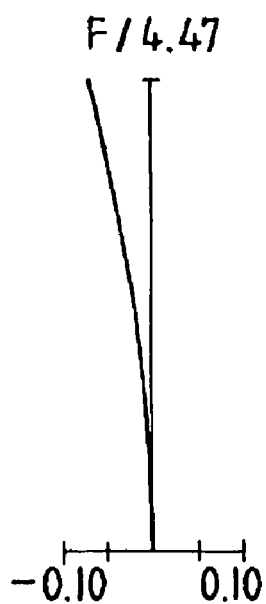
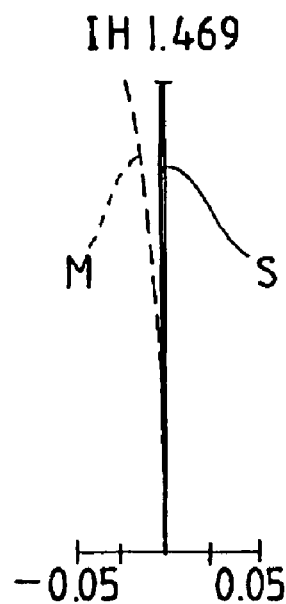
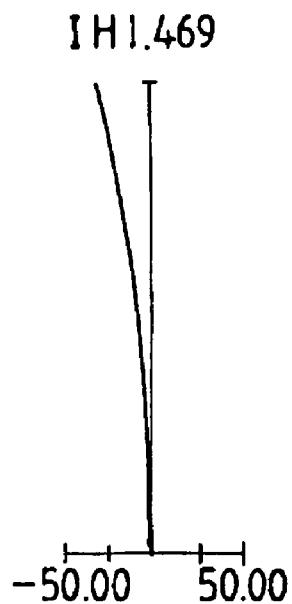
Fig. 42A	Fig. 42B	Fig. 42C
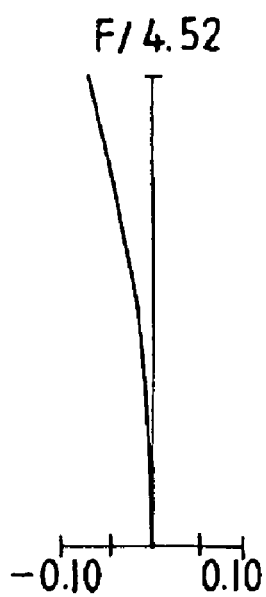
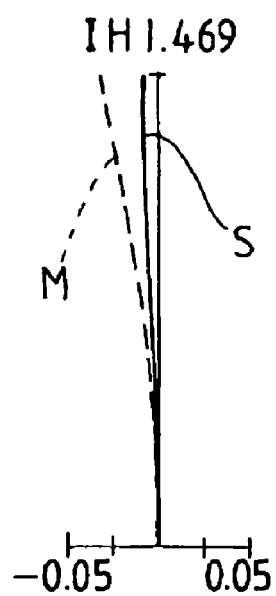
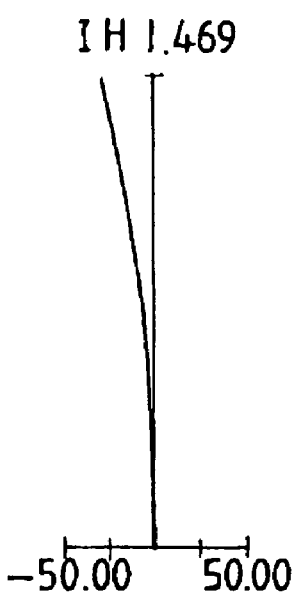
Fig. 42D	Fig. 42E	Fig. 42F

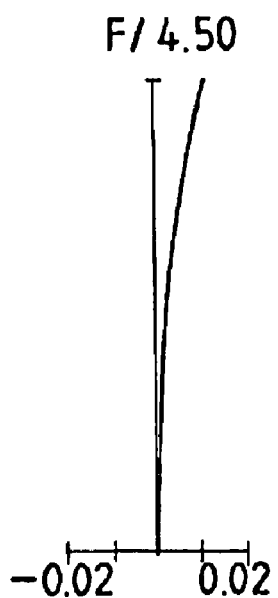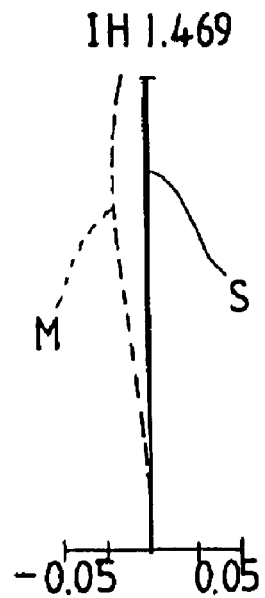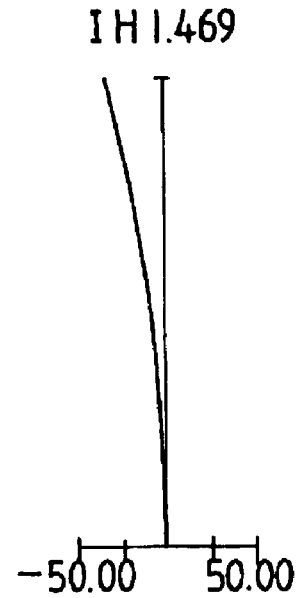
Fig. 45A Fig. 45B Fig. 45C
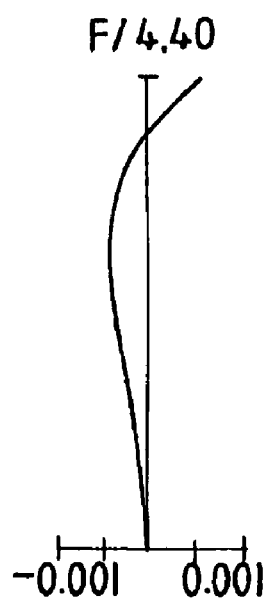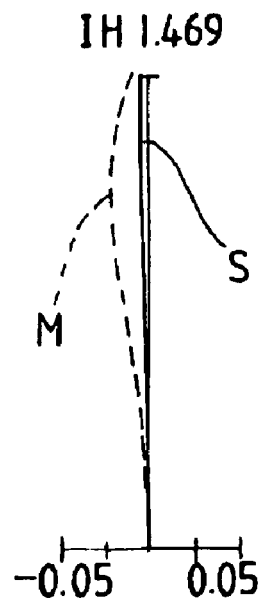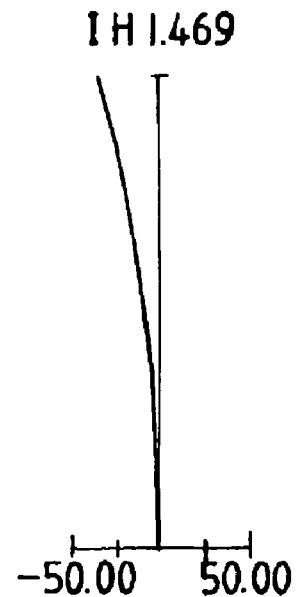
Fig. 45D Fig. 45E Fig. 45F

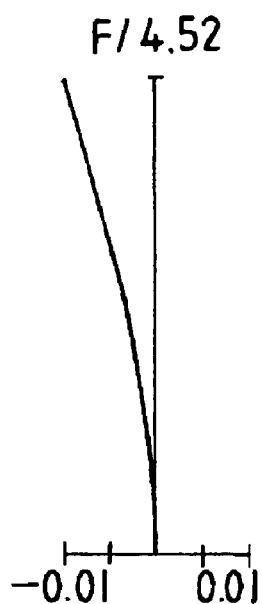 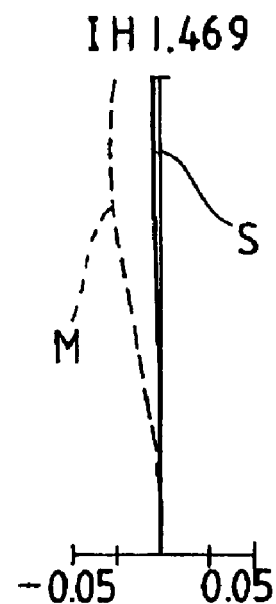 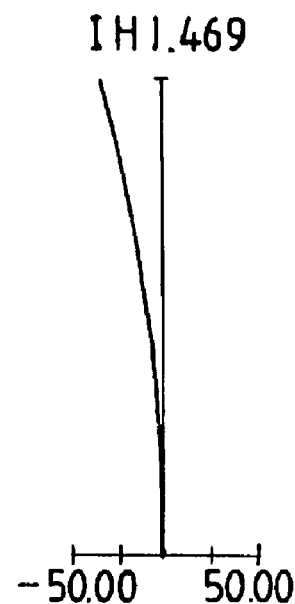
Fig. 47A  Fig. 47B  Fig. 47C
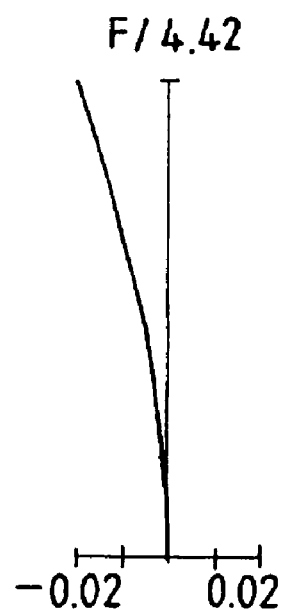 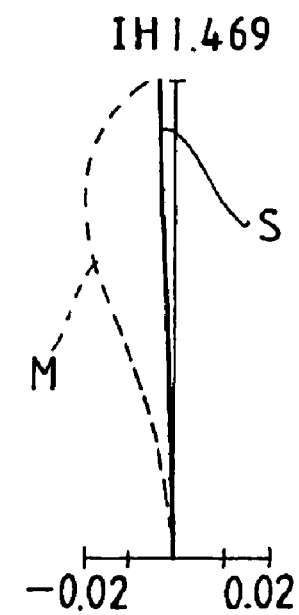 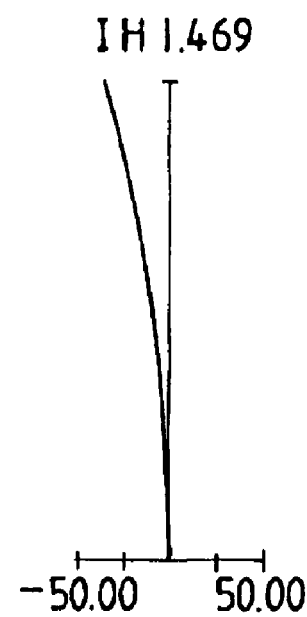
Fig. 47D  Fig. 47E  Fig. 47F

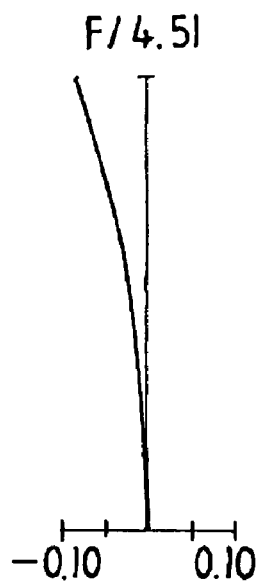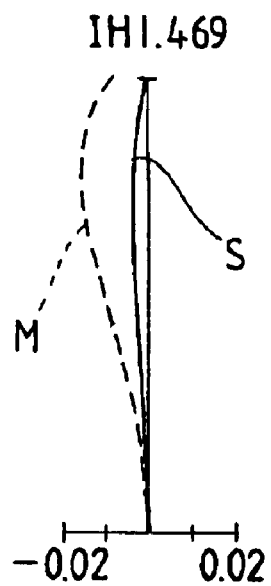
Fig. 51A  Fig. 51B  Fig. 51C
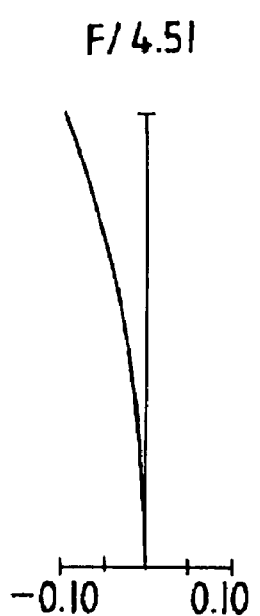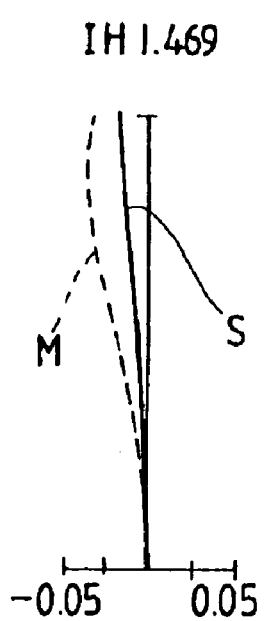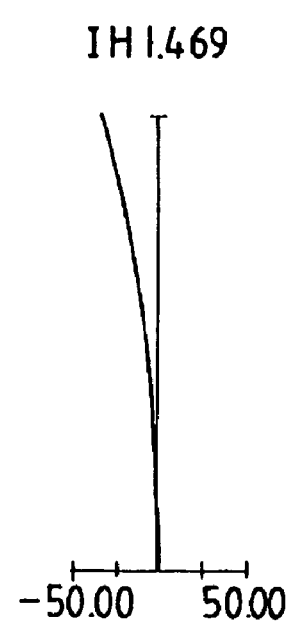
Fig. 51D  Fig. 51E  Fig. 51F

OBJECTIVE OPTICAL SYSTEM FOR AN ENDOSCOPE

This application claims benefit of foreign priority under 35 U.S.C. 119 of Japanese Patent Application No. 2006-287437 filed on Oct. 23, 2006, the contents of which are hereby incorporated by reference.

TECHNICAL FIELD OF THE INVENTION

The present invention relates to a high image quality objective optical system for an endoscope.

BACKGROUND OF THE INVENTION

In a so-called videoscope mounted with solid-state image pickup elements at the tip of the insertion portion of an endoscope, a system for outputting a high precision video signal of HDTV specification and/or PC format has been commercialized. It is easy to realize a videoscope of standard specifications with pan focus if it has NTSC/PAL resolution. However, it becomes difficult to obtain a proper balance of optical specifications with pan focus due to effects of lowering sensitivity caused by the reduction of pixels with solid-state image pickup elements and deterioration of contrast caused by diffraction and other factors. Additionally, optical specifications when adopting progressive read-out type, primary color, single-plate image pickup units or multi-plate image pickup units, such as two-plate or three-plate units, which provide a high precision image other than by increasing the number of pixels, are not established with pan focusing.

Therefore, in an objective optical system that provides high precision images, a decrease of f-number that is necessary to ensure a sufficient image brightness for viewing a high precision image results in an insufficient depth of field that must be compensated for by including a focusing function in the objective optical system.

The most general construction for providing the focusing function in an endoscope is a mount of the lens moving type. For a driving system in which lenses are moved by such a mount, a mount that can be arranged at the tip of the endoscope in the vicinity of a moving lens is desirable from the viewpoint of power transmission efficiency and positional accuracy.

Objective optical systems described in the following cited references have been known as prior art examples of objective optical systems for an endoscope having a focusing function by lens movement: Japanese Patent S55-15004; Japanese Patent H4-3851; Japanese Laid-Open Patent Application H7-181377; Japanese Patent S55-15005; Japanese Laid-Open Patent Application H11-316339; Japanese Laid-Open Patent Application 2000-267002; Japanese Laid-Open Patent Application 2000-330015; Japanese Laid-Open Patent Application 2002-28126; and Japanese Laid-Open Patent Application 2002-357773.

In order to apply the optical systems described in these patent references to an endoscope with a focusing function having high-precision solid-state image pickup elements, various problems must be addressed that will be discussed in the following comments.

However, first, definitions of the terms "lens element" and "lens component," that relate to the above cited patent references, as well as to the detailed description of the present invention that will follow later, will be given. The term "lens element" is herein defined as a single transparent mass of refractive material having two opposed refracting surfaces, which surfaces are positioned at least generally transverse to the optical axis of the lens. The term "lens component" is herein defined as (a) a single lens element spaced so far from any adjacent lens element that the spacing cannot be neglected in computing the optical image forming properties of the lens elements or (b) two or more lens elements that have their adjacent lens surfaces either in full overall contact or overall so close together that the spacings between adjacent lens surfaces of the different lens elements are so small that the spacings can be neglected in computing the optical image forming properties of the two or more lens elements. Thus, some lens elements may also be lens components. Therefore, the terms "lens element" and "lens component" are not mutually exclusive terms. In fact, the terms may frequently be used to describe a single lens element in accordance with part (a) above of the definition of a "lens component." Alternatively, a lens component may frequently be made by cementing lens elements together. Neither a filter with two flat faces nor a cover glass is a lens component.

In the above cited patent references, Japanese Patent S55-15004, Japanese Patent H4-3851, and Japanese Laid-Open Patent Application H7-181377 relate to objective lenses for endoscopes, and in particular to embodiments where a moving lens group is composed of plural lens components that are held in a frame. It is unavoidable that a moving lens group with a frame becomes long and heavy when the moving group is composed of plural lens components. This is undesirable because the torque of an actuator for moving the moving lens group increases and the actuator becomes large in size. Embodiments described in the above cited Japanese Laid-Open Patent Application H11-316339 having a moving lens group of positive refractive power are also undesirable for the same reasons described above with regard to Japanese Patent S55-15004, Japanese Patent H4-3851, and Japanese Laid-Open Patent Application H7-181377.

An embodiment of an objective lens for an endoscope described in the above cited Japanese Patent S55-15005 is constructed for moving only one lens component, but the ray height on the first lens component is so high in this construction that the field of view angle cannot be widened.

Embodiments having a moving lens group of negative refractive power have been described in the above cited Japanese Laid-Open Patent Application H11-316339 and Japanese Laid-Open Patent Application 2000-267002. In these embodiments, the entire length of the optical systems is long and the length of the rigid tip of the endoscope increases so that in endoscopes using such optical systems and that are capable of adjustment to different viewing angles, operability related to such adjustments deteriorates. Additionally, these optical systems are undesirable as optical systems for endoscopes strictly in terms of focusing considerations because the fluctuations of focal length associated with the lens movement are too large.

In embodiments of objective lenses for endoscopes described in the above cited Japanese Laid-Open Patent Application 2000-330015 and embodiments of an endoscope device described in the above cited Japanese Laid-Open Patent Application 2002-28126, the moving lens component is on the image most side, and these embodiments are undesirable because of the large outside diameter of the lenses required, and the large size in the radial direction of any frame mounting such a large size lens that is used with any mechanism for moving such a lens.

An optical system for an endoscope has also been described in the above cited Japanese Laid-Open Patent Application 2002-357773 with the lens component on the image most side having negative refractive power. This optical system is undesirable for use in combination with primary color single plate image pickup elements or multiplate image pickup units, such as two-plate or three-plate units, because the exit pupil distance is generally shortened.

BRIEF SUMMARY OF THE INVENTION

The present invention relates to an objective optical system suitable for a high precision endoscope having a focusing function by moving a lens component, and particularly relates to an objective optical system for an endoscope suitable for mounting an actuator for lens movement at the tip of the endoscope.

BRIEF DESCRIPTION OF THE DRAWINGS

The present invention will become more fully understood from the detailed description given below and the accompanying drawings, which are given by way of illustration only and thus are not limitative of the present invention, wherein:

FIGS. 36A-36C show the spherical aberration, astigmatism, and distortion, respectively, of Embodiment 9 of the present invention when focused at the far point on the object side, and FIGS. 36D-36F show the spherical aberration, astigmatism, and distortion, respectively, of Embodiment 9 of the present invention when focused at the near point on the object side;

FIGS. 42A-42C show the spherical aberration, astigmatism, and distortion, respectively, of Embodiment 15 of the present invention when focused at the far point on the object side, and FIGS. 42D-42F show the spherical aberration, astigmatism, and distortion, respectively, of Embodiment 15 of the present invention when focused at the near point on the object side;

FIGS. 45A-45C show the spherical aberration, astigmatism, and distortion, respectively, of Embodiment 18 of the present invention when focused at the far point on the object side, and FIGS. 45D-45F show the spherical aberration, astigmatism, and distortion, respectively, of Embodiment 18 of the present invention when focused at the near point on the object side;

FIGS. 47A-47C show the spherical aberration, astigmatism, and distortion, respectively, of Embodiment 20 of the present invention when focused at the far point on the object side, and FIGS. 47D-47F show the spherical aberration, astigmatism, and distortion, respectively, of Embodiment 20 of the present invention when focused at the near point on the object side;

FIGS. 51A-51C show the spherical aberration, astigmatism, and distortion, respectively, of Embodiment 24 of the present invention when focused at the far point on the object side, and FIGS. 51D-51F show the spherical aberration, astigmatism, and distortion, respectively, of Embodiment 24 of the present invention when focused at the near point on the object side;

DETAILED DESCRIPTION

Figure 1:
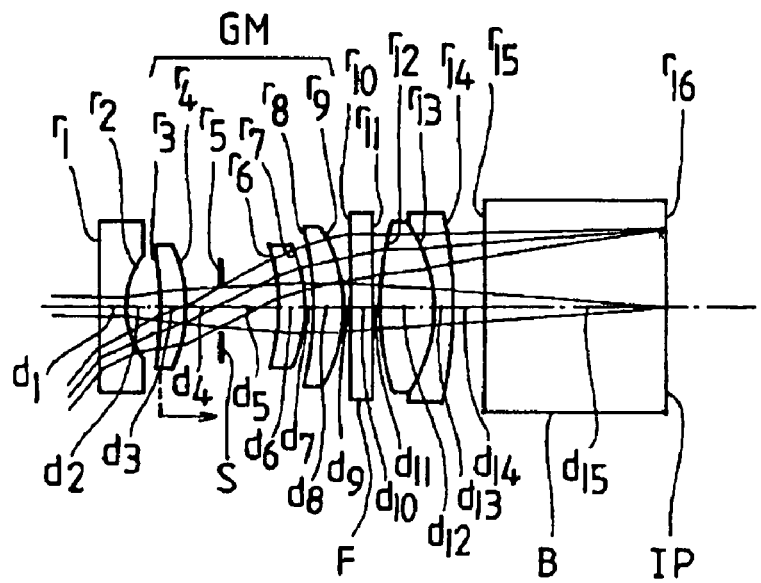
FIG. 1 is a cross-sectional view of Embodiment 1 of the present invention focused at the far point on the object side.

In a first mode of construction of the present invention, an objective optical system for an endoscope has an object side and an image side and includes, arranged along an optical axis in order from the object side, as follows: a front lens group having negative refractive power and consisting of a first lens component; a middle lens group having positive refractive power and including at least two lens components, each of said at least two lens components having positive refractive power; and a rear lens group having positive refractive power and consisting of only one lens component.

Additionally, only one lens component of said middle lens group moves in the direction of the optical axis during focusing; a stop for controlling image brightness is positioned within the middle lens group or between said front lens group and said middle lens group; and the following conditions are satisfied:

$$2 < |f_{UM}/f_{TF}| < 10 \qquad \text{Condition (1)}$$

$$-1.25 < f_{U1}/f_{TF} < -0.6 \qquad \text{Condition (2)}$$

where $f_{UM}$ is the focal length of the only one lens component of the middle lens group that moves for focusing;

$f_{TF}$ is the focal length of the entire objective optical system for an endoscope focused at the far point on the object side; and $f_{U1}$ is the focal length of the first lens component of the front lens group.

In the first mode of construction of the present invention as described above, the optical power arrangement is equivalent to a retrofocus optical power arrangement of the front lens group, which is a single lens component having negative refractive power, and the middle and rear lens groups having positive refractive power. This is a construction suited to an objective optical system for a high precision endoscope that has high power and that has requirements of favorably corrected field curvature. This construction is favorable for ensuring a large enough back focal distance to allow for insertion of a filter, prism, or similar optical device on the image side of the optical system.

In this optical system, the first lens component that forms the front lens group is stronger in refractive power relative to the other lens components in order to provide for widening of the angle of view and to correct field curvature. Therefore, coefficients related to correction of focusing and fluctuations in aberrations become large, making it disadvantageous to make this first lens component be the lens group that moves for focusing. Additionally, the first lens component seals the tip of the endoscope, making it impossible for it to be the lens group that moves for focusing. The image-side lens component, that is the rear or image-side lens group, has a principal ray height that is close to the image height, thus requiring that the image-side lens component have a large outside diameter. The middle lens group has a stop (either within it, or on its object side) for controlling image brightness. This results in a low principal ray height that allows lens elements of the middle lens group to have smaller diameters than lens elements in the other lens groups of the objective optical system.

Constructing the optical system of the present invention with only one moving lens group having the focusing function be the middle group and made of lens elements of relatively small outside diameters enables the moving lens group to be small and light weight.

The rear or image-side lens group has positive refractive power and functions as a field lens, while the middle lens group functions mainly as the lens group having positive refractive power of a retrofocus type optical system. This makes it possible for the middle lens group to have the correction capability of a high precision optical system by constructing the middle lens group with three or more lens components.

In order to reduce the occurrence of aberrations while ensuring a necessary positive refractive power of the middle lens group and reduce the sensitivity to manufacturing errors, it is preferable to make the middle lens group with positive refractive power to include at least two lens components. Moreover, it is desirable to divide the optical power in the middle lens group in order to control the optical power and the correction of the aberrations of the middle lens groups that moves for focusing. Therefore, the lens components of the middle lens group that require positive refractive power are at the object-side end and at the image-side end of the middle lens group.

Additionally, the objective optical system satisfies Conditions (1) and (2) described above.

Condition (1) above assures the desired sensitivity of the focusing movement of the moving lens component. In Condition (1), if the value of $|f_{UM}/f_{TF}|$ is less than the lower limit value of two, the optical power of the moving lens component becomes too strong, and the fluctuations of focus associated with the movement of the moving lens component become too large. This is undesirable because the movement required for focusing becomes very short and the required positional accuracy at the time of setting and maintaining the focus to a predetermined state increases. If the value of $|f_{UM}/f_{TF}|$ is greater than the upper limit value of ten of Condition (1), the optical power of the moving component becomes too weak, the movement required for focusing increases, and the frame for holding the moving lens component must be made longer.

Condition (2) above is provided to balance the outside diameter of the first lens component and the correction of field curvature. In Condition (2), if the value of $f_{U1}/f_{TF}$ is less than the lower limit value of −1.25, this is undesirable because the negative refractive power of the first lens component becomes weaker and the outside diameter of that lens component increases. If the value of $f_{U1}/f_{TF}$ is more than the upper limit value of −0.6, this is undesirable because the negative refractive power of the first lens component becomes too weak and the field curvature tends to be overcorrected, the occurrence of astigmatism increases with any eccentricity of the first lens component, and blurring of the image may easily occur.

In a second mode of construction of the present invention, an objective optical system for an endoscope has an object side and an image side and includes, arranged along an optical axis in order from the object side, as follows: a front lens group having negative refractive power and consisting of a first lens component; a middle lens group having positive refractive power and consisting of, arranged in the following order from the object side, a second lens component having positive refractive power, a third lens component, and a fourth lens component having positive refractive power; and a rear lens group having positive refractive power and consisting of a single lens component. Additionally, only one lens component in the middle lens group, that is, one of the second lens component, the third lens component, and the fourth lens component, as recited above, is moved in the direction of the optical axis in order to adjust focusing. Also, a stop for controlling image brightness is placed within the middle lens group or at the object end of the middle lens group. Furthermore, Conditions (1) and (2) set forth above are satisfied.

In the second mode of construction of the present invention, the middle lens group is constructed of three lens components. The second lens component and the fourth lens component that are the lens components on the object side and the image side, respectively, in the middle lens group have positive refractive power, as set forth above, and as also set forth in the first mode of construction of the present invention set forth above. The third lens component may have either positive or negative refractive power.

Thus, the optical system can be made into a high precision objective optical system with relatively few lens components as set forth above with regard to five lens components that are used.

In a third mode of construction of the present invention, an objective optical system for an endoscope has an object side and an image side and includes, arranged along an optical axis in order from the object side, as follows: a front lens group having negative refractive power and consisting of a first lens component; a middle lens group having positive refractive power and consisting of, arranged in the following order from the object side, a second lens component having positive refractive power, a third lens component, a fourth lens component, and a fifth lens component having positive refractive power; and a rear lens group having positive refractive power and consisting of a single lens component. Additionally, only one lens component in the middle lens group is moved in the direction of the optical axis in order to adjust focusing. Also, a stop for controlling image brightness is placed within the middle lens group or at the object end of the middle lens group. Furthermore, Conditions (1) and (2) set forth above are satisfied.

In the third mode of construction of the present invention, the middle lens group is constructed with four lens components rather than three lens components, and lens components having positive refractive power are arranged at both ends of the middle lens group. Namely, the second lens component and the fifth lens component have positive refractive power, and the third lens component and the fourth lens component may be made to have either positive or negative refractive power.

In the third mode of construction of the present invention, an additional degree of freedom in design is included by constructing the entire optical system with six lens components as compared to five lens components as in the second mode of construction of the invention. For example, an expansion of the suitable range of various values of optical system specifications and a reduction of distortion become possible.

In a fourth mode of construction of the present invention, an objective optical system for an endoscope has an object side and an image side and includes, arranged along an optical axis in order from the object side, as follows: a front lens group having negative refractive power and consisting of a first lens component; a middle lens group having positive refractive power and consisting of, arranged in the following order from the object side, a second lens component having positive refractive power, a stop for controlling image brightness, and a third lens component having positive refractive power; and a rear lens group having positive refractive power and consisting of a single lens component. Additionally, only one lens component in the middle lens group is moved in the direction of the optical axis in order to adjust focusing. Furthermore, Conditions (1) and (2) set forth above are satisfied.

In the fourth mode of construction of the present invention, the middle lens group consists of two lens components and the entire objective optical system consists of four lens components. Although an objective optical system for an endoscope of such an optical power arrangement has been known, for example, in the above cited Japanese Laid-Open Patent Application 2000-267002, such an optical system with favorably corrected aberrations that can correspond to high precision imaging may be achieved by satisfying Conditions (1) and (2) above. Therefore, the optical system can also be adopted as an optical system that includes the focusing function. In that case, having the last or image-side lens component move to make focus adjustment, like the optical system shown in Japanese Laid-Open Patent Application 2000-267002, is undesirable because the outside diameter of the moving lens component increases.

In the fourth mode of construction of the optical system of the present invention, the outside diameter of the moving lens component can be decreased by making either the second lens component or the third lens component, both of which are in the middle lens group, the lens component that moves for focusing.

In all of the first through fourth modes of construction of the present invention described above, any change in magnification due to focusing action is preferably small. More specifically, the change is preferably within a range satisfying the following condition:

$$0.85 < f_{TN}/f_{TF} < 1.15 \qquad \text{Condition (3)}$$

where $f_{TN}$ is the focal length of the entire objective optical system for an endoscope focused at the near point on the object side; and $f_{TF}$ is defined as set forth above.

The optical system of the present invention does not use change of the focal length in order to change the image size; rather, it is assumed that image expansion (i.e., zooming) using electronics would be a better alternative in order to vary the magnification of an observed image. Although optical expansion with less deterioration of image quality is generally desired, the more precise the image, the higher the spatial frequency on the monitor screen and the more a deterioration of image quality will occur when the spatial frequency on the monitor screen is lowered using electronic expansion. Therefore, it is best that electronic expansion by an image processor be entirely relied upon for zooming since electronic expansion can achieve better balance relative to the specifics of the uses and operation of an endoscope than when using an objective optical system having a zooming capability, since providing such a capability for a high precision endoscope necessarily results in the endoscope becoming larger in size.

With the best use of electronic expansion, the more the input side of imaging is limited in focusing, the more convenience of use is desired. In this regard, it is desirable that the change of optical magnification when transitioning from the far point focused state to the near point focused state be limited to within 15%, as indicated by Condition (3) above in terms of the focal lengths at the near point focus and at the far point focus.

Deviation of the optical system outside the range of Condition (3) above is undesirable because inconveniences otherwise occur too frequently, such as the viewing field being reduced too much in size that a particular point of interest is no longer within the viewing field after the focus distance is adjusted, or the viewing field being expanded too much for clear viewing after the focus distance is adjusted. These problems may require supplemental operations by the user, such as electronically changing the magnification or making back and forth movements with the inserted part in order to vary the field of view. Additionally, in the case of two step focus switching (or focusing switching using additional steps), the fluctuation of magnification associated with the focus switching is divided and thus reduced, and there will be no problem so long as Condition (3) above is satisfied for each step. When an autofocus function is added, it is also useful to satisfy Condition (3). Autofocus, once activated, operates independently of a user's intentions, and the image magnification can change greatly with autofocusing. It is physically uncomfortable to view an image that fluctuates in magnification. Fluctuations in magnification also affect the autofocus mountings and movements. For example, the control of the moving direction and amount of movement during autofocus is usually derived from fluctuations of image contrast associated with very little lens movement in a common focus detection mode. Fluctuations of image magnification affect the fluctuation of contrast, so a pure focus fluctuation component becomes difficult to detect and the accuracy of the autofocus control system deteriorates. Accordingly, when autofocus is utilized, it is desirable to satisfy Condition (3).

Regarding Condition (3), it is more preferable to set the upper limit value at unity in order to further limit the change of magnification with focus position, and thus it is further desirable that the following, more narrow, condition be satisfied:

$$0.85 < f_{TN}/f_{TF} < 1 \qquad \text{Condition (4)}$$

where $f_{TN}$ and $f_{TF}$ are defined as set forth above.

Condition (4) above assures a sufficient depth of field on the near point side, as will now be discussed. The closer the near point side, the narrower the range of focal length and the wider the depth of field on the near point side. Manual focusing is associated with a reduction of image blur and image fluctuations because of a decrease of operating frequency of an actuator. The depth of field is inversely proportional to the square of the focal length and is proportional to the f-number. Therefore, the shorter the focal length is, the greater the depth of field is (for a stop of constant size). Consequently, it is desirable that focal lengths at the near point of focusing and at the far point of focusing be set up according to Condition (4). In other words, by having the value of the ratio $f_{TN}/f_{TF}$ be unity or less, a sufficient depth of field on the near point side can be provided.

Next, it is also desirable to satisfy the following conditions in the objective optical systems for an endoscope of the present invention, with regard to all four modes of construction of the invention described above:

$$n_{U1} > 1.7 \qquad \text{Condition (5)}$$

$$v_{U1} > 38 \qquad \text{Condition (6)}$$

where $n_{U1}$ is the refractive index at the d-line of the first lens component of the front lens group; and $v_{U1}$ is the Abbe number at the d-line of the first lens component of the front lens group.

As also mentioned in the description of the first mode of construction of the present invention, in the objective optical system for an endoscope of the present invention, the first lens component of the front lens group has relatively strong negative refractive power. Therefore, it would be undesirable for that first lens component to be made as a cemented lens because that would tend to increase its thickness and, as its thickness increases, the ray height rises and the outside diameter increases. Therefore, a single lens element is preferable and, in this case, the above Conditions (5) and (6) must be satisfied.

With regard to Condition (5), it would be undesirable if $n_{U1}$ were less than 1.7 because, as the radii of curvature of the lens element surfaces decrease, the workability of the lens element deteriorates, the eccentricity correction coefficient of astigmatism also deteriorates, the total thickness of the lens element becomes greater, and the ray height increases.

With regard to Condition (6), it is undesirable that $v_{U1}$ be less than 38 because, in that case, large lateral color occurs in the first lens component and an adverse effect on the aberration correction of the entire system is created.

It is desirable that the absolute values of the focal lengths of the lens components of the middle lens group and the rear lens group, designated as $f_U$ (GM, GR), that is, the lens components other than the first lens group, be 1.4 $f_{TF}$ or greater according to all four modes of construction of the optical system of the present invention described above.

When a high precision objective optical system is designed, the eccentricity correction coefficients for astigmatism, coma aberration, and spherical aberration must be controlled in relation to the aberrations. If the correction coefficients are large, the image quality readily deteriorates due to the inclination of the lens component in the frame.

The diameters of the lens elements are small, making it difficult to suppress the eccentricity of lens components in the frames.

As described above, concentrating optical power in a specific lens component with an extremely large eccentricity correction coefficient can be avoided by making the absolute values of focal lengths of the lens components of the middle lens group and the rear lens group, designated as $f_U$ (GM, GR), that is, the absolute values $|f_U(\text{GM,GR})|$, to be 1.4 $f_{TF}$ or greater.

If it is necessary for the absolute values of the focal lengths of these lens components to be less than 1.4 $f_{TF}$, special consideration becomes necessary so as to reduce the eccentricity of the lens components in the frame, making it critical that the frame be constructed with high accuracy.

It is also desirable that the absolute values of the radii of curvature of the lens element surfaces of the lens components other than those in the first lens group, designated $|R(\text{GM, GR})|$, be 0.8 $f_{TF}$ or greater in the optical system of the present invention.

The conditions above concerning the focal lengths of the lens components other than those in the first lens group are based on considering the eccentricity correction coefficients, but the condition above concerning the radii of curvature of these lens components, that is, the condition requiring their absolute values to be greater than 0.8 $f_{TF}$, is a condition based on considering the eccentricity correction coefficients of the lens element surfaces. If the eccentricity of the lens element surfaces, which are based on their outside diameters that relate to astigmatism, coma aberration, and spherical aberration, and the central deviation at cemented surfaces are large, the image quality readily deteriorates. In order to improve the correction coefficients, it is necessary not to decrease too much the absolute values of the radii of curvature of the lens element surfaces of the lens components. It would be undesirable if the absolute values of the radii of curvature of the lens element surfaces become 0.8 $f_{TF}$ or less because the centering accuracy and the cementing accuracy of the lens components must be strict.

It is desirable that the last lens component that forms the rear lens group be a cemented lens component according to the first through fourth modes of construction of the objective optical system for an endoscope of the present invention as described above. It is desirable that the cemented lens be formed of a lens element having negative refractive power with a refractive index ($n_d$) greater than 1.82 and an Abbe number ($v_d$) of less than 26 and a lens element having positive refractive index with a refractive index ($n_d$) of less than 1.78 and an Abbe number ($v_d$) greater than 49.

If the lens elements forming the last lens component do not satisfy the above requirements, the lateral color and astigmatism (caused by the effect of cementing together lens surfaces in a part where the principal ray in the vicinity of the image side is high) will be excessive, making aberration correction difficult.

Additionally, it is desirable that the last lens component satisfy the following condition:

$$2 < f_{UR}/f_{TF} < 12 \quad \text{Condition (7)}$$

where $f_{UR}$ is the focal length of the image-side lens component of the rear lens group; and $f_{TF}$ is defined as set forth above.

The principal ray height is high in the image-side lens component of the rear lens group. Therefore, that lens component acts as a field lens with a role of controlling astigmatism and lateral color. On the other hand, the middle lens group shares in the correction of spherical aberration, coma aberration and axial chromatic aberration as described above.

Consequently, if the value of $f_{UR}/f_{TF}$ is lower than the lower limit value of two, the image-side lens component of the rear lens group has a strong focusing action, excessively increasing problems of spherical aberration and coma aberration so that aberration correction of the optical system becomes difficult.

It is preferable to include in the objective optical system for an endoscope of the present invention, according to all of the first through fourth modes of construction described above, two or more cemented lens components, each formed of a lens element having negative refractive power and a lens element having positive refractive with the lens element having positive refractive power having a refractive index at the d-line at least 0.1 less than that of the lens element having negative refractive power to which it is cemented.

In the optical system of the present invention, the Petzval sum may easily be a negative value because the first lens component has strong negative refractive power, thus causing the field curvature to easily be overcorrected.

Therefore, it is effective to increase the degrees of freedom for correcting the Petzval sum toward positive values by increasing the use of cemented lens components formed of a lens element having negative refractive power and a relatively high refractive index cemented to a lens element having positive refractive power and a relatively low refractive index. The Petzval sum becomes a design restriction before other aberration corrections because it is determined only by optical power arrangements and refractive indices. Therefore, it is undesirable for the above design criteria not to be satisfied, because that would decrease the feasibility of aberration correction.

In the optical system of the present invention, it is desirable that the lens component arranged in the middle lens group and that is moved for focusing have positive refractive power from a viewpoint of efficiency of optical power arrangements, including the middle lens group having positive refractive power as a whole. When the moving lens component is formed as a single lens element having positive refractive power, it is more preferable that the refractive index $n_d$ at the d-line be less than 1.75. If the correction of field curvature with cemented lens components as set forth above is also considered, it is preferable that the single lens element having positive refractive power have a lower refractive index in order to make it easy to correct the Petzval sum in the positive direction. In embodiments of the present invention, it is desirable to make the moving lens component to be a single lens element having positive refractive power and to use material with a low refractive index so as to enhance the capability of making desired physical shapes of the lens element because the Z coefficient can be increased. It would be undesirable to have the refractive index of the lens element be above 1.75 because the degree of freedom for design of the optical system would be reduced due to restrictions on the optical power arrangement, field curvature would tend to be excessive, and it would be more difficult to ensure accuracy of the Z coefficient.

In the optical system of the present invention, it is preferable to use a cemented lens component having positive refractive power as the moving lens component because the restriction of the Z coefficient in the case of a positive single lens is eliminated. When the moving lens component is constructed as a positive cemented lens, it is preferable to cement a lens element having negative refractive power and a lens element having positive refractive with a refractive index at the d-line at least 0.1 less than that of the lens element having negative refractive power to which it is cemented. This combination relaxes restrictions on design related to the Petzval sum, as described above. It would be undesirable if this design criterion was not satisfied, as failing to satisfy this design criterion would reduce the feasibility of aberration correction.

It is desirable, as described above, that the lens component moved for focusing be adjacent to a stop for controlling image brightness. The moving lens component adjacent to the brightness stop has the lowest principal ray height in the middle lens group. Therefore, if the lens component adjacent to the brightness stop is the lens component moved for focusing, the outside diameter of that lens component can be reduced. It would be undesirable if this design criterion were not satisfied, because then the lens component moved for focusing would tend to become larger and heavier.

The fourth mode of construction of the present invention, described above, wherein the middle lens group consists of a second lens component and a third lens component with a brightness stop between them and either lens component of the middle lens group is moved for focusing may be implemented to also satisfy the requirements described above.

When the middle lens group includes more than two lens components, it is desirable that the lens component moved for focusing be a lens component that is not at either end of the middle lens group. The lens component moved for focusing is positioned near the center of the entire objective optical system. In a retrofocus type objective optical system, the center position is a place where an axial beam is close to a relatively a focal beam and fluctuation of axial aberrations, spherical aberration and axial chromatic aberration associated with the movement of the focusing lens component is easily reduced, making it possible to emphasize correction of off-axis aberrations, astigmatism and lateral color, that fluctuate with movement of the focusing lens component, thereby reducing restrictions on the design for aberration correction. If the above design criterion is not satisfied, this is undesirable because the aberration fluctuation associated with the movement increases.

In the first mode of construction of the objective optical system for an endoscope of the present invention, the middle lens group is formed of two or more lens components, and one or more of these lens components satisfy the above criteria. In the second mode of construction of the objective optical system for an endoscope of the present invention, the middle lens group consists of only three lens components. In the third mode of construction, the third and the fourth lens components satisfy the above criteria. In the fourth mode of construction of the objective optical system for an endoscope of the present invention, the three design criteria described above are not required, but these design criteria relate to the lens being moved for focusing being limited to one of the second and third lens components.

As described above, it is variously preferable that the lens component moved for focusing not be at either end of the middle lens group and that the lens component moved for focusing be adjacent the stop for controlling image brightness and have a positive refractive power as set forth above with regard to the first through third modes of construction of the present invention.

An actuator for driving the lens component that moves for focusing is small in the radial direction of the insertion part of the endoscope, and an electronically controllable actuator is desirable. A shape memory alloy actuator is considered as an exemplary choice for the actuator. It is known that if a voltage is applied to a wire formed of a shape memory alloy material such as titanium nickel, a force is produced when the wire is heated to a high temperature by electric resistance, and contraction in the longitudinal direction is great. The alloy materials can be used not only in the form of wire but also in the form of coils. The length of wire and/or coils of the shape memory alloys can be changed by temperature controlled through an applied voltage.

An objective optical system for an endoscope of the present invention has a wide field angle, has good correction of various aberrations, including curvature of field, and provides for focus adjustment with movement of a lens component having a small diameter and a small size, proper sensitivity throughout the range of movement for focusing, and little fluctuation in image quality throughout the range of movement for focusing.

Embodiments 1 through 27 of the objective optical system for an endoscope of the present invention will now be individually described with further reference to the drawings. In all of Embodiments 1 through 27, the data of the objective optical system of each embodiment is shown in a corresponding table. At the top of each of these tables are listed values of the working distance WD (in mm) for the far point focused state and the near point focused state as well as the focal length (in mm), the f-number (i.e., $F_{NO}$), and the field angle $2\omega$ (in degrees) at both the far point focused state (focal length $f_{TF}$) and near point focused state (focal length $f_{TN}$). Below that in each table are listed for each optical surface, as numbered from the object side through the use of subscripts, the radius of curvature r (in mm) on the optical axis of each optical surface, the on-axis surface spacing d (in mm) at the far point focused state, as well as the refractive index n and the Abbe number v (both as measured at the d-line wavelength of 587.6 nm) for the material on the image side of the optical surface. Below that in each table are listed the values $|f_{UM}/f_{TF}|$, $f_{U1}/f_{TF}$, and $f_{TN}/f_{TF}$, related to the above Conditions (1), (2) and (3)-(4), respectively. Below that in each table are listed the focal lengths of the lens components in order from the object side (left column), as well as the ratio of these focal lengths to $f_{TF}$ (right column). Below that in each table are listed the minimum value of the absolute values of the focal lengths of the lens components of each of the middle lens group and lens components of the rear or image-side lens group, $|f_U(GM,GR)|_{min}$ and the minimum value of the absolute values of the radii of curvature of the lens elements of the lens components of the middle lens group and the lens elements of the lens components of the rear or image-side lens group, $|R(GM,GR)|_{min}$. Below that in each table, except in the tables of Embodiments 6 and 26, are listed for the rear or image-side lens group (that consists of a cemented lens component formed of a lens element having negative refractive power and a lens element having positive refractive power) the refractive index of the lens element having positive refractive power, the refractive index of the lens element having negative refractive power, as well as the Abbe number of the lens element having positive refractive power and the Abbe number of the lens element having negative refractive power, all values being measured at the d-line wavelength of 587.6 nm. For each embodiment, figures are provided that show the spherical aberration (in mm), the astigmatism (in mm) in both the sagittal (S) and meridional (M) image planes, and the distortion (in %), as discussed further below.

EMBODIMENT 1

FIG. 1 shows a cross-sectional view of the objective optical system for an endoscope of Embodiment 1 of the present invention. In FIG. 1, as well as in FIGS. 2-26, IP is the image plane. Table 1 below lists the various data explained above for Embodiment 1.

TABLE 1

| Far point focused state | | | |
|---|---|---|---|
| WD = 48 | $f_{TF}$ = 1.790 | $F_{NO}$ = 4.48 | $2\omega$ = 98.6° |
| Near point focused state | | | |
| WD = 23 | $f_{TN}$ = 1.758 | $F_{NO}$ = 4.48 | $2\omega$ = 100.9° |

| | | | |
|---|---|---|---|
| $r_1 = \infty$ | $d_1 = 0.5000$ | $n_1 = 1.76820$ | $v_1 = 71.79$ |
| $r_2 = 1.4291$ | $d_2 = 0.6995$ | | |
| $r_3 = -6.9299$ | $d_3 = 0.5800$ | $n_2 = 1.72916$ | $v_2 = 54.68$ |
| $r_4 = -2.5937$ | $d_4 = 0.6725$ | | |
| $r_5 = \infty$ (stop) | $d_5 = 1.0825$ | | |
| $r_6 = -4.1260$ | $d_6 = 0.6000$ | $n_3 = 1.72916$ | $v_3 = 54.68$ |
| $r_7 = -2.6280$ | $d_7 = 0.1000$ | | |
| $r_8 = -6.3523$ | $d_8 = 0.6000$ | $n_4 = 1.80610$ | $v_4 = 40.92$ |
| $r_9 = -3.0721$ | $d_9 = 0.1000$ | | |
| $r_{10} = \infty$ | $d_{10} = 0.4500$ | $n_5 = 1.51800$ | $v_5 = 75.00$ |
| $r_{11} = \infty$ | $d_{11} = 0.1000$ | | |
| $r_{12} = 5.1077$ | $d_{12} = 1.1000$ | $n_6 = 1.58913$ | $v_6 = 61.14$ |
| $r_{13} = -2.7000$ | $d_{13} = 0.3000$ | $n_7 = 1.92286$ | $v_7 = 18.90$ |
| $r_{14} = -8.6620$ | $d_{14} = 0.6000$ | | |
| $r_{15} = \infty$ | $d_{15} = 3.6000$ | $n_8 = 1.48749$ | $v_8 = 70.23$ |
| $r_{16} = \infty$ (image plane) | | | |

| $|f_{UM}/f_{TF}|$ = 3.006 | $f_{U1}/f_{TF}$ = −1.039 | $f_{TN}/f_{TF}$ = 0.982 |
|---|---|---|

| | |
|---|---|
| $f_{U1} = -1.860$ | $f_{U1}/f_{TF} = -1.04$ |
| $f_{U2} = 5.381$ | $f_{U2}/f_{TF} = 3.01$ |
| $f_{U3} = 8.493$ | $f_{U3}/f_{TF} = 4.75$ |
| $f_{U4} = 6.823$ | $f_{U4}/f_{TF} = 3.81$ |
| $f_{UR} = 10.039$ | $f_{UR}/f_{TF} = 5.61$ |
| $|f_U(GM, GR)|_{min} = 3.01$ | $|R(GM, GR)|_{min} = 1.45$ |
| $n(GR_p) = n_6 = 1.58913$ | $n(GR_n) = n_7 = 1.92286$ |
| $v(GR_p) = v_6 = 61.14$ | $v(GR_n) = v_7 = 18.90$ |

The optical system of Embodiment 1, as shown in FIG. 1, is composed of: a front lens group that consists of a lens component that has negative refractive power and is formed of a single lens element with lens surfaces having radii of curvature $r_1$ and $r_2$; a middle lens group that consists of three lens components that are all single lens elements having positive refractive power, specifically, a second lens element having radii of curvature $r_3$ and $r_4$, a third lens element having radii of curvature $r_6$ and $r_7$, and a fourth lens element having radii of curvature $r_8$ and $r_9$; and a rear lens group that consists of a cemented lens component made up of a biconvex lens element and a meniscus lens element having negative refractive power with radii of curvature $r_{12}$, $r_{13}$, and $r_{14}$.

Embodiment 1 is an example of an optical system according to the first and second modes of construction of the present invention described above with regard to the middle lens group, referenced by "GM" in Table 1 above and in FIG. 1, being composed of three lens components, namely, a second lens component having positive refractive power, a third lens component, and a fourth lens component, in order from the object side.

A stop S for controlling image brightness and having a radius of curvature $r_5$ is arranged between the second lens component and the third lens component in the middle lens group at a position having a relatively low ray height. The second lens component moves toward the image side during focusing from the far point to the near point as indicated by the directional arrow in FIG. 1 over a range indicated by the data of Table 1 above. This second lens component is a single lens element, has a relatively small diameter and is relatively thin, and is made with a supporting frame capable of being of small size and lightweight and thus suitable for being easily moved. The first lens component is a plano-concave lens element made of highly durable sapphire ($n_d$=1.76820, $v_d$=71.79) and protects the object-side surface. A plane parallel plate F with radii of curvature $r_{10}$ and $r_{11}$ is arranged between the fourth lens component and the last lens group and operates as an absorption infrared cutoff filter ($n_d$=1.5180, $v_d$=75.00) on which a laser reflecting film may be deposited as necessary for the design. A cemented lens component is used for the last lens component in order to correct astigmatism and lateral color. A glass block B, having radii of curvature $r_{15}$ and $r_{16}$ is arranged on the image-most side or in simpler designs may be replaced by single-plate, solid-state image pickup elements. Alternatively, the optical axis may be folded 90° using an optical path conversion prism, and single-plate image pickup elements may be placed horizontally or a multi-plate (e.g., two-plate) image pickup unit may be used.

Embodiment 1 of the present invention satisfies Conditions (1) through (7) above. The focal lengths $f_U$(GM,GR) of the lens components in the middle lens group and rear lens group and the radii of curvature R(GM,GR) of lens surfaces of the lens components in the middle lens group and rear lens group also satisfy the applicable conditions and design criteria as specified for them. As described above, the last lens component is a cemented lens component, and the refractive indices $n(GR_p)$ and $n(GR_n)$ and the Abbe numbers $v(GR_p)$ and $v(GR_n)$ of the lens materials of this lens component also satisfy the applicable conditions and design criteria of the present invention.

Figure 28A:
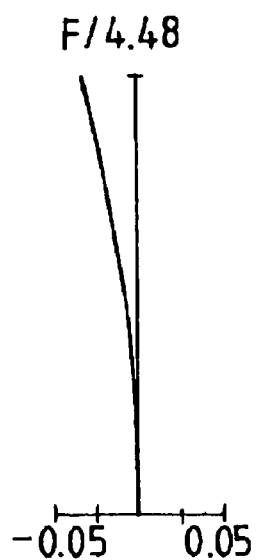
FIGS. 28A-28C show the spherical aberration, astigmatism, and distortion, respectively, of Embodiment 1 of the present invention when focused at the far point on the object side.
Figure 28B:
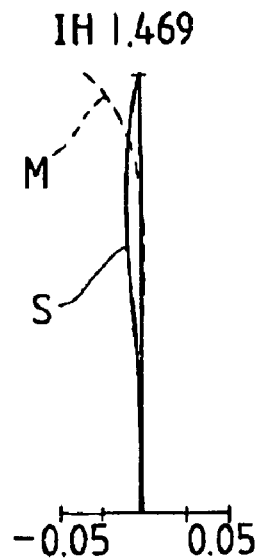
Figure 28C:
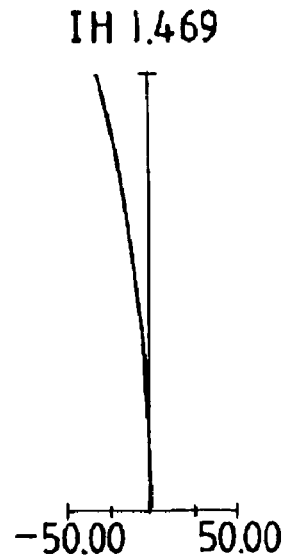
Figure 28D:
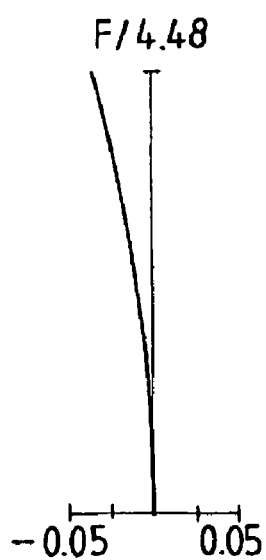
FIGS. 28D-28F show the spherical aberration, astigmatism, and distortion, respectively, of Embodiment 1 of the present invention when focused at the near point on the object side.
Figure 28E:
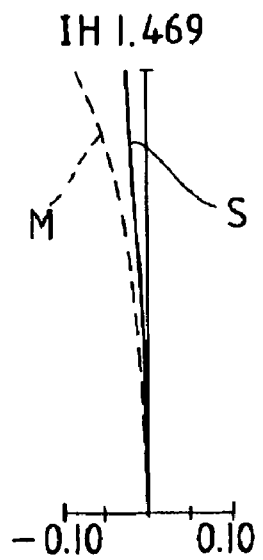
Figure 28F:
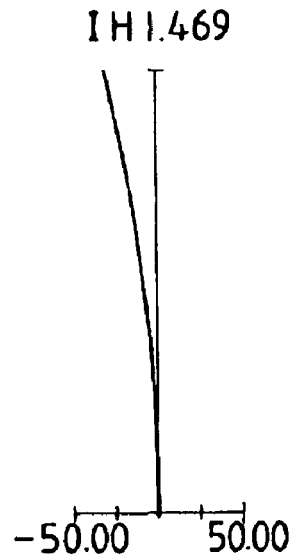

FIGS. 28A-28C show the spherical aberration, astigmatism, and distortion, respectively, of Embodiment 1 of the present invention when focused at the far point on the object side, and FIGS. 28D-28F show the spherical aberration, astigmatism, and distortion, respectively, of Embodiment 1 of the present invention when focused at the near point on the object side. As shown in FIGS. 28A-28C and FIGS. 28D-28F, in Embodiment 1 these aberrations are favorably corrected.

EMBODIMENT 2

Figure 2:
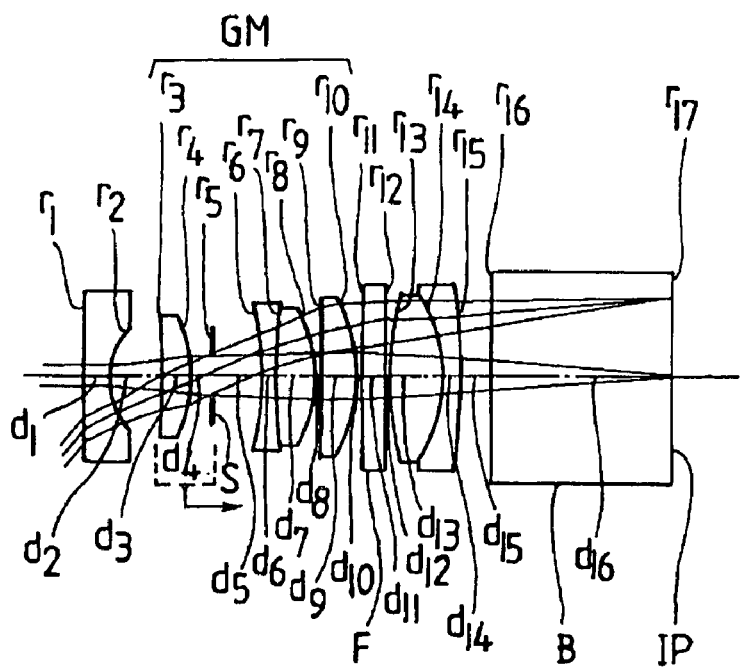
FIG. 2 is a cross-sectional view of Embodiment 2 of the present invention focused at the far point on the object side.

FIG. 2 shows a cross-sectional view of the objective optical system for an endoscope of Embodiment 2 of the present invention. Table 2 below lists the various data explained above for Embodiment 2.

TABLE 2

| Far point focused state | | | |
|---|---|---|---|
| WD = 47 | $f_{TF}$ = 1.800 | $F_{NO}$ = 4.52 | 2 ω = 98.6° |
| Near point focused state | | | |
| WD = 23 | $f_{TN}$ = 1.765 | $F_{NO}$ = 4.55 | 2 ω = 100.9° |

| | | | |
|---|---|---|---|
| $r_1$ = ∞ | $d_1$ = 0.5000 | $n_1$ = 1.76820 | $v_1$ = 71.79 |
| $r_2$ = 1.4200 | $d_2$ = 1.0546 | | |
| $r_3$ = −11.8050 | $d_3$ = 0.6000 | $n_2$ = 1.80100 | $v_2$ = 34.97 |
| $r_4$ = −2.8044 | $d_4$ = 0.3904 | | |
| $r_5$ = ∞ (stop) | $d_5$ = 1.0008 | | |
| $r_6$ = −5.1964 | $d_6$ = 0.3000 | $n_3$ = 1.80518 | $v_3$ = 25.42 |
| $r_7$ = 16.3100 | $d_7$ = 0.7500 | $n_4$ = 1.51742 | $v_4$ = 52.43 |
| $r_8$ = −2.7213 | $d_8$ = 0.1000 | | |
| $r_9$ = −30.4133 | $d_9$ = 0.6500 | $n_5$ = 1.83481 | $v_5$ = 42.71 |
| $r_{10}$ = −3.6000 | $d_{10}$ = 0.1000 | | |
| $r_{11}$ = ∞ | $d_{11}$ = 0.4500 | $n_6$ = 1.51800 | $v_6$ = 75.00 |
| $r_{12}$ = ∞ | $d_{12}$ = 0.1000 | | |
| $r_{13}$ = 6.2138 | $d_{13}$ = 1.0000 | $n_7$ = 1.58913 | $v_7$ = 61.14 |
| $r_{14}$ = −2.8000 | $d_{14}$ = 0.3000 | $n_8$ = 1.84666 | $v_8$ = 23.78 |
| $r_{15}$ = −17.3297 | $d_{15}$ = 0.6000 | | |
| $r_{16}$ = ∞ | $d_{16}$ = 3.6000 | $n_9$ = 1.48749 | $v_9$ = 70.23 |
| $r_{17}$ = ∞ (image plane) | | | |

| | | |
|---|---|---|
| $\|f_{UM}/f_{TF}\|$ = 2.478 | $f_{U1}/f_{TF}$ = −1.027 | $f_{TN}/f_{TF}$ = 0.981 |
| $f_{U1}$ = −1.848 | $f_{U1}/f_{TF}$ = −1.03 | |
| $f_{U2}$ = 4.460 | $f_{U2}/f_{TF}$ = 2.48 | |
| $f_{U3}$ = 26.144 | $f_{U3}/f_{TF}$ = 14.52 | |
| $f_{U4}$ = 4.838 | $f_{U4}/f_{TF}$ = 2.69 | |
| $f_{UR}$ = 18.451 | $f_{UR}/f_{TF}$ = 10.25 | |
| $\|f_U (GM, GR)\|_{min}$ = 2.48 | $\|R (GM, GR)\|_{min}$ = 1.51 | |
| $n(GR_p) = n_7$ = 1.58913 | $n(GR_n) = n_8$ = 1.84666 | |
| $v(GR_p) = v_7$ = 61.14 | $v(GR_n) = v_8$ = 23.78 | |

The optical system of Embodiment 2, as shown in FIG. 2, is composed of: a front lens group that consists of a first lens component that has negative refractive power and is formed of a single lens element with lens surfaces having radii of curvature $r_1$ and $r_2$; a middle lens group that consists of three lens components, namely, a second lens component that is formed as a single lens element having radii of curvature $r_3$ and $r_4$, a cemented third lens component made up of a biconcave lens element cemented to a biconvex lens element with radii of curvature $r_6$, $r_7$, and $r_8$, and a fourth lens component that is formed as a single lens element having positive refractive power and radii of curvature $r_9$ and $r_{10}$; and a rear lens group that consists of a cemented lens component made up of a biconvex lens element cemented to a meniscus lens element having negative refractive power with radii of curvature $r_{13}$, $r_{14}$, and $r_{15}$.

Embodiment 2 is also an example of an optical system according to the first and second modes of construction of the present invention described above with regard to the middle lens group, referenced by "GM" in Table 2 above and in FIG. 2, being composed of three lens components, namely, a second lens component having positive refractive power, a third lens component, and a fourth lens component having positive refractive power, in order from the object side. A stop S for controlling image brightness and having a radius of curvature $r_5$ is arranged between the second lens component and the third lens component in the middle lens group. A plane parallel plate F with radii of curvature $r_{11}$ and $r_{12}$ is arranged between the fourth lens component and the rear lens group and operates as an absorption infrared cutoff filter, and a glass block B, having radii of curvature $r_{16}$ and $r_{17}$, is arranged on the image-most side of the optical system.

Embodiment 2 is different from Embodiment 1 in that the stop S that controls image brightness is moved integrally with the lens component that moves for focusing and in that the third lens component is a cemented lens. Other features of Embodiment 2 are very similar to Embodiment 1. When the stop S that controls image brightness moves along with the lens component that moves for focusing, the f-number and the position of the exit pupil change, but these changes are slight in the optical system of Embodiment 2. Whether the stop controlling image brightness is moved integrally with the lens component that moves for focusing may be decided by considerations of the preferred frame structures for mounting the particular optical elements. These considerations may be applied to the other disclosed embodiments of the present invention in determining the applicability of moving the stop with the lens component moved for focusing.

In Embodiment 2, as described above, the third lens component is formed as a cemented lens component and the control of axial chromatic aberration and spherical aberration is easily performed. Therefore, the aberration correction associated with a lens surface of small curvature may not create a problem, and the fluctuations in aberrations due to eccentricity of a lens surface can be reduced. The meniscus shape of the meniscus lens element also does not have to be so pronounced, thus improving the workability of lens elements used.

In Embodiment 2, the field curvature readily tends to be overcorrected due to a strong negative refractive power of the first lens component, but the correction of curvature of field is easily made by adding a cemented lens component formed of a lens having positive refractive power and a low refractive index with a lens element having negative refractive power and a high refractive index.

Embodiment 2 of the present invention, just as with Embodiment 1, satisfies Conditions (1) through (7) above. The focal lengths $f_U(GM,GR)$ of the lens components in the middle lens group and rear lens group and the radii of curvature $R(GM,GR)$ of the lens surfaces of the lens components in the middle lens group and rear lens group also satisfy the applicable conditions and design criteria as specified for them. As described above, the refractive indices $n(GR_p)$ and $n(GR_n)$ and the Abbe numbers $v(GR_p)$ and $v(GR_n)$ of the lens materials of the cemented lens component that is the last lens component of the rear lens group also satisfy the applicable conditions and design criteria of the present invention.

Figure 29A:
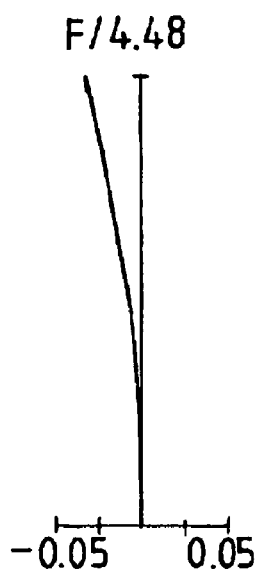
FIGS. 29A-29C show the spherical aberration, astigmatism, and distortion, respectively, of Embodiment 2 of the present invention when focused at the far point on the object side.
Figure 29B:
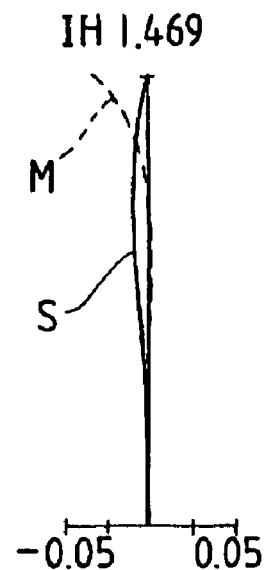
Figure 29C:
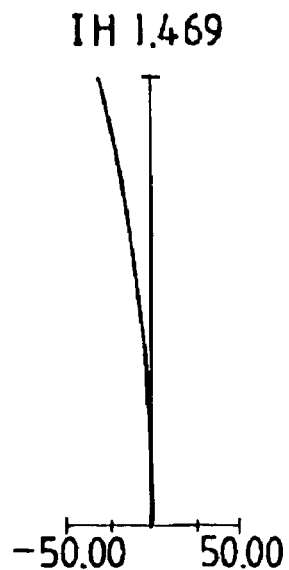
Figure 29D:
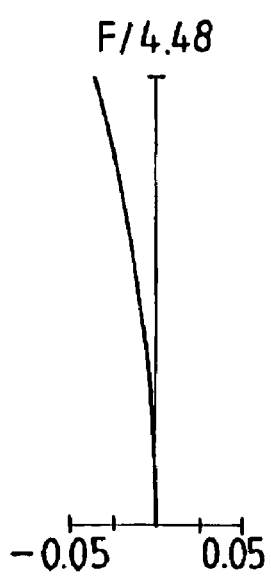
FIGS. 29D-29F show the spherical aberration, astigmatism, and distortion, respectively, of Embodiment 2 of the present invention when focused at the near point on the object side.
Figure 29E:
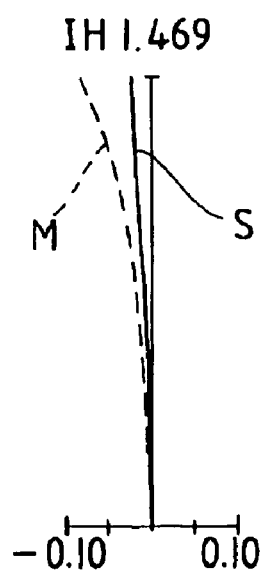
Figure 29F:
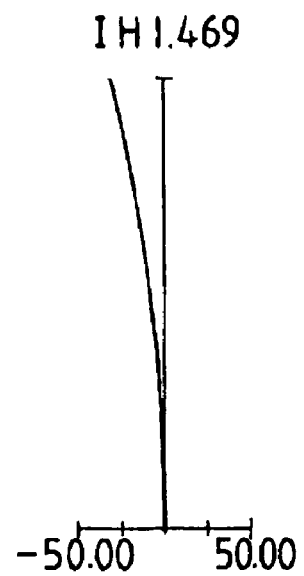

FIGS. 29A-29C show the spherical aberration, astigmatism, and distortion, respectively, of Embodiment 2 of the present invention when focused at the far point on the object side, and FIGS. 29D-29F show the spherical aberration, astigmatism, and distortion, respectively, of Embodiment 2 of the present invention when focused at the near point on the object side. As shown in FIGS. 29A-29C and FIGS. 29D-29F, in Embodiment 2 these aberrations are favorably corrected.

EMBODIMENT 3

Figure 3:
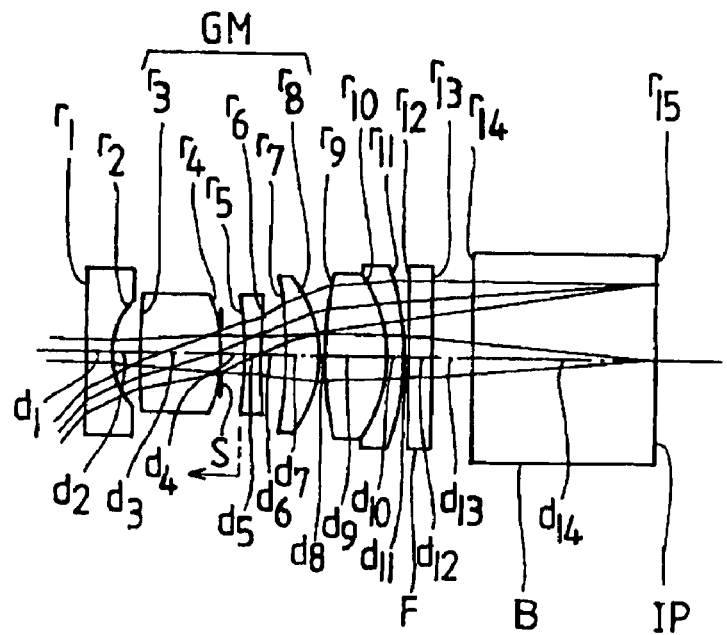
FIG. 3 is a cross-sectional view of Embodiment 3 of the present invention focused at the far point on the object side.

FIG. 3 shows a cross-sectional view of the objective optical system for an endoscope of Embodiment 3 of the present invention. Table 3 below lists the various data explained above for Embodiment 3.

TABLE 3

| Far point focused state | | | |
|---|---|---|---|
| WD = 46 | $f_{TF}$ = 1.845 | $F_{NO}$ = 4.46 | 2ω = 98.6° |
| Near point focused state | | | |
| WD = 23 | $f_{TN}$ = 1.789 | $F_{NO}$ = 4.35 | 2ω = 102.6° |
| $r_1 = \infty$ | $d_1 = 0.5000$ | $n_1 = 1.76820$ | $v_1 = 71.79$ |
| $r_2 = 1.3633$ | $d_2 = 0.5500$ | | |
| $r_3 = 9.9958$ | $d_3 = 1.6230$ | $n_2 = 1.80100$ | $v_2 = 34.97$ |
| $r_4 = -3.4155$ (stop) | $d_4 = 0.5076$ | | |
| $r_5 = -6.3158$ | $d_5 = 0.3000$ | $n_3 = 1.88300$ | $v_3 = 40.76$ |
| $r_6 = 13.0944$ | $d_6 = 0.5000$ | | |

TABLE 3-continued

| | | | |
|---|---|---|---|
| $r_7 = -8.2243$ | $d_7 = 0.7000$ | $n_4 = 1.72916$ | $v_4 = 54.68$ |
| $r_8 = -2.2479$ | $d_8 = 0.1000$ | | |
| $r_9 = 6.1134$ | $d_9 = 1.2000$ | $n_5 = 1.72916$ | $v_5 = 54.68$ |
| $r_{10} = -2.7228$ | $d_{10} = 0.3000$ | $n_6 = 1.92286$ | $v_6 = 18.90$ |
| $r_{11} = -6.2637$ | $d_{11} = 0.1000$ | | |
| $r_{12} = \infty$ | $d_{12} = 0.4500$ | $n_7 = 1.51800$ | $v_7 = 75.00$ |
| $r_{13} = \infty$ | $d_{13} = 0.8000$ | | |
| $r_{14} = \infty$ | $d_{14} = 3.6000$ | $n_8 = 1.48749$ | $v_8 = 70.23$ |
| $r_{15} = \infty$ (image plane) | | | |

| $|f_{UM}/f_{TF}| = 2.597$ | $f_{U1}/f_{TF} = -0.962$ | $f_{TN}/f_{TF} = 0.970$ |
|---|---|---|

| | |
|---|---|
| $f_{U1} = -1.775$ | $f_{U1}/f_{TF} = -0.96$ |
| $f_{U2} = 3.359$ | $f_{U2}/f_{TF} = 1.82$ |
| $f_{U3} = -4.791$ | $f_{U3}/f_{TF} = -2.60$ |
| $f_{U4} = 4.043$ | $f_{U4}/f_{TF} = 2.19$ |
| $f_{UR} = 5.321$ | $f_{UR}/f_{TF} = 2.88$ |
| $|f_U (GM, GR)|_{min} = 1.82$ | $|R (GM, GR)|_{min} = 1.22$ |
| $n(GR_p) = n_5 = 1.72916$ | $n(GR_n) = n_6 = 1.92286$ |
| $v(GR_p) = v_5 = 54.68$ | $v(GR_n) = v_6 = 18.90$ |

As shown in FIG. 3, the optical system of Embodiment 3 is composed of: a front lens group that consists of a first lens component that has negative refractive power and is formed of a single lens element with lens surfaces having radii of curvature $r_1$ and $r_2$; a middle lens group that consists of three lens components, specifically, a biconvex second lens element having radii of curvature $r_3$ and $r_4$, a biconcave third lens element having radii of curvature $r_5$ and $r_6$, and a fourth lens element having positive refractive power and a meniscus shape and radii of curvature $r_7$ and $r_8$; and a rear lens group that consists of a cemented lens component made up of a biconvex lens element and a meniscus lens element having negative refractive power with radii of curvature $r_9$, $r_{10}$, and $r_{11}$.

Embodiment 3 is an example of an optical system according to the first and second modes of construction of the present invention described above with regard to the middle lens group, referenced by "GM" in Table 3 above and in FIG. 3, that is composed of three lens components, namely, a second lens component having positive refractive power, a third lens component, and a fourth lens component having positive refractive power, in order from the object side.

In Embodiment 3, the third lens component, which is the lens component having negative refractive power in the middle lens group, is the lens component that moves for focusing. This moving lens component is moved toward the object side during focusing from the far point to the near point. Because the third lens component has negative refractive power, the positive refractive power in the area immediately on the image side of that third lens component tends to be insufficient. Therefore, the image-side lens component of the rear lens group is arranged on the object side of the plane parallel plate F with radii of curvature $r_{12}$ and $r_{13}$ in order to compensate for that optical power deficiency. The stop for controlling image brightness is positioned on the image-side lens surface of the second lens component.

In Embodiment 3, the design of the optical system according to the second mode of construction of the present invention is possible even if the third lens component is constructed so as to have negative refractive power and, in practice, sufficient aberration correction can be achieved even when the lens component having negative refractive power is moved for focusing.

Embodiment 3 of the present invention also satisfies Conditions (1) through (7) above, as shown by Table 3 above. The focal lengths $f_U(GM,GR)$ of the lens components in the middle lens group and rear lens group and the radii of curvature R(GM,GR) of the lens element surfaces of the lens components in the middle lens group and rear lens group also satisfy the applicable conditions and design criteria specified for them. As described above, the refractive indices $n(GR_p)$ and $n(GR_n)$ and the Abbe numbers $v(GR_p)$ and $v(GR_n)$ of the lens materials of the cemented lens component that is the last lens component of the rear lens group also satisfy the applicable conditions and design criteria of the present invention.

Figure 30A:
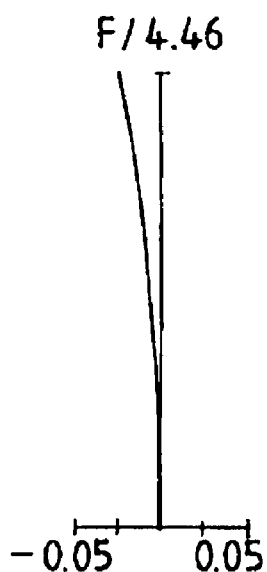
FIGS. 30A-30C show the spherical aberration, astigmatism, and distortion, respectively, of Embodiment 3 of the present invention when focused at the far point on the object side.
Figure 30B:
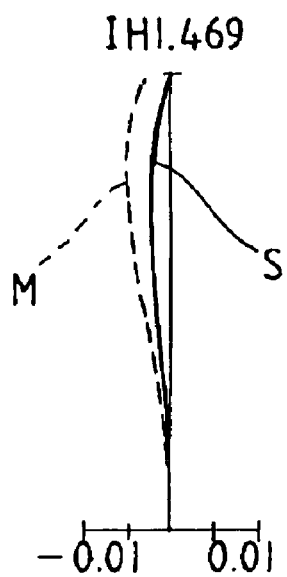
Figure 30C:
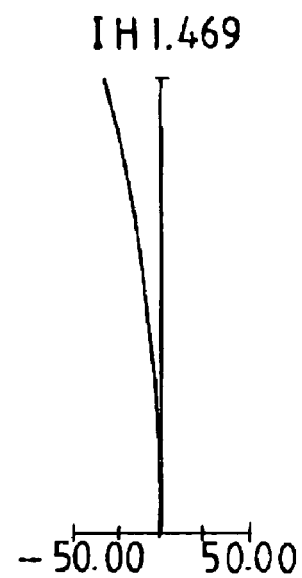
Figure 30D:
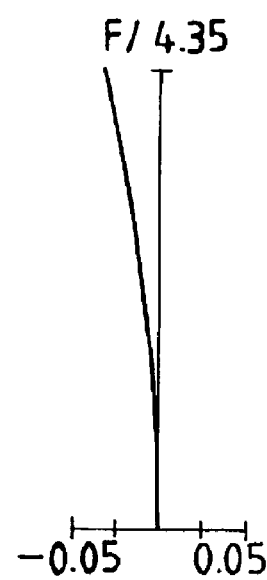
FIGS. 30D-30F show the spherical aberration, astigmatism, and distortion, respectively, of Embodiment 3 of the present invention when focused at the near point on the object side.
Figure 30E:
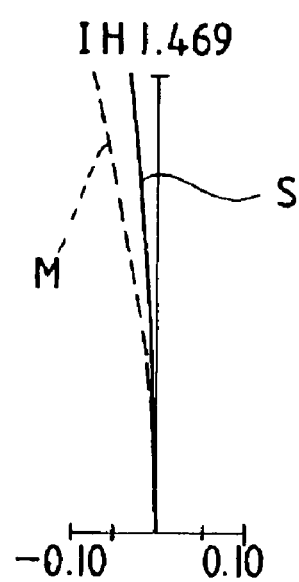
Figure 30F:
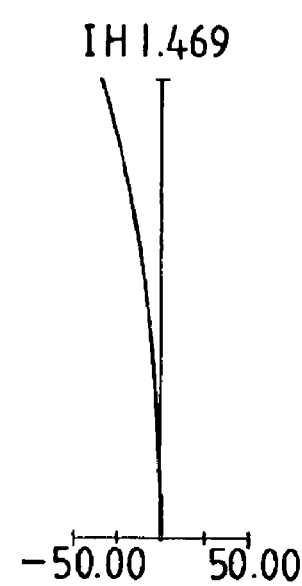

FIGS. 30A-30C show the spherical aberration, astigmatism, and distortion, respectively, of Embodiment 3 of the present invention when focused at the far point on the object side, and FIGS. 30D-30F show the spherical aberration, astigmatism, and distortion, respectively, of Embodiment 3 of the present invention when focused at the near point on the object side. As shown in FIGS. 30A-30C and FIGS. 30D-30F, in Embodiment 3 these aberrations are favorably corrected.

EMBODIMENT 4

Figure 4:
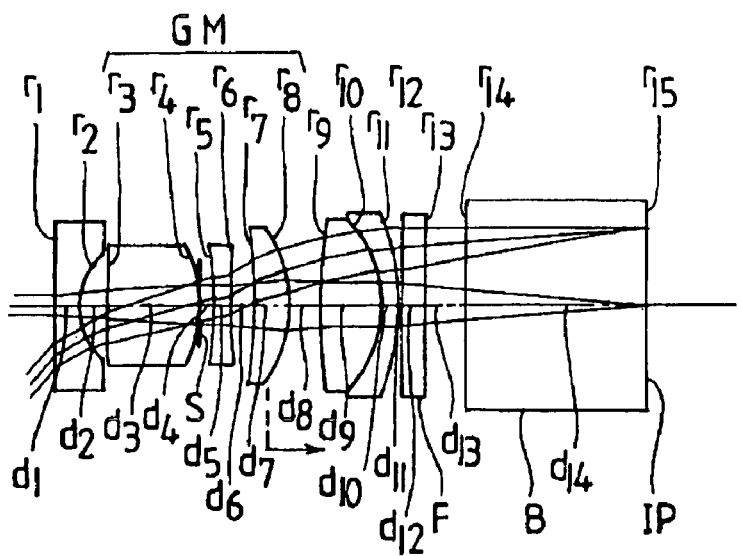
FIG. 4 is a cross-sectional view of Embodiment 4 of the present invention focused at the far point on the object side.

FIG. 4 shows a cross-sectional view of the objective optical system for an endoscope of Embodiment 4 of the present invention. Table 4 below lists the various data explained above for Embodiment 4.

TABLE 4

| Far point focused state | | | |
|---|---|---|---|
| WD = 46 | $f_{TF}$ = 1.830 | $F_{NO}$ = 4.50 | 2 ω = 98.6° |
| | Near point focused state | | |
| WD = 23 | $f_{TN}$ = 1.736 | $F_{NO}$ = 4.28 | 2 ω = 104.7° |
| $r_1$ = ∞ | $d_1$ = 0.5000 | $n_1$ = 1.76820 | $v_1$ = 71.79 |
| $r_2$ = 1.2738 | $d_2$ = 0.5500 | | |
| $r_3$ = 11.1859 | $d_3$ = 1.8838 | $n_2$ = 1.80100 | $v_2$ = 34.97 |
| $r_4$ = −2.5133(stop) | $d_4$ = 0.3000 | | |
| $r_5$ = −6.3316 | $d_5$ = 0.3000 | $n_3$ = 1.88300 | $v_3$ = 40.76 |
| $r_6$ = 8.3186 | $d_6$ = 0.5000 | | |
| $r_7$ = −9.4262 | $d_7$ = 0.7000 | $n_4$ = 1.72916 | $v_4$ = 54.68 |
| $r_8$ = −2.3327 | $d_8$ = 0.5713 | | |
| $r_9$ = 14.3039 | $d_9$ = 1.2000 | $n_5$ = 1.72916 | $v_5$ = 54.68 |
| $r_{10}$ = −2.3012 | $d_{10}$ = 0.3000 | $n_6$ = 1.92286 | $v_6$ = 18.90 |
| $r_{11}$ = −4.2482 | $d_{11}$ = 0.1000 | | |
| $r_{12}$ = ∞ | $d_{12}$ = 0.4500 | $n_7$ = 1.51800 | $v_7$ = 75.00 |
| $r_{13}$ = ∞ | $d_{13}$ = 0.8000 | | |
| $r_{14}$ = ∞ | $d_{14}$ = 3.6000 | $n_8$ = 1.48749 | $v_8$ = 70.23 |
| $r_{15}$ = ∞ (image plane) | | | |

| $|f_{UM}/f_{TF}|$ = 2.230 | $f_{U1}/f_{TF}$ = −0.906 | $f_{TN}/f_{TF}$ = 0.949 |
|---|---|---|
| $f_{U1}$ = −1.658 | | $f_{U1}/f_{TF}$ = −0.91 |
| $f_{U2}$ = 2.729 | | $f_{U2}/f_{TF}$ = 1.49 |
| $f_{U3}$ = −4.033 | | $f_{U3}/f_{TF}$ = −2.20 |
| $f_{U4}$ = 4.081 | | $f_{U4}/f_{TF}$ = 2.23 |
| $f_{UR}$ = 5.545 | | $f_{UR}/f_{TF}$ = 3.03 |
| $|f_U (GM GR)|_{min}$ = 1.49 | | $|R (GM, GR)|_{min}$ = 1.26 |
| $n(GR_p) = n_5$ = 1.72916 | | $n(GR_n) = n_6$ = 1.92286 |
| $v(GR_p) = v_5$ = 54.68 | | $v(GR_n) = v_6$ = 18.90 |

As shown in FIG. 4, the optical system of Embodiment 4 is composed of: a front lens group that consists of a first lens component that has negative refractive power and is formed of a single lens element with lens surfaces having radii of curvature $r_1$ and $r_2$; a middle lens group that consists of three lens components, specifically, a second lens element having positive refractive power and radii of curvature $r_3$ and $r_4$, a third lens element having negative refractive power and radii of curvature $r_5$ and $r_6$, and a fourth lens element having positive refractive power and radii of curvature $r_7$ and $r_8$; a rear lens group that consists of a cemented lens component made up of a biconvex lens element cemented to a meniscus lens element having negative refractive power with radii of curvature $r_9$, $r_{10}$, and $r_{11}$; an infrared cutoff filter F with radii of curvature $r_{12}$ and $r_{13}$; and a glass block B, having radii of curvature $r_{14}$ and $r_{15}$, that is arranged on the image-most side of the optical system.

Embodiment 4 is an example of an optical system according to the first and second modes of construction of the present invention described above in which the third lens component in the middle lens group, referenced by "GM" in Table 4 above and in FIG. 4, has negative refractive power. Embodiment 4 is different from Embodiment 3 in that the fourth lens component having positive refractive power is the lens component that is moved for focusing. Thus, if the middle lens group having this basic optical power arrangement is constructed to have aberration correcting ability, the optical system of the present invention can be simply realized by ensuring a space for movement of the moving lens component even if the fourth lens component is the moving lens component, as in Embodiment 4. In Embodiment 4, the fourth lens component is moved toward the image side during focusing from the far point to the near point on the object side.

Embodiment 4 of the present invention also satisfies Conditions (1) through (7) above, as shown by Table 4 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. As described above, the refractive indices $n(GR_p)$ and $n(GR_n)$ and the Abbe numbers $v(GR_p)$ and $v(GR_n)$ of the lens materials of the cemented lens component that is the last lens component of the rear lens group also satisfy the applicable conditions and design criteria of the present invention.

Figure 31A:
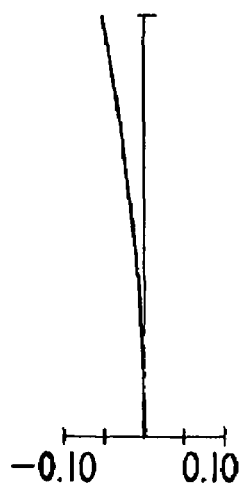
FIGS. 31A-31C show the spherical aberration, astigmatism, and distortion, respectively, of Embodiment 4 of the present invention when focused at the far point on the object side, and and FIGS. 31D-31F show the spherical aberration, astigmatism, and distortion, respectively, of Embodiment 4 of the present invention when focused at the near point on the object side.
Figure 31B:
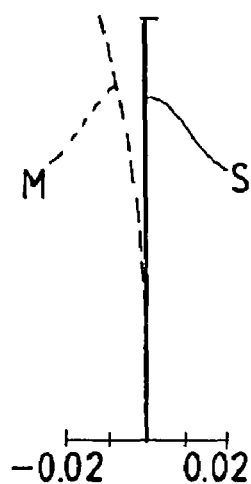
Figure 31C:
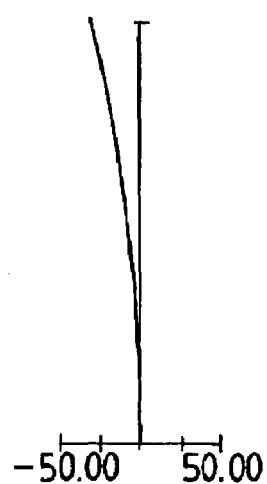
Figure 31D:
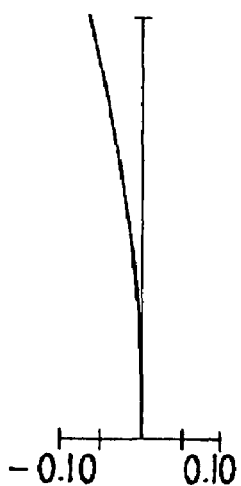
Figure 31E:
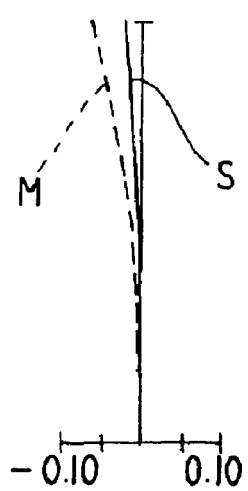
Figure 31F:
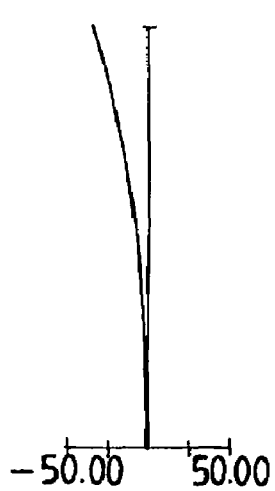

FIGS. 31A-31C show the spherical aberration, astigmatism, and distortion, respectively, of Embodiment 4 of the present invention when focused at the far point on the object side, and FIGS. 31D-31F show the spherical aberration, astigmatism, and distortion, respectively, of Embodiment 4 of the present invention when focused at the near point on the object side. As shown in FIGS. 31A-31C and FIGS. 31D-31F, in Embodiment 4 these aberrations are favorably corrected.

EMBODIMENT 5

Figure 5:
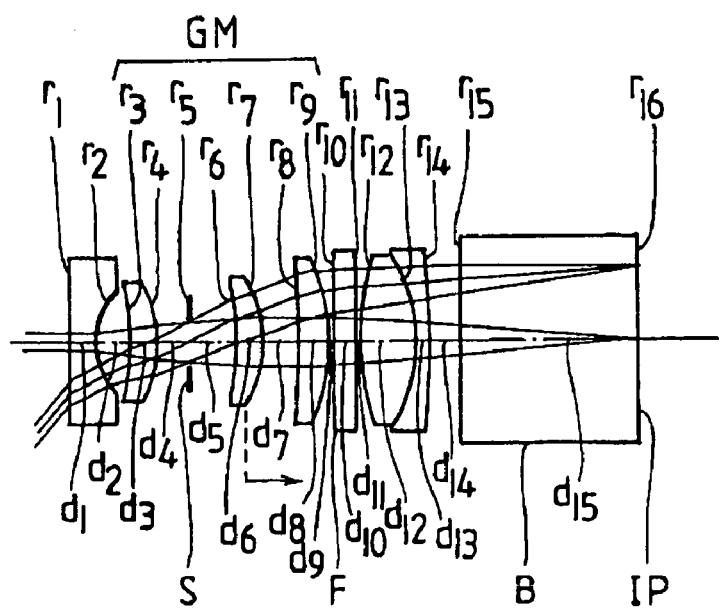
FIG. 5 is a cross-sectional view of Embodiment 5 of the present invention focused at the far point on the object side.

FIG. 5 shows a cross-sectional view of the objective optical system for an endoscope of Embodiment 5 of the present invention. Table 5 below lists the various data explained above for Embodiment 5.

TABLE 5

| Far point focused state | | | |
|---|---|---|---|
| WD = 46 | $f_{TF}$ = 1.820 | $F_{NO}$ = 4.50 | 2 ω = 98.6° |
| | Near point focused state | | |
| WD = 23 | $f_{TN}$ = 1.757 | $F_{NO}$ = 4.37 | 2 ω = 101.8° |
| $r_1$ = ∞ | $d_1$ = 0.5000 | $n_1$ = 1.76820 | $v_1$ = 71.79 |
| $r_2$ = 1.3763 | $d_2$ = 0.7000 | | |
| $r_3$ = −4.9953 | $d_3$ = 0.5380 | $n_2$ = 1.75500 | $v_2$ = 52.32 |
| $r_4$ = −2.6223 | $d_4$ = 0.6894 | | |
| $r_5$ = ∞ (stop) | $d_5$ = 0.9027 | | |
| $r_6$ = −5.3414 | $d_6$ = 0.5000 | $n_3$ = 1.48749 | $v_3$ = 70.23 |
| $r_7$ = −2.4247 | $d_7$ = 0.7196 | | |
| $r_8$ = −18.7123 | $d_8$ = 0.6000 | $n_4$ = 1.88300 | $v_4$ = 40.76 |
| $r_9$ = −3.7651 | $d_9$ = 0.1009 | | |
| $r_{10}$ = ∞ | $d_{10}$ = 0.4500 | $n_5$ = 1.51800 | $v_5$ = 75.00 |
| $r_{11}$ = ∞ | $d_{11}$ = 0.1000 | | |
| $r_{12}$ = 5.2090 | $d_{12}$ = 1.1000 | $n_6$ = 1.58913 | $v_6$ = 61.14 |

TABLE 5-continued

| | | | |
|---|---|---|---|
| $r_{13} = -3.000$ | $d_{13} = 0.3000$ | $n_7 = 1.92286$ | $v_7 = 18.90$ |
| $r_{14} = -16.4746$ | $d_{14} = 0.6000$ | | |
| $r_{15} = \infty$ | $d_{15} = 3.6000$ | $n_8 = 1.48749$ | $v_8 = 70.23$ |
| $r_{16} = \infty$ (image plane) | | | |

| $|f_{UM}/f_{TF}| = 4.738$ | $f_{U1}/f_{TF} = -0.985$ | $f_{TN}/f_{TF} = 0.965$ |
|---|---|---|
| $f_{U1} = -1.792$ | $f_{U1}/f_{TF} = -0.98$ | |
| $f_{U2} = 6.662$ | $f_{U2}/f_{TF} = 3.66$ | |
| $f_{U3} = 8.624$ | $f_{U3}/f_{TF} = 4.74$ | |
| $f_{U4} = 5.239$ | $f_{U4}/f_{TF} = 2.88$ | |
| $f_{UR} = 16.102$ | $f_{UR}/f_{TF} = 8.85$ | |
| $|f_U (GM, GR)|_{min} = 2.88$ | $|R (GM, GR)|_{min} = 1.33$ | |
| $n(GR_p) = n_6 = 1.58913$ | $n(GR_n) = n_7 = 1.92286$ | |
| $v(GR_p) = v_6 = 61.14$ | $v(GR_n) = v_7 = 18.90$ | |

The optical system of Embodiment 5, as shown in FIG. 5, is composed of: a front lens group that consists of a first lens component that has negative refractive power and is formed of a single lens element with lens surfaces having radii of curvature $r_1$ and $r_2$; a middle lens group that consists of three lens components that are all single lens elements having positive refractive power, specifically, a second lens element having radii of curvature $r_3$ and $r_4$, a third lens element having radii of curvature $r_6$ and $r_7$, and a fourth lens element having radii of curvature $r_8$ and $r_9$; and a rear lens group that consists of a cemented lens component made up of a biconvex lens element cemented to a meniscus lens element having negative refractive power with radii of curvature $r_{12}$, $r_{13}$, and $r_{14}$.

Embodiment 5 is an example of an optical system according to the first and second modes of construction of the present invention described above with regard to the middle lens group, referenced by "GM" in Table 5 above and in FIG. 5, which is composed of three lens components, namely, a second lens component having positive refractive power, a third lens component, and a fourth lens component, in order from the object side. Embodiment 5 is further characterized by arranging a stop S for controlling image brightness and having a radius of curvature $r_5$ between the second lens component and the third lens component of the middle lens group, by arranging an infrared cutoff filter F with radii of curvature $r_{10}$ and $r_{11}$ between the middle lens group and the rear lens group, and by arranging a glass block B on the image-most side of the optical system.

Embodiment 5 is an optical system having a construction similar to that of Embodiment 1 but is different from Embodiment 1 in that the third lens component is used as the lens component that is moved for focusing. Namely, focusing from the far point to the near point is performed by moving the third lens component toward the image side. In this manner, Embodiment 5 has an advantage in relaxing the accuracy of positional control because the extent of the movement for focusing increases. In comparison with Embodiment 1, Embodiment 5 has more space available in the vicinity of the lens component that moves for focusing and thus provides a high degree of freedom in lens frame design.

Embodiment 5 of the present invention satisfies Conditions (1) through (7) above as shown by Table 5 above. The focal lengths $f_U$(GM,GR) of the lens components in the middle lens group and rear lens group and the radii of curvature R(GM, GR) of the lens surfaces of the lens components in the middle lens group and rear lens group also satisfy the applicable conditions and design criteria specified for them. The last lens component in the rear lens group is a cemented lens component, and the refractive indices $n(GR_p)$ and $n(GR_n)$ and the Abbe numbers $v(GR_p)$ and $v(GR_n)$ of the lens materials of that lens component also satisfy the applicable conditions and design criteria of the present invention.

Figure 32A:
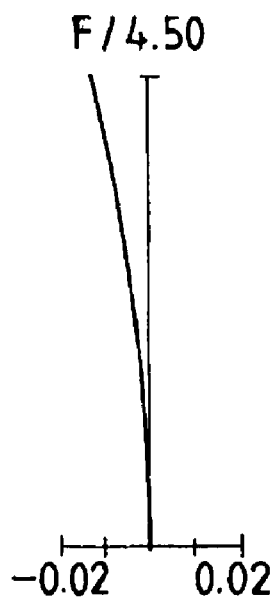
FIGS. 32A-32C show the spherical aberration, astigmatism, and distortion, respectively, of Embodiment 5 of the present invention when focused at the far point on the object side.
Figure 32B:
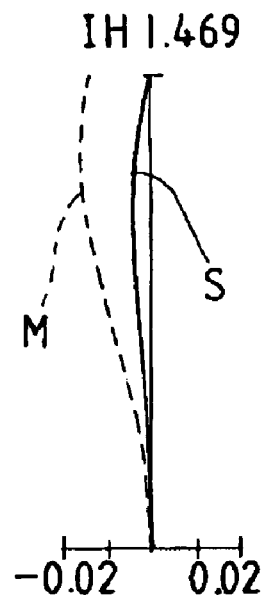
Figure 32C:
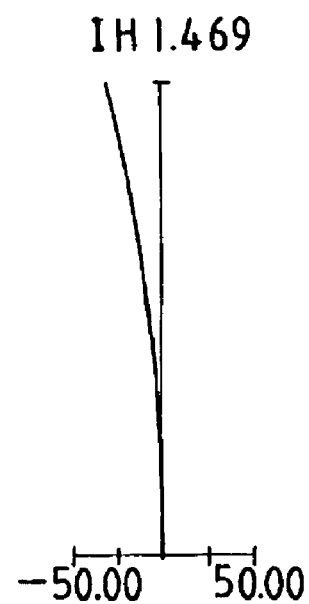
Figure 32D:
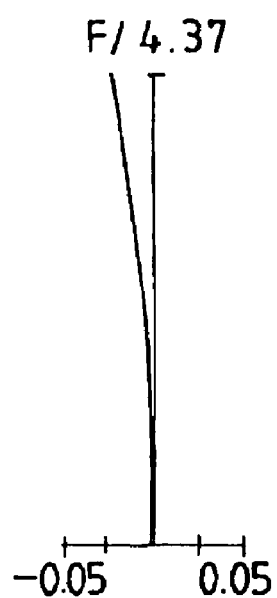
FIGS. 32D-32F show the spherical aberration, astigmatism, and distortion, respectively, of Embodiment 5 of the present invention focused at the near point on the object side.
Figure 32E:
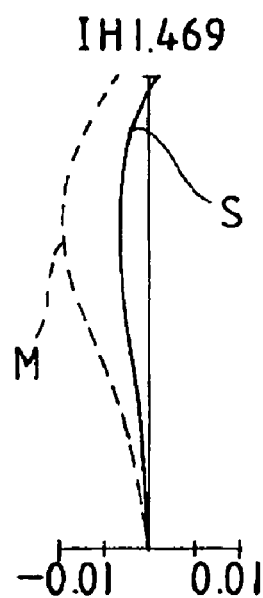
Figure 32F:
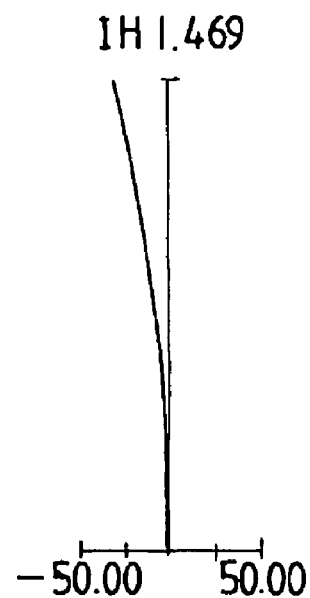

FIGS. 32A-32C show the spherical aberration, astigmatism, and distortion, respectively, of Embodiment 5 of the present invention when focused at the far point on the object side, and FIGS. 32D-32F show the spherical aberration, astigmatism, and distortion, respectively, of Embodiment 5 of the present invention focused at the near point on the object side. As shown in FIGS. 32A-32C and FIGS. 32D-32F, in Embodiment 5 these aberrations are favorably corrected.

EMBODIMENT 6

Figure 6:
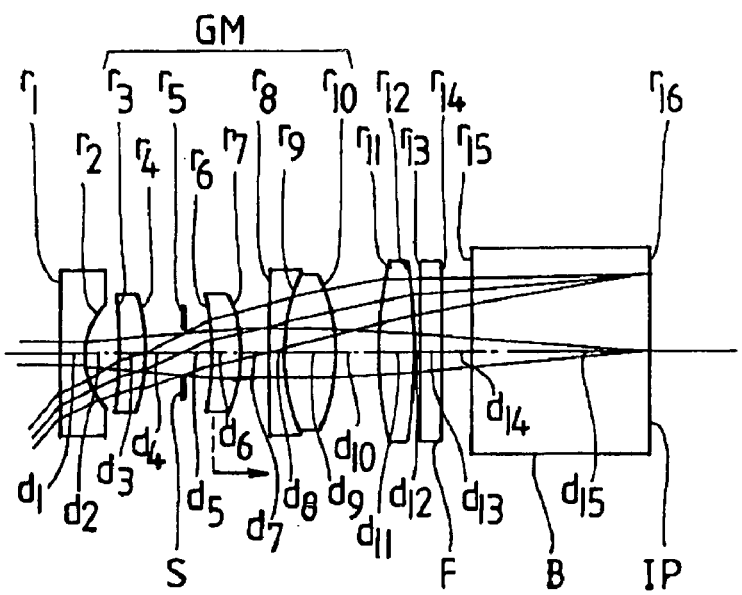
FIG. 6 is a cross-sectional view of Embodiment 6 of the present invention focused at the far point on the object side.

FIG. 6 shows a cross-sectional view of the objective optical system for an endoscope of Embodiment 6 of the present invention. Table 6 below lists the various data explained above for Embodiment 6.

TABLE 6

| Far point focused state | | | |
|---|---|---|---|
| WD = 46 | $f_{TF} = 1.860$ | $F_{NO} = 4.51$ | $2\omega = 98.6°$ |
| Near point focused state | | | |
| WD = 23 | $f_{TN} = 1.796$ | $F_{NO} = 4.38$ | $2\omega = 102.4°$ |
| $r_1 = \infty$ | $d_1 = 0.5000$ | $n_1 = 1.76820$ | $v_1 = 71.79$ |
| $r_2 = 1.2976$ | $d_2 = 0.7000$ | | |
| $r_3 = -7.2654$ | $d_3 = 0.5000$ | $n_2 = 1.92286$ | $v_2 = 18.90$ |
| $r_4 = -4.0097$ | $d_4 = 0.7990$ | | |
| $r_5 = \infty$(stop) | $d_5 = 0.5113$ | | |
| $r_6 = -6.7995$ | $d_6 = 0.6000$ | $n_3 = 1.80610$ | $v_3 = 40.92$ |
| $r_7 = -2.5325$ | $d_7 = 0.5223$ | | |
| $r_8 = 27.2184$ | $d_8 = 0.3000$ | $n_4 = 1.92286$ | $v_4 = 18.90$ |
| $r_9 = 3.6263$ | $d_9 = 1.0000$ | $n_5 = 1.58913$ | $v_5 = 61.14$ |
| $r_{10} = -3.9081$ | $d_{10} = 0.8635$ | | |
| $r_{11} = 6.4748$ | $d_{11} = 0.7500$ | $n_6 = 1.48749$ | $v_6 = 70.23$ |
| $r_{12} = -12.0116$ | $d_{12} = 0.1000$ | | |
| $r_{13} = \infty$ | $d_{13} = 0.4500$ | $n_7 = 1.51800$ | $v_7 = 75.00$ |
| $r_{14} = \infty$ | $d_{14} = 0.6000$ | | |
| $r_{15} = \infty$ | $d_{15} = 3.6000$ | $n_8 = 1.48749$ | $v_8 = 70.23$ |
| $r_{16} = \infty$ (image plane) | | | |

| $|f_{UM}/f_{TF}| = 2.533$ | $f_{U1}/f_{TF} = -0.908$ | $f_{TN}/f_{TF} = 0.966$ |
|---|---|---|
| $f_{U1} = -1.689$ | $f_{U1}/f_{TF} = -0.91$ | |
| $f_{U2} = 9.031$ | $f_{U2}/f_{TF} = 4.86$ | |
| $f_{U3} = 4.711$ | $f_{U3}/f_{TF} = 2.53$ | |
| $f_{U4} = 10.227$ | $f_{U4}/f_{TF} = 5.55$ | |
| $f_{UR} = 8.746$ | $f_{UR}/f_{TF} = 4.70$ | |
| $|f_U (GM, GR)|_{min} = 2.53$ | $|R (GM, GR)|_{min} = 1.36$ | |

As shown in FIG. 6, the optical system of Embodiment 6 is composed of: a front lens group that consists of a first lens component that has negative refractive power and is formed of a single lens element with lens surfaces having radii of curvature $r_1$ and $r_2$; a middle lens group that consists of three lens components, specifically, a second lens element having positive refractive power and radii of curvature $r_3$ and $r_4$, a third lens element having positive refractive power and radii of curvature $r_6$ and $r_7$, and a fourth lens component that consists of a cemented lens component made up of a meniscus lens element having negative refractive power cemented to a biconvex lens element with radii of curvature $r_8$, $r_9$, and $r_{10}$; and a rear lens group that consists of a lens component that has positive refractive power and is formed of a single lens element with lens surfaces having radii of curvature $r_{11}$ and $r_{12}$.

Embodiment 6 is an example of an optical system according to the first and second modes of construction of the present invention described above with regard to the middle lens group, referenced by "GM" in Table 6 above and in FIG.

6, that is composed of three lens components, namely, a second lens component having positive refractive power, a third lens component, and a cemented fourth lens component having positive refractive power, in order from the object side. The third lens component is moved for focusing. A stop S for controlling image brightness and having a radius of curvature $r_5$ is arranged between the second lens component and the third lens component of the middle lens group, an infrared cutoff filter F with radii of curvature $r_{13}$ and $r_{14}$ is arranged on the image side of the rear lens group, and a glass block B with radii of curvature $r_{15}$ and $r_{16}$ is arranged on the image side of the infrared cutoff filter F.

In Embodiment 6, the fourth lens component, which is in the middle lens group, is a cemented lens component, and the last lens component on the image side of the optical system is a single lens element. Aberrations can be favorably corrected by changing the position of the cemented lens component.

Embodiment 6 of the present invention satisfies Conditions (1) through (7) above, as shown by Table 6 above. The focal lengths $f_U$(GM,GR) of the lens components in the middle lens group and rear lens group and the radii of curvature R(GM, GR) of the lens surfaces of the lens components in the middle lens group and rear lens group also satisfy the applicable conditions and design criteria specified for them.

Figure 33A:
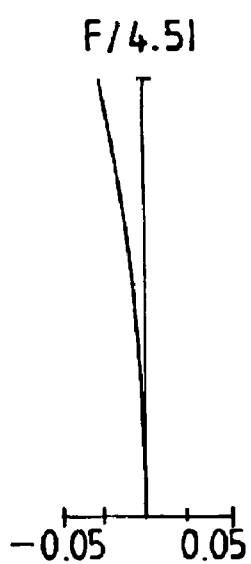
FIGS. 33A-33C show the spherical aberration, astigmatism, and distortion, respectively, of Embodiment 6 of the present invention when focused at the far point on the object side.
Figure 33B:
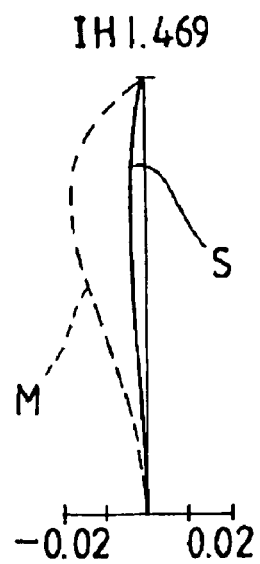
Figure 33C:
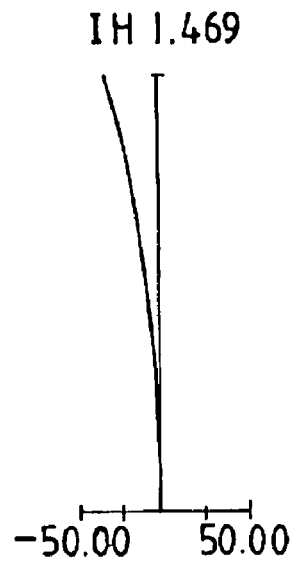
Figure 33D:
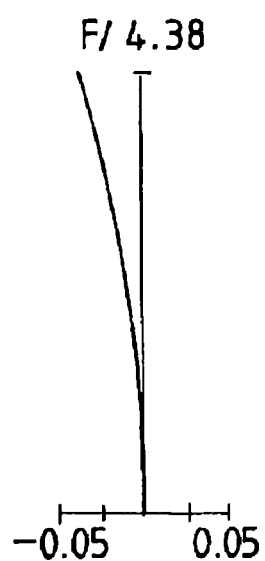
FIGS. 33D-33F show the spherical aberration, astigmatism, and distortion, respectively, of Embodiment 6 of the present invention when focused at the near point on the object side.
Figure 33E:
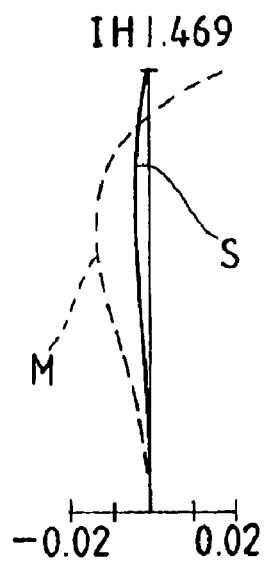
Figure 33F:
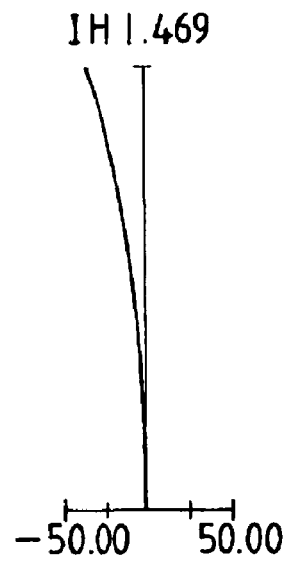

FIGS. 33A-33C show the spherical aberration, astigmatism, and distortion, respectively, of Embodiment 6 of the present invention when focused at the far point on the object side, and FIGS. 33D-33F show the spherical aberration, astigmatism, and distortion, respectively, of Embodiment 6 of the present invention when focused at the near point on the object side. As shown in FIGS. 33A-33C and FIGS. 33D-33F, in Embodiment 6 these aberrations are favorably corrected.

EMBODIMENT 7

Figure 7:
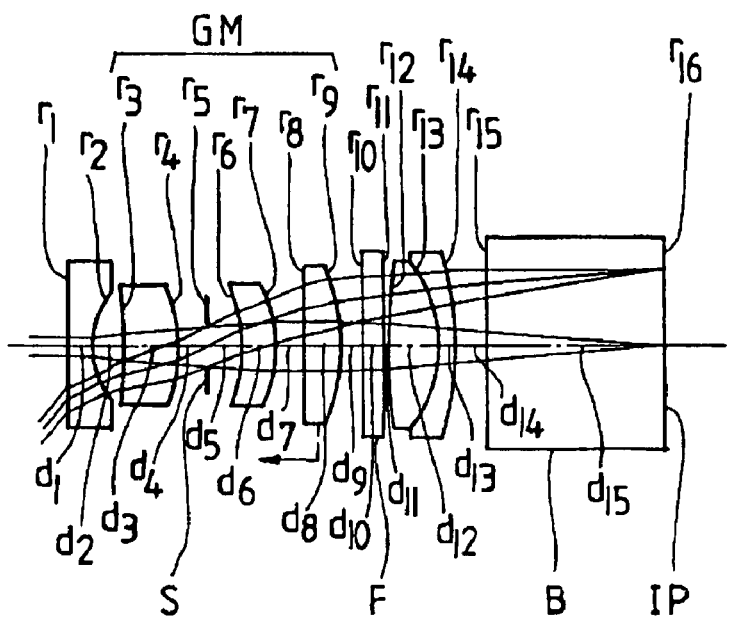
FIG. 7 is a cross-sectional view of Embodiment 7 of the present invention focused at the far point on the object side.

FIG. 7 shows a cross-sectional view of the objective optical system for an endoscope of Embodiment 7 of the present invention. Table 7 below lists the various data explained above for Embodiment 7.

TABLE 7

| Far point focused state | | | |
|---|---|---|---|
| WD = 46 | $f_{TF}$ = 1.812 | $F_{NO}$ = 4.55 | 2ω = 98.6° |
| Near point focused state | | | |
| WD = 23 | $f_{TN}$ = 1.831 | $F_{NO}$ = 4.62 | 2ω = 96.9° |
| $r_1 = \infty$ | $d_1$ = 0.5000 | $n_1$ = 1.76820 | $v_1$ = 71.79 |
| $r_2$ = 1.4371 | $d_2$ = 0.6000 | | |
| $r_3$ = −9.4820 | $d_3$ = 1.1127 | $n_2$ = 1.71999 | $v_2$ = 50.23 |
| $r_4$ = −3.0640 | $d_4$ = 0.5702 | | |
| $r_5 = \infty$ (stop) | $d_5$ = 0.6884 | | |
| $r_6$ = −2.9713 | $d_6$ = 0.6500 | $n_3$ = 1.72916 | $v_3$ = 54.68 |
| $r_7$ = −2.4754 | $d_7$ = 0.5269 | | |
| $r_8 = \infty$ | $d_8$ = 0.7000 | $n_4$ = 1.72916 | $v_4$ = 54.68 |
| $r_9$ = −3.6979 | $d_9$ = 0.4000 | | |
| $r_{10} = \infty$ | $d_{10}$ = 0.4500 | $n_5$ = 1.51800 | $v_5$ = 75.00 |
| $r_{11} = \infty$ | $d_{11}$ = 0.1000 | | |
| $r_{12}$ = 10.1461 | $d_{12}$ = 1.0000 | $n_6$ = 1.58913 | $v_6$ = 61.14 |
| $r_{13}$ = −2.4500 | $d_{13}$ = 0.3000 | $n_7$ = 1.92286 | $v_7$ = 18.90 |
| $r_{14}$ = −5.9718 | $d_{14}$ = 0.6000 | | |
| $r_{15} = \infty$ | $d_{15}$ = 3.6000 | $n_8$ = 1.48749 | $v_8$ = 70.23 |
| $r_{16} = \infty$ (image plane) | | | |
| $|f_{UM}/f_{TF}|$ = 2.799 | $f_{U1}/f_{TF}$ = −1.033 | $f_{TN}/f_{TF}$ = 1.010 | |
| $f_{U1}$ = −1.871 | | $f_{U1}/f_{TF}$ = −1.03 | |
| $f_{U2}$ = 5.862 | | $f_{U2}/f_{TF}$ = 3.24 | |
| $f_{U3}$ = 13.101 | | $f_{U3}/f_{TF}$ = 7.23 | |
| $f_{U4}$ = 5.072 | | $f_{U4}/f_{TF}$ = 2.80 | |

TABLE 7-continued

| $f_{UR}$ = 12.907 | $f_{UR}/f_{TF}$ = 7.12 |
|---|---|
| $|f_U$ (GM, GR)$|_{min}$ = 2.80 | $|R$ (GM, GR)$|_{min}$ = 1.35 |
| $n(GR_p) = n_6$ = 1.58913 | $n(GR_n) = n_7$ = 1.92286 |
| $v(GR_p) = v_6$ = 61.14 | $v(GR_n) = v_7$ = 18.90 |

As shown in FIG. 7, the optical system of Embodiment 7 is composed of: a front lens group that consists of a first lens component that has negative refractive power and is formed of a single lens element with lens surfaces having radii of curvature $r_1$ and $r_2$; a middle lens group that consists of three lens components that are all single lens elements having positive refractive power, specifically, a second lens element having radii of curvature $r_3$ and $r_4$, a third lens element having radii of curvature $r_6$ and $r_7$, and a fourth lens element having radii of curvature $r_8$ and $r_9$; and a rear lens group that consists of a cemented lens component made up of a biconvex lens element cemented to a meniscus lens element having negative refractive power with radii of curvature $r_{12}$, $r_{13}$, and $r_{14}$. Embodiment 7 is an example of an optical system according to the first and second modes of construction of the present invention described above with regard to the middle lens group, referenced by "GM" in Table 7 above and in FIG. 7, and is composed of three lens components, namely, a second lens component having positive refractive power, a third lens component, and a fourth lens component, in order from the object side. A stop S for controlling image brightness is arranged between the second lens component and the third lens component in the middle lens group. An infrared cutoff filter F is arranged between the fourth lens component and the rear or image-side lens component, and a glass block B, having radii of curvature $r_{15}$ and $r_{16}$, is arranged on the image side of the rear lens component.

Embodiment 7 is of a construction similar to Embodiments 1 and 5 described above but is different from them in that the fourth lens component is used as the lens component that is moved for focusing, and near point focusing is performed by moving the fourth lens component toward the object side.

Embodiment 7 of the present invention satisfies Conditions (1) through (7) above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. As described above, the last lens component is a cemented lens component, and the refractive indices $n(GR_p)$ and $n(GR_n)$ and the Abbe numbers $v(GR_p)$ and $v(GR_n)$ of the lens materials of that lens component also satisfy the applicable conditions and design criteria of the present invention.

Figure 34A:
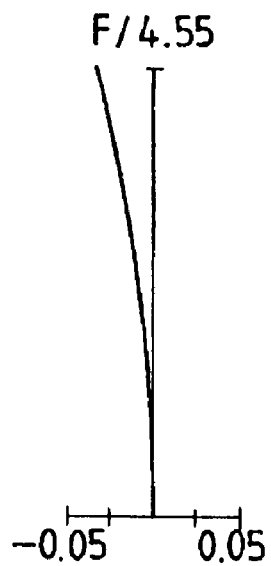
FIGS. 34A-34C show the spherical aberration, astigmatism, and distortion, respectively, of Embodiment 7 of the present invention when focused at the far point on the object side.
Figure 34B:
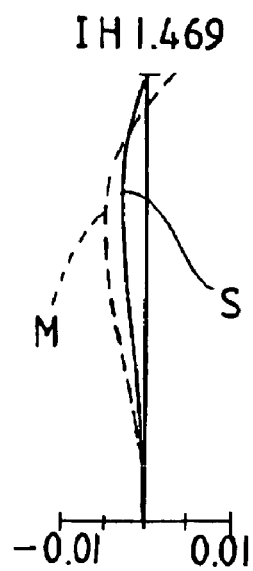
Figure 34C:
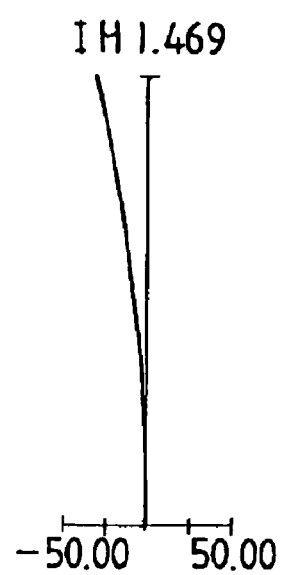
Figure 34D:
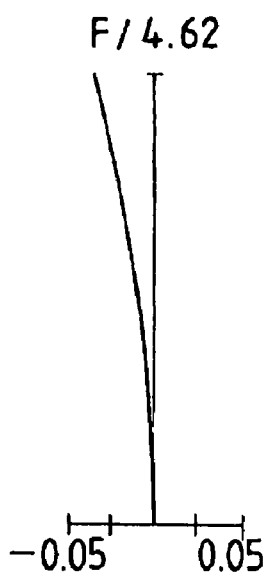
FIGS. 34D-34F show the spherical aberration, astigmatism, and distortion, respectively, of Embodiment 7 of the present invention when focused at the near point on the object side.
Figure 34E:
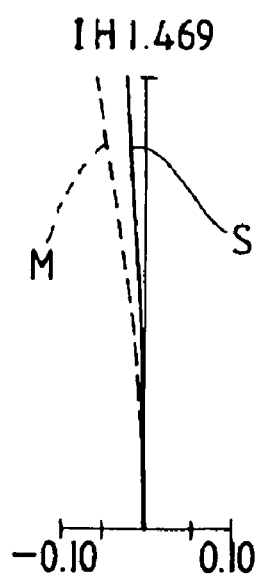
Figure 34F:
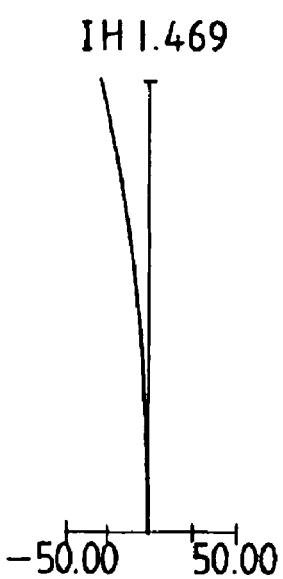

FIGS. 34A-34C show the spherical aberration, astigmatism, and distortion, respectively, of Embodiment 7 of the present invention when focused at the far point on the object side, and FIGS. 34D-34F show the spherical aberration, astigmatism, and distortion, respectively, of Embodiment 7 of the present invention when focused at the near point on the object. As shown in FIGS. 34A-34C and FIGS. 34D-34F, in Embodiment 7 these aberrations are favorably corrected.

EMBODIMENT 8

Figure 8:
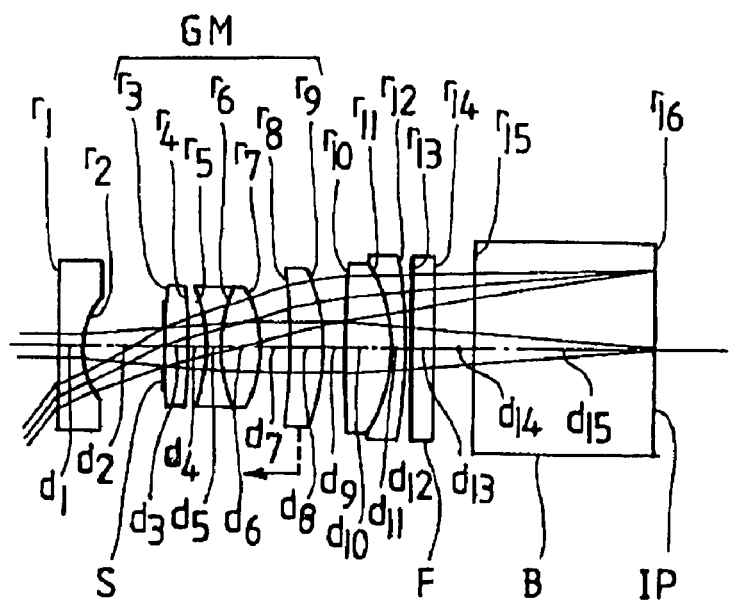
FIG. 8 is a cross-sectional view of Embodiment 8 of the present invention focused at the far point on the object side.

FIG. 8 shows a cross-sectional view of the objective optical system for an endoscope of Embodiment 8 of the present invention. Table 8 below lists the various data explained above for Embodiment 8.

TABLE 8

| Far point focused state | | | |
|---|---|---|---|
| WD = 46 | $f_{TF} = 1.866$ | $F_{NO} = 4.51$ | $2\omega = 98.6°$ |
| | Near point focused state | | |
| WD = 23 | $f_{TN} = 1.881$ | $F_{NO} = 4.57$ | $2\omega = 97.0°$ |

| | | | |
|---|---|---|---|
| $r_1 = \infty$ | $d_1 = 0.5000$ | $n_1 = 1.76820$ | $\nu_1 = 71.79$ |
| $r_2 = 1.5056$ | $d_2 = 1.5826$ | | |
| $r_3 = 7.9079$ (stop) | $d_3 = 0.5000$ | $n_2 = 1.84666$ | $\nu_2 = 23.78$ |
| $r_4 = -7.9079$ | $d_4 = 0.3363$ | | |
| $r_5 = -3.4604$ | $d_5 = 0.3000$ | $n_3 = 1.88300$ | $\nu_3 = 40.76$ |
| $r_6 = 2.9554$ | $d_6 = 0.7500$ | $n_4 = 1.72916$ | $\nu_4 = 54.68$ |
| $r_7 = -2.3002$ | $d_7 = 0.5674$ | | |
| $r_8 = -17.0326$ | $d_8 = 0.6500$ | $n_5 = 1.72916$ | $\nu_5 = 54.68$ |
| $r_9 = -4.0141$ | $d_9 = 0.4000$ | | |
| $r_{10} = 13.8240$ | $d_{10} = 0.9200$ | $n_6 = 1.75500$ | $\nu_6 = 52.32$ |
| $r_{11} = -3.1803$ | $d_{11} = 0.3000$ | $n_7 = 1.92286$ | $\nu_7 = 18.90$ |
| $r_{12} = -10.7425$ | $d_{12} = 0.1000$ | | |
| $r_{13} = \infty$ | $d_{13} = 0.4500$ | $n_8 = 1.51800$ | $\nu_8 = 75.00$ |
| $r_{14} = \infty$ | $d_{14} = 0.8000$ | | |
| $r_{15} = \infty$ | $d_{15} = 3.6000$ | $n_9 = 1.48749$ | $\nu_9 = 70.23$ |
| $r_{16} = \infty$ (image plane) | | | |

| $|f_{UM}/f_{TF}| = 3.780$ | $f_{U1}/f_{TF} = -1.050$ | $f_{TN}/f_{TF} = 1.008$ |
|---|---|---|

| | |
|---|---|
| $f_{U1} = -1.960$ | $f_{U1}/f_{TF} = -1.05$ |
| $f_{U2} = 4.739$ | $f_{U2}/f_{TF} = 2.54$ |
| $f_{U3} = 15.857$ | $f_{U3}/f_{TF} = 8.50$ |
| $f_{U4} = 7.054$ | $f_{U4}/f_{TF} = 3.78$ |
| $f_{UR} = 11.528$ | $f_{UR}/f_{TF} = 6.18$ |
| $|f_U (GM, GR)|_{min} = 2.54$ | $|R (GM, GR)|_{min} = 1.23$ |
| $n(GR_p) = n_6 = 1.75500$ | $n(GR_n) = n_7 = 1.92286$ |
| $\nu(GR_p) = \nu_6 = 52.32$ | $\nu(GR_n) = \nu_7 = 18.90$ |

As shown in FIG. 8, the optical system of Embodiment 8 is composed of: a front lens group that consists of a first lens component that has negative refractive power and is formed of a single lens element with lens surfaces having radii of curvature $r_1$ and $r_2$; a middle lens group that consists of three lens components, specifically, a second lens component formed as a single lens element having positive refractive power and radii of curvature $r_3$ and $r_4$, a cemented third lens component composed of a biconcave lens element cemented to a biconvex lens element and having radii of curvature $r_5$, $r_6$, and $r_7$, and a fourth lens component formed as a single lens element having positive refractive power and radii of curvature $r_8$ and $r_9$; and a rear lens group that consists of a cemented lens component made up of a biconvex lens element cemented to a meniscus lens element having negative refractive power with radii of curvature $r_{10}$, $r_{11}$, and $r_{12}$ Embodiment 8 is an example of an optical system according to the first and second modes of construction of the present invention described above with regard to the middle lens group, referenced by "GM" in Table 8 above and in FIG. 8, being composed of second, third, and fourth lens components having positive refractive power. A stop S for controlling image brightness is positioned on the object side of the second lens component. An infrared cutoff filter F, having radii of curvature $r_{13}$ and $r_{14}$, and a glass block B, having radii of curvature $r_{15}$ and $r_{16}$, are arranged on the image side of the rear lens component.

In Embodiments 1 through 7 described above, the stop S for controlling image brightness is arranged between the second and third lens components in contrast to Embodiment 8 where the stop S is arranged at the object-side surface of the second lens component. This has the advantage that a space can be provided between the first lens component and the second lens component for placement of a light directing prism to redirect the field of view to the side.

Embodiment 8 of the present invention satisfies Conditions (1) through (7) above, as shown by Table 8 above. The focal lengths $f_U$(GM,GR) of the lens components in the middle lens group and rear lens group and the radii of curvature R(GM, GR) of the lens surfaces of the lens components in the middle lens group and rear lens group also satisfy the applicable conditions and design criteria specified for them. As described above, the refractive indices $n(GR_p)$ and $n(GR_n)$ and the Abbe numbers $\nu(GR_p)$ and $\nu(GR_n)$ of the lens materials of the cemented lens component that is the last lens component in the rear lens group also satisfy the applicable conditions and design criteria of the present invention.

Figure 35A:
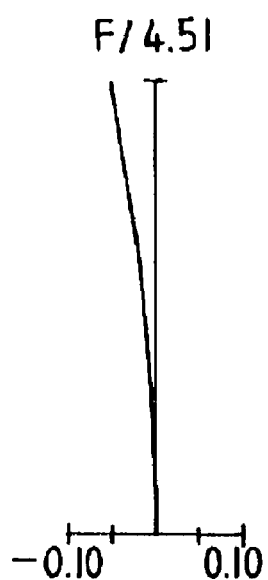
FIGS. 35A-35C show the spherical aberration, astigmatism, and distortion, respectively, of Embodiment 8 of the present invention when focused at the far point on the object side.
Figure 35B:
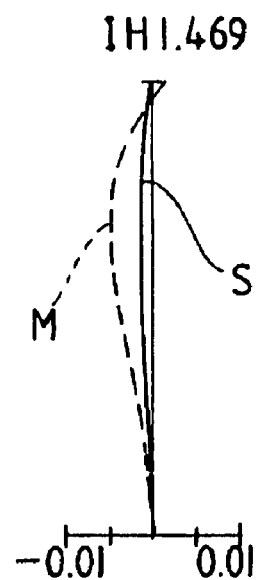
Figure 35C:
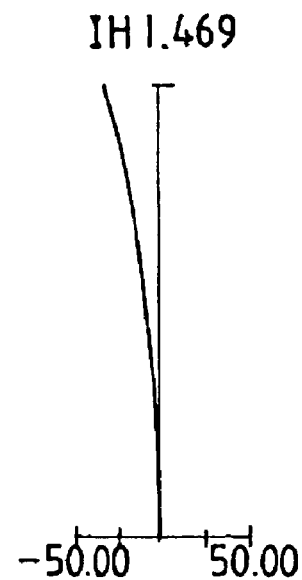
Figure 35D:
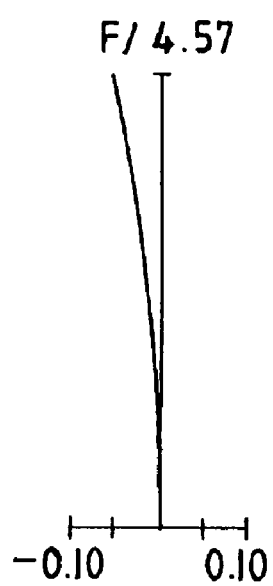
FIGS. 35D-35F show the spherical aberration, astigmatism, and distortion, respectively, of Embodiment 8 of the present invention when focused at the near point on the object side.
Figure 35E:
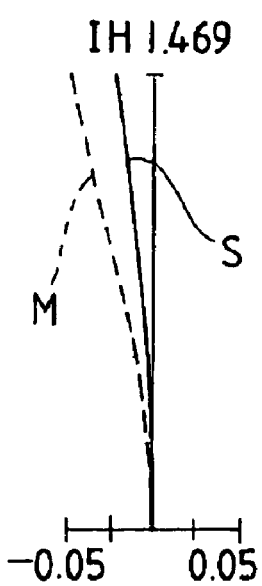
Figure 35F:
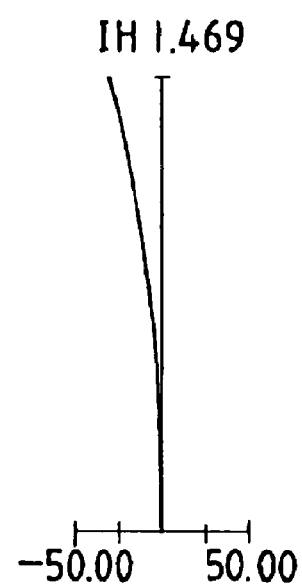

FIGS. 35A-35C show the spherical aberration, astigmatism, and distortion, respectively, of Embodiment 8 of the present invention when focused at the far point on the object side, and FIGS. 35D-35F show the spherical aberration, astigmatism, and distortion, respectively, of Embodiment 8 of the present invention when focused at the near point on the object side. As shown in FIGS. 35A-35C and FIGS. 35D-35F, in Embodiment 8 these aberrations are favorably corrected.

EMBODIMENT 9

Figure 9:
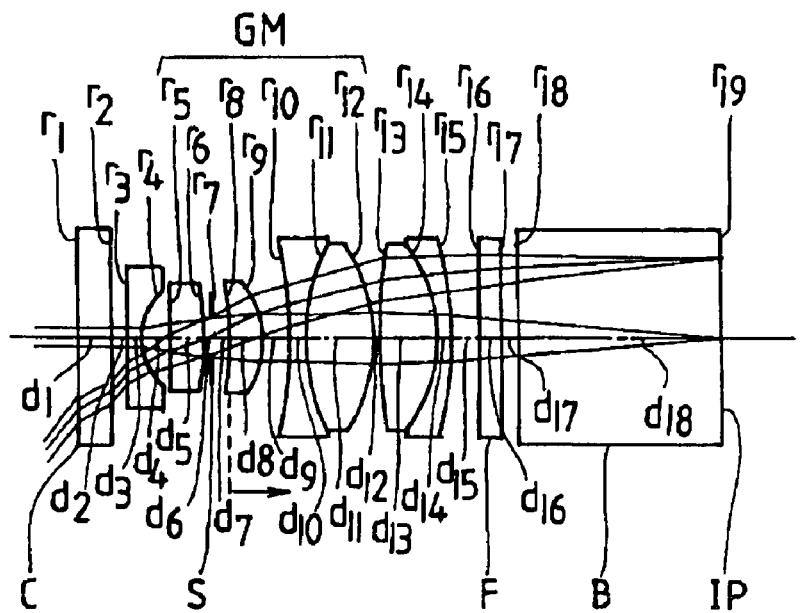
FIG. 9 is a cross-sectional view of Embodiment 9 of the present invention focused at the far point on the object side.

FIG. 9 shows a cross-sectional view of the objective optical system for an endoscope of Embodiment 9 of the present invention. Table 9 below lists the various data explained above for Embodiment 9.

TABLE 9

| Far point focused state | | | |
|---|---|---|---|
| WD = 47 | $f_{TF} = 1.760$ | $F_{NO} = 4.49$ | $2\omega = 103.6°$ |
| | Near point focused state | | |
| WD = 23 | $f_{TN} = 1.710$ | $F_{NO} = 4.37$ | $2\omega = 106.8°$ |

| | | | |
|---|---|---|---|
| $r_1 = \infty$ | $d_1 = 0.7000$ | $n_1 = 1.76820$ | $\nu_1 = 71.79$ |
| $r_2 = \infty$ | $d_2 = 0.2900$ | | |
| $r_3 = 22.2791$ | $d_3 = 0.3000$ | $n_2 = 1.88300$ | $\nu_2 = 40.76$ |
| $r_4 = 1.1037$ | $d_4 = 0.5000$ | | |
| $r_5 = \infty$ | $d_5 = 0.6965$ | $n_3 = 1.92286$ | $\nu_3 = 18.90$ |
| $r_6 = -4.7015$ | $d_6 = 0.1000$ | | |
| $r_7 = \infty$ (stop) | $d_7 = 0.3921$ | | |
| $r_8 = -4.5000$ | $d_8 = 0.6500$ | $n_4 = 1.48749$ | $\nu_4 = 70.23$ |
| $r_9 = -1.6095$ | $d_9 = 0.4834$ | | |
| $r_{10} = -8.1470$ | $d_{10} = 0.3000$ | $n_5 = 1.88300$ | $\nu_5 = 40.76$ |
| $r_{11} = 3.7013$ | $d_{11} = 1.3200$ | $n_6 = 1.71999$ | $\nu_6 = 50.23$ |
| $r_{12} = -3.1017$ | $d_{12} = 0.1000$ | | |
| $r_{13} = 8.5390$ | $d_{13} = 1.1500$ | $n_7 = 1.71999$ | $\nu_7 = 50.23$ |
| $r_{14} = -2.7302$ | $d_{14} = 0.3000$ | $n_8 = 1.92286$ | $\nu_8 = 18.90$ |
| $r_{15} = -6.7728$ | $d_{15} = 0.4788$ | | |
| $r_{16} = \infty$ | $d_{16} = 0.4500$ | $n_9 = 1.51800$ | $\nu_9 = 75.00$ |
| $r_{17} = \infty$ | $d_{17} = 0.3000$ | | |
| $r_{18} = \infty$ | $d_{18} = 3.9000$ | $n_{10} = 1.51633$ | $\nu_{10} = 64.14$ |
| $r_{19} = \infty$ (image plane) | | | |

| $|f_{UM}/f_{TF}| = 2.720$ | $f_{U1}/f_{TF} = -0.752$ | $f_{TN}/f_{TF} = 0.972$ |
|---|---|---|

| | |
|---|---|
| $f_{U1} = -1.324$ | $f_{U1}/f_{TF} = -0.75$ |
| $f_{U2} = 5.095$ | $f_{U2}/f_{TF} = 2.90$ |
| $f_{U3} = 4.787$ | $f_{U3}/f_{TF} = 2.72$ |
| $f_{U4} = 9.071$ | $f_{U4}/f_{TF} = 5.15$ |
| $f_{UR} = 7.019$ | $f_{UR}/f_{TF} = 3.99$ |
| $|f_U (GM, GR)|_{min} = 2.72$ | $|R (GM, GR)|_{min} = 0.91$ |
| $n(GR_p) = n_7 = 1.71999$ | $n(GR_n) = n_8 = 1.92286$ |
| $\nu(GR_p) = \nu_7 = 50.23$ | $\nu(GR_n) = \nu_8 = 18.90$ |

As shown in FIG. 9, the optical system of Embodiment 9 is composed of: a front lens group that consists of a first lens component that has negative refractive power and is formed of a single lens element with lens surfaces having radii of curvature $r_3$ and $r_4$; a middle lens group that consists of three lens components, specifically, a second lens component formed as a single lens element having positive refractive power and radii of curvature $r_5$ and $r_6$, a third lens component formed as a single lens element having positive refractive power and radii of curvature $r_8$ and $r_9$, and a cemented fourth lens component composed of a biconcave lens element cemented to a biconvex lens element and having radii of curvature $r_{10}$, $r_{11}$, and $r_{12}$; and a rear lens group that consists of a cemented lens component formed of a biconvex lens element cemented to a meniscus lens element having negative refractive power with radii of curvature $r_{13}$, $r_{14}$, and $r_{15}$.

Embodiment 9 is an example of an optical system according to the first and second modes of construction of the present invention described above with regard to the middle lens group, referenced by "GM" in Table 9 above and in FIG. 9, being composed of second, third, and fourth lens components having positive refractive power.

Embodiment 9 has a construction in which the fourth lens component, which is in the middle lens group, is a cemented lens component rather than a single lens element, as in Embodiment 5 above. A sapphire plane parallel plate C having radii of curvature $r_1$ and $r_2$ is arranged on the object side of the first lens component and that first lens component is formed as a single lens element having negative refractive power and is made of a glass with a higher refractive index than sapphire. In this manner, when sapphire having birefringence is used as a lens element with optical power as in Embodiments 1 through 8 above, some deterioration of imaging performance due to polarization dependence of refractive power occurs, that is avoided in Embodiment 9. Embodiment 9 has an advantage in that the first lens component does not provide the front surface of the endoscope, thereby providing more freedom in selecting the glass material and bending choices of the first lens component.

In the middle lens group of Embodiment 9, the third lens component is the lens component that is moved for focusing, and the fourth lens component does not move. Therefore, in Embodiment 9, the fourth lens component does not have to be unreasonably miniaturized and may be made to have an outside diameter that is nearly the same as the lens component of the rear lens group.

A stop S for controlling image brightness is positioned on the image side of the second lens component of the middle lens group.

Embodiment 9 of the present invention satisfies Conditions (1) through (7) above, as shown by Table 9 above. The focal lengths $f_U$(GM,GR) of the lens components in the middle lens group and rear lens group and the radii of curvature R(GM, GR) of the lens surfaces of the lens components in the middle lens group and rear lens group also satisfy the applicable conditions and design criteria specified for them.

In Embodiment 9, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

FIGS. 36A-36C show the spherical aberration, astigmatism, and distortion, respectively, of Embodiment 9 of the present invention when focused at the far point on the object side, and FIGS. 36D-36F show the spherical aberration, astigmatism, and distortion, respectively, of Embodiment 9 of the present invention when focused at the near point on the object side. As shown in FIGS. 36A-36C and FIGS. 36D-36F, in Embodiment 9 these aberrations are favorably corrected.

EMBODIMENT 10

Figure 10:
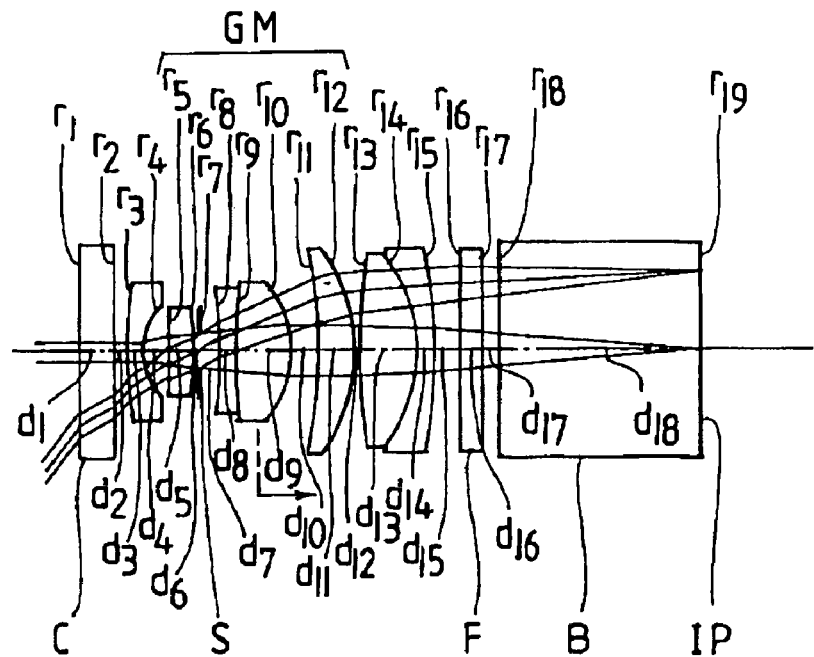
FIG. 10 is a cross-sectional view of Embodiment 10 of the present invention focused at the far point on the object side.

FIG. 10 shows a cross-sectional view of the objective optical system for an endoscope of Embodiment 10 of the present invention. Table 10 below lists the various data explained above for Embodiment 10.

TABLE 10

| Far point focused state | | | |
|---|---|---|---|
| WD = 47 | $f_{TF}$ = 1.760 | $F_{NO}$ = 4.47 | 2 ω = 103.8° |
| Near point focused state | | | |
| WD = 23 | $f_{TN}$ = 1.711 | $F_{NO}$ = 4.36 | 2 ω = 106.4° |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = 12.8863$ | $d_3 = 0.3000$ | $n_2 = 1.88300$ | $v_2 = 40.76$ |
| $r_4 = 1.1823$ | $d_4 = 0.5000$ | | |
| $r_5 = \infty$ | $d_5 = 0.4827$ | $n_3 = 1.92286$ | $v_3 = 18.90$ |
| $r_6 = -5.9310$ | $d_6 = 0.1000$ | | |
| $r_7 = \infty$ (stop) | $d_7 = 0.4140$ | | |
| $r_8 = -6.9710$ | $d_8 = 0.3000$ | $n_4 = 1.88300$ | $v_4 = 40.76$ |
| $r_9 = 10.5719$ | $d_9 = 1.1000$ | $n_5 = 1.51742$ | $v_5 = 52.43$ |
| $r_{10} = -1.8700$ | $d_{10} = 0.4940$ | | |
| $r_{11} = -9.6060$ | $d_{11} = 0.7000$ | $n_6 = 1.83481$ | $v_6 = 42.71$ |
| $r_{12} = -3.3249$ | $d_{12} = 0.1000$ | | |
| $r_{13} = 10.1397$ | $d_{13} = 1.1500$ | $n_7 = 1.72916$ | $v_7 = 54.68$ |
| $r_{14} = -2.7293$ | $d_{14} = 0.3000$ | $n_8 = 1.92286$ | $v_8 = 18.90$ |
| $r_{15} = -9.6856$ | $d_{15} = 0.4908$ | | |
| $r_{16} = \infty$ | $d_{16} = 0.4500$ | $n_9 = 1.51800$ | $v_9 = 75.00$ |
| $r_{17} = \infty$ | $d_{17} = 0.3000$ | | |
| $r_{18} = \infty$ | $d_{18} = 3.9000$ | $n_{10} = 1.51633$ | $v_{10} = 64.14$ |
| $r_{19} = \infty$ (image plane) | | | |
| $|f_{UM}/f_{TF}|$ = 3.718 | $f_{U1}/f_{TF}$ = −0.848 | $f_{TN}/f_{TF}$ = 0.972 | |
| $f_{U1}$ = −1.492 | | $f_{U1}/f_{TF}$ = −0.85 | |
| $f_{U2}$ = 6.427 | | $f_{U2}/f_{TF}$ = 3.65 | |
| $f_{U3}$ = 6.544 | | $f_{U3}/f_{TF}$ = 3.72 | |
| $f_{U4}$ = 5.797 | | $f_{U4}/f_{TF}$ = 3.29 | |
| $f_{UR}$ = 10.527 | | $f_{UR}/f_{TF}$ = 5.98 | |
| $|f_U$ (GM, GR)$|_{min}$ = 3.29 | | $|R$ (GM, GR)$|_{min}$ = 1.06 | |
| $n(GR_p) = n_7 = 1.72916$ | | $n\,GR_n) = n_8 = 1.92286$ | |
| $v(GR_p) = v_7 = 54.68$ | | $v(GR_n) = v_8 = 18.90$ | |

As shown in FIG. 10, the optical system of Embodiment 10 is composed of: a front lens group that consists of a first lens component that has negative refractive power and is formed of a single lens element with lens surfaces having radii of curvature $r_3$ and $r_4$; a middle lens group that consists of three lens components, specifically, a second lens component formed as a single lens element having positive refractive power and radii of curvature $r_5$ and $r_6$, a cemented third lens component composed of a biconcave lens element cemented to a biconvex lens element and having radii of curvature $r_8$, $r_9$, and $r_{10}$, and a fourth lens component formed as a single lens element having positive refractive power and radii of curvature $r_{11}$ and $r_{12}$; and a rear lens group that consists of a cemented lens component formed of a biconvex lens element cemented to a meniscus lens element having negative refractive power with radii of curvature $r_{13}$, $r_{14}$, and $r_{15}$.

Embodiment 10 is an example of an optical system according to the second mode of construction of the present invention described above with regard to the middle lens group, referenced by "GM" in Table 10 above and in FIG. 10, being composed of second, third, and fourth lens components having positive refractive power.

Embodiment 10 has a construction that is similar to Embodiment 9 but in Embodiment 10 the third lens component, which is the lens component that is moved for focusing, is a cemented lens component rather than a single lens component and the fourth lens component is a single lens element rather than a cemented lens component.

Embodiment 10 of the present invention satisfies Conditions (1) through (7) above, as shown by Table 10 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. In Embodiment 10, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 37A:
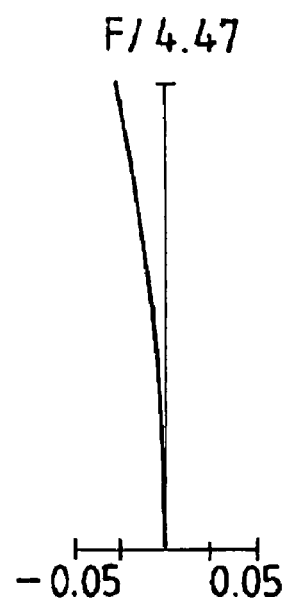
FIGS. 37A-37C show the spherical aberration, astigmatism, and distortion, respectively, of Embodiment 10 of the present invention when focused at the far point on the object side.
Figure 37B:
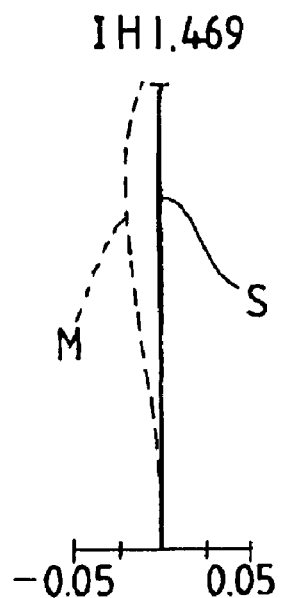
Figure 37C:
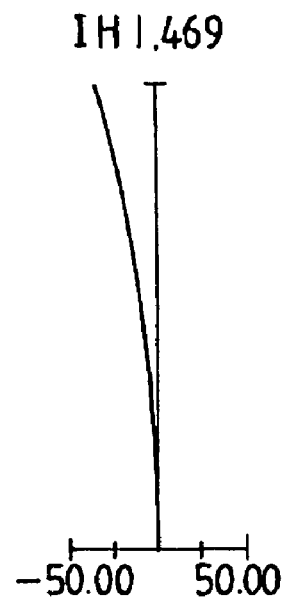
Figure 37D:
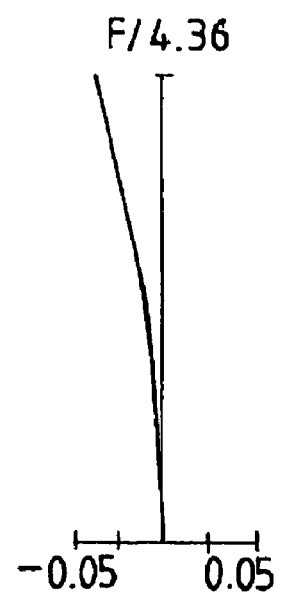
FIGS. 37D-37F show the spherical aberration, astigmatism, and distortion, respectively, of Embodiment 10 of the present invention when focused at the near point on the object side.
Figure 37E:
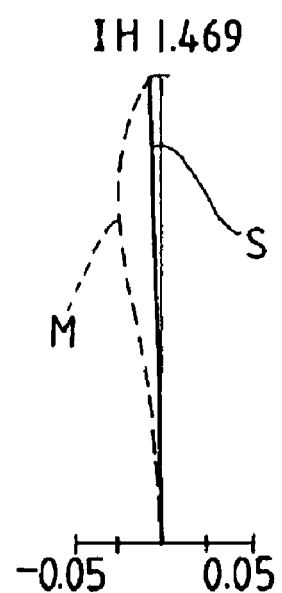
Figure 37F:
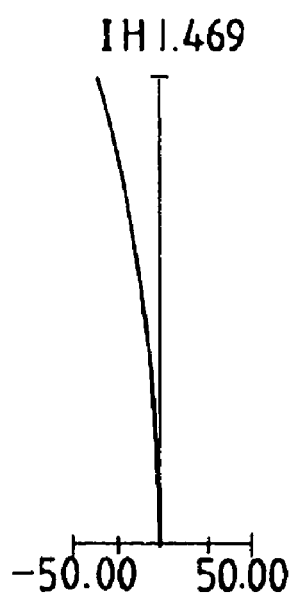

FIGS. 37A-37C show the spherical aberration, astigmatism, and distortion, respectively, of Embodiment 10 of the present invention when focused at the far point on the object side, and FIGS. 37D-37F show the spherical aberration, astigmatism, and distortion, respectively, of Embodiment 10 of the present invention when focused at the near point on the object side. As shown in FIGS. 37A-37C and FIGS. 37D-37F, in Embodiment 10 these aberrations are favorably corrected.

EMBODIMENT 11

Figure 11:
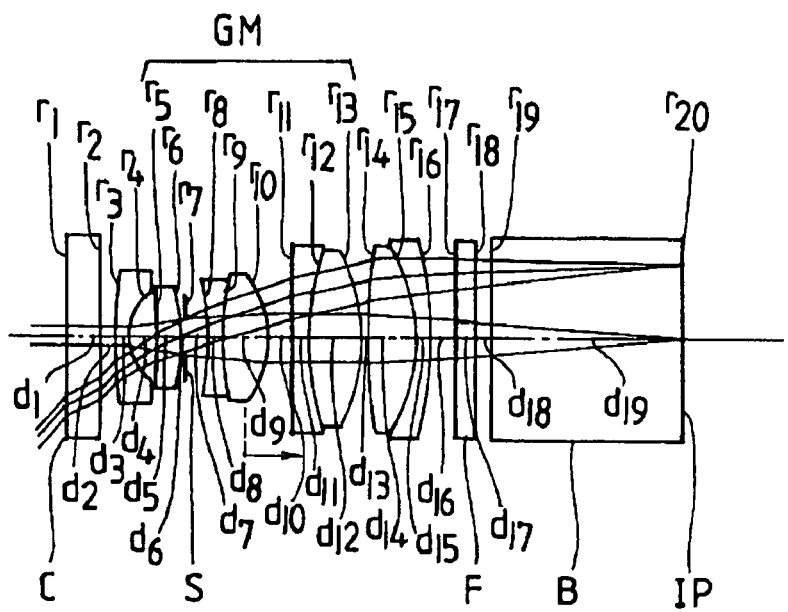
FIG. 11 is a cross-sectional view of Embodiment 11 of the present invention focused at the far point on the object side.

FIG. 11 shows a cross-sectional view of the objective optical system for an endoscope of Embodiment 11 of the present invention. Table 11 below lists the various data explained above for Embodiment 11.

TABLE 11

| Far point focused state | | | |
|---|---|---|---|
| WD = 48 | $f_{TF}$ = 1.750 | $F_{NO}$ = 4.51 | 2 ω = 103.0° |
| Near point focused state | | | |
| WD = 23 | $f_{TN}$ = 1.693 | $F_{NO}$ = 4.37 | 2 ω = 106.3° |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = 11.5644$ | $d_3 = 0.3000$ | $n_2 = 1.88300$ | $v_2 = 40.76$ |
| $r_4 = 1.0748$ | $d_4 = 0.5300$ | | |
| $r_5 = -25.0632$ | $d_5 = 0.5121$ | $n_3 = 1.92286$ | $v_3 = 18.90$ |
| $r_6 = -4.2922$ | $d_6 = 0.1000$ | | |
| $r_7 = \infty$ (stop) | $d_7 = 0.4326$ | | |
| $r_8 = -6.2182$ | $d_8 = 0.3000$ | $n_4 = 1.88300$ | $v_4 = 40.76$ |
| $r_9 = 4.6833$ | $d_9 = 0.9500$ | $n_5 = 1.71999$ | $v_5 = 50.23$ |
| $r_{10} = -1.9693$ | $d_{10} = 0.4823$ | | |
| $r_{11} = -64.8065$ | $d_{11} = 0.3000$ | $n_6 = 1.88300$ | $v_6 = 40.76$ |
| $r_{12} = 4.7301$ | $d_{12} = 1.1000$ | $n_7 = 1.51633$ | $v_7 = 64.14$ |
| $r_{13} = -3.3095$ | $d_{13} = 0.1000$ | | |
| $r_{14} = 9.1534$ | $d_{14} = 1.0500$ | $n_8 = 1.72916$ | $v_8 = 54.68$ |
| $r_{15} = -3.1961$ | $d_{15} = 0.3000$ | $n_9 = 1.92286$ | $v_9 = 18.90$ |
| $r_{16} = -7.4233$ | $d_{16} = 0.4787$ | | |
| $r_{17} = \infty$ | $d_{17} = 0.4500$ | $n_{10} = 1.51800$ | $v_{10} = 75.00$ |
| $r_{18} = \infty$ | $d_{18} = 0.3000$ | | |
| $r_{19} = \infty$ | $d_{19} = 3.9000$ | $n_{11} = 1.51633$ | $v_{11} = 64.14$ |
| $r_{20} = \infty$ (image plane) | | | |

| $|f_{UM}/f_{TF}|$ = 2.462 | $f_{U1}/f_{TF}$ = −0.777 | $f_{TN}/f_{TF}$ = 0.967 |
|---|---|---|
| $f_{U1}$ = −1.360 | | $f_{U1}/f_{TF}$ = −0.78 |
| $f_{U2}$ = 5.546 | | $f_{U2}/f_{TF}$ = 3.17 |
| $f_{U3}$ = 4.308 | | $f_{U3}/f_{TF}$ = 2.46 |
| $f_{U4}$ = 13.267 | | $f_{U4}/f_{TF}$ = 7.58 |
| $f_{UR}$ = 7.150 | | $f_{UR}/f_{TF}$ = 4.09 |
| $|f_U(GM, GR)|_{min}$ = 2.46 | | $|R(GM, GR)|_{min}$ = 1.13 |
| $n(GR_p) = n_8 = 1.72916$ | | $n(GR_n) = n_9 = 1.92286$ |
| $v(GR_p) = v_8 = 54.68$ | | $v(GR_n) = v_9 = 18.90$ |

As shown in FIG. 11, the optical system of Embodiment 11 is composed of: a front lens group that consists of a first lens component that has negative refractive power and is formed of a single lens element with lens surfaces having radii of curvature $r_3$ and $r_4$; a middle lens group that consists of three lens components, specifically, a second lens component formed as a single lens element having positive refractive power and radii of curvature $r_5$ and $r_6$, a cemented third lens component composed of a biconcave lens element cemented to a biconvex lens element and having radii of curvature $r_8$, $r_9$, and $r_{10}$, and a cemented fourth lens component composed of a biconcave lens element cemented to a biconvex lens element and having radii of curvature $r_{11}$, $r_{12}$, and $r_{13}$; and a rear lens group composed of a cemented lens component formed of a biconvex lens element cemented to a meniscus lens element having negative refractive power with radii of curvature $r_{14}$, $r_{15}$, and $r_{16}$.

Embodiment 11 is an example of an optical system with the middle lens group, referenced by "GM" in Table 11 above and in FIG. 11, being composed of second, third, and fourth lens components having positive refractive power, and is in accordance with the first and second modes of construction of the present invention described above. In Embodiment 11, the fourth lens component, which is in the middle lens group, is a cemented lens component rather than a single lens element as in Embodiment 10 above.

In the optical systems of the present invention, the lens component on the image side of the stop S easily becomes a meniscus lens element with a convex surface on the image side. In that case, if that lens component is constructed as a single lens element, it becomes difficult to accurately form the shape of the lens surface. In Embodiment 11, the optical system can be constructed by lens elements with good workability by making the third and fourth lens components, which are in the middle lens group, that easily become meniscus lens elements into cemented lens components.

Similar to Embodiment 2 above, Embodiment 11 is favorable in correcting the field curvature, which is readily overcorrected.

Embodiment 11 of the present invention satisfies Conditions (1) through (7) above, as shown by Table 11 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 11, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 38A:
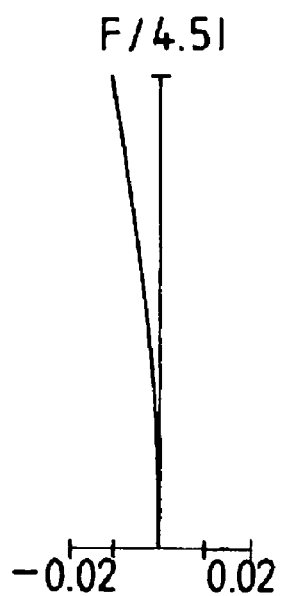
FIGS. 38A-38C show the spherical aberration, astigmatism, and distortion, respectively, of Embodiment 11 of the present invention when focused at the far point on the object side, and and FIGS. 38D-38F show the spherical aberration, astigmatism, and distortion, respectively, of Embodiment 11 of the present invention when focused at the near point on the object side.
Figure 38B:
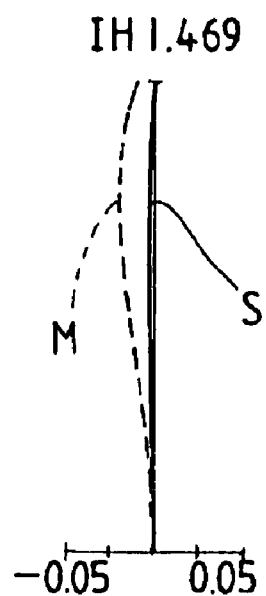
Figure 38C:
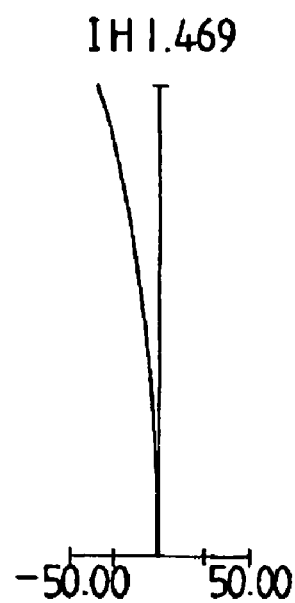
Figure 38D:
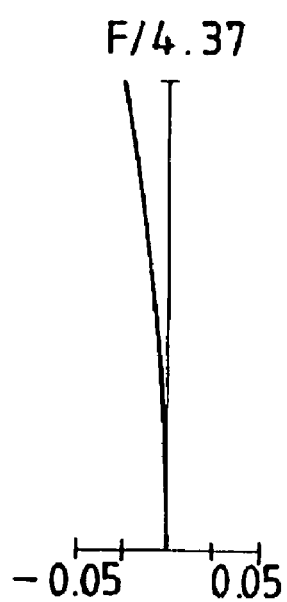
Figure 38E:
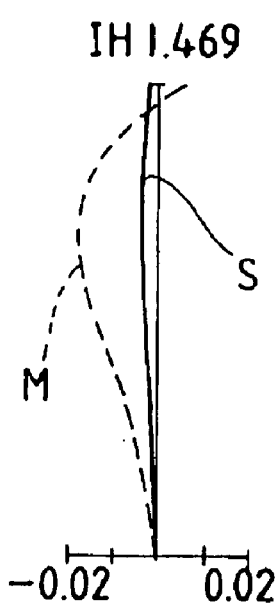
Figure 38F:
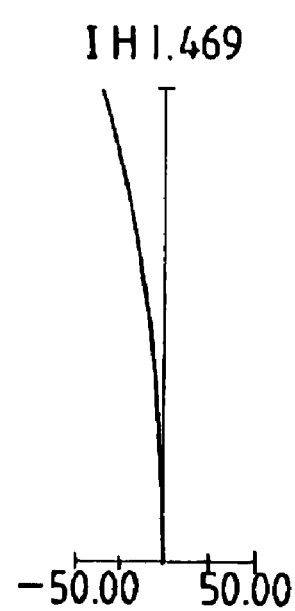

FIGS. 38A-38C show the spherical aberration, astigmatism, and distortion, respectively, of Embodiment 11 of the present invention when focused at the far point on the object side, and FIGS. 38D-38F show the spherical aberration, astigmatism, and distortion, respectively, of Embodiment 11 of the present invention when focused at the near point on the object side. As shown in FIGS. 38A-38C and FIGS. 38D-38F, in Embodiment 11 these aberrations are favorably corrected.

EMBODIMENT 12

Figure 12:
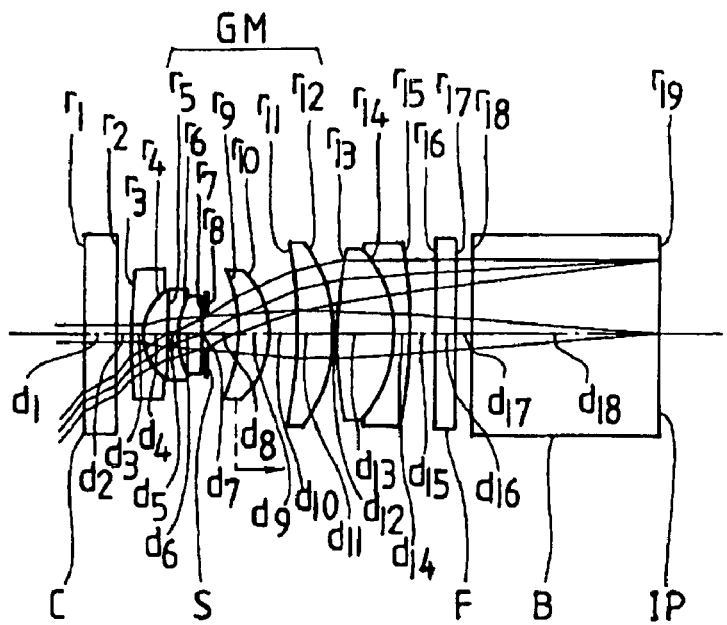
FIG. 12 is a cross-sectional view of Embodiment 12 of the present invention focused at the far point on the object side.

FIG. 12 shows a cross-sectional view of the objective optical system for an endoscope of Embodiment 12 of the present invention. Table 12 below lists the various data explained above for Embodiment 12.

TABLE 12

| Far point focused state | | | |
|---|---|---|---|
| WD = 46 | $f_{TF}$ = 1.760 | $F_{NO}$ = 4.48 | 2 ω = 103.1° |
| | Near point focused state | | |
| WD = 23 | $f_{TN}$ = 1.717 | $F_{NO}$ = 4.38 | 2 ω = 105.3° |
| $r_1 = \infty$ | $d_1$ = 0.7000 | $n_1$ = 1.76820 | $v_1$ = 71.79 |
| $r_2 = \infty$ | $d_2$ = 0.2900 | | |
| $r_3$ = 12.7963 | $d_3$ = 0.3000 | $n_2$ = 1.88300 | $v_2$ = 40.76 |
| $r_4$ = 1.1366 | $d_4$ = 0.4500 | | |
| $r_5$ = 11.9331 | $d_5$ = 0.2500 | $n_3$ = 1.88300 | $v_3$ = 40.76 |
| $r_6$ = 2.0645 | $d_6$ = 0.5000 | $n_4$ = 1.72825 | $v_4$ = 28.46 |
| $r_7$ = −4.4991 | $d_7$ = 0.0500 | | |
| $r_8 = \infty$ (stop) | $d_8$ = 0.6840 | | |
| $r_9$ = −2.7489 | $d_9$ = 0.6200 | $n_5$ = 1.48749 | $v_5$ = 70.23 |
| $r_{10}$ = −1.6745 | $d_{10}$ = 0.5571 | | |
| $r_{11}$ = −8.6245 | $d_{11}$ = 0.7000 | $n_6$ = 1.88300 | $v_6$ = 40.76 |
| $r_{12}$ = −3.2679 | $d_{12}$ = 0.1000 | | |
| $r_{13}$ = 8.9926 | $d_{13}$ = 1.2000 | $n_7$ = 1.72916 | $v_7$ = 54.68 |
| $r_{14}$ = −2.4835 | $d_{14}$ = 0.3000 | $n_8$ = 1.92286 | $v_8$ = 18.90 |
| $r_{15}$ = −7.7750 | $d_{15}$ = 0.4948 | | |
| $r_{16} = \infty$ | $d_{16}$ = 0.4500 | $n_9$ = 1.51800 | $v_9$ = 75.00 |
| $r_{17} = \infty$ | $d_{17}$ = 0.3000 | | |
| $r_{18} = \infty$ | $d_{18}$ = 3.9000 | $n_{10}$ = 1.51633 | $v_{10}$ = 64.14 |
| $r_{19} = \infty$ (image plane) | | | |

| $|f_{UM}/f_{TF}|$ = 4.199 | $f_{U1}/f_{TF}$ = −0.813 | $f_{TN}/f_{TF}$ = 0.976 |
|---|---|---|
| $f_{U1}$ = −1.430 | $f_{U1}/f_{TF}$ = −0.81 | |
| $f_{U2}$ = 6.272 | $f_{U2}/f_{TF}$ = 3.56 | |
| $f_{U3}$ = 7.391 | $f_{U3}/f_{TF}$ = 4.20 | |
| $f_{U4}$ = 5.615 | $f_{U4}/f_{TF}$ = 3.19 | |
| $f_{UR}$ = 8.378 | $f_{UR}/f_{TF}$ = 4.76 | |
| $|f_U (GM, GR)|_{min}$ = 3.19 | $|R (GM, GR)|_{min}$ = 1.16 | |
| $n(GR_p) = n_7$ = 1.72916 | $n(GR_n) = n_8$ = 1.92286 | |
| $v(GR_p) = v_7$ = 54.68 | $v(GR_n) = v_8$ = 18.90 | |

As shown in FIG. 12, the optical system of Embodiment 12 is composed of: a front lens group that consists of a first lens component that has negative refractive power and is formed of a single lens element with lens surfaces having radii of curvature $r_3$ and $r_4$; a middle lens group that consists of three lens components, specifically, a cemented second lens component formed of a meniscus lens element having negative refractive power cemented to a biconvex lens element with radii of curvature $r_5$, $r_6$, and $r_7$, a third lens component that has positive refractive power and is formed of a single lens element with lens surfaces having radii of curvature $r_9$ and $r_{10}$, and a fourth lens component that has positive refractive power and is formed of a single lens element with lens surfaces having radii of curvature $r_{11}$ and $r_{12}$; and a rear lens group composed of a cemented lens component formed of a biconvex lens element cemented to a meniscus lens element having negative refractive power with radii of curvature $r_{13}$, $r_{14}$, and $r_{15}$. Focusing from the far point to the near point is performed by moving the third lens component toward the image side. A stop S with radius of curvature $r_8$ for controlling image brightness is arranged between the second lens component and the third lens component.

Embodiment 12 is an example of an optical system according to the first and second modes of construction of the present invention with the middle lens group, referenced by "GM" in Table 12 above and in FIG. 12, being composed of second, third, and fourth lens components having positive refractive power.

Embodiment 12 is very similar to Embodiment 5 except that in Embodiment 12 the second lens component is a cemented lens component rather than a single lens element.

Embodiment 12 of the present invention satisfies Conditions (1) through (7) above, as shown by Table 12 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 12, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 39A:
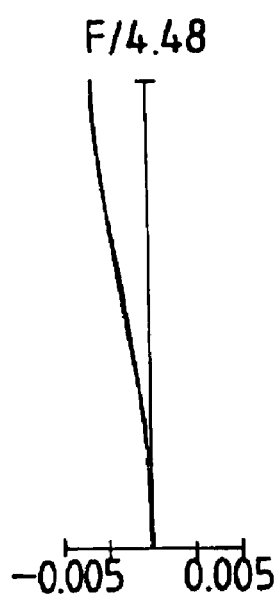
FIGS. 39A-39C show the spherical aberration, astigmatism, and distortion, respectively, of Embodiment 12 of the present invention when focused at the far point on the object side.
Figure 39B:
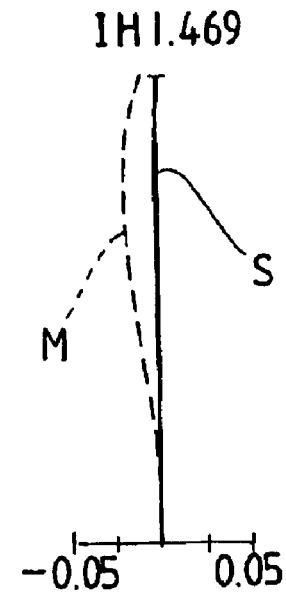
Figure 39C:
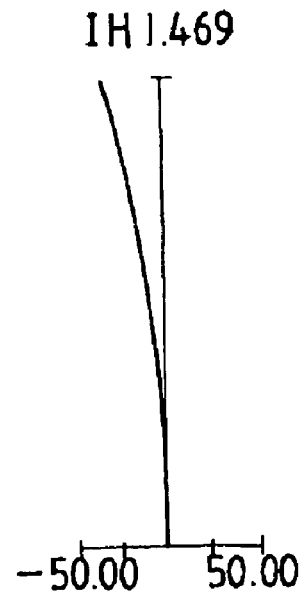
Figure 39D:
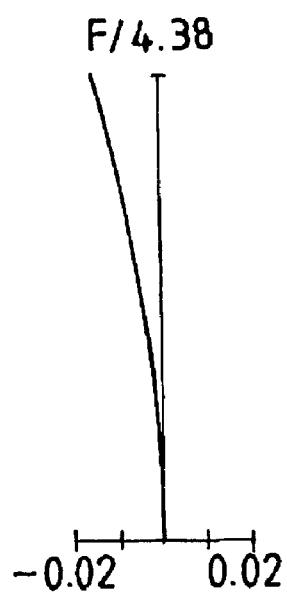
FIGS. 39D-39F show the spherical aberration, astigmatism, and distortion, respectively, of Embodiment 12 of the present invention when focused at the near point on the object side.
Figure 39E:
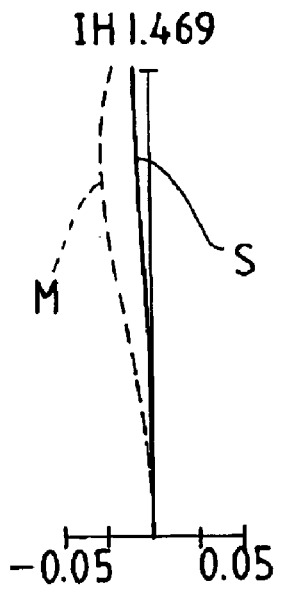
Figure 39F:

FIGS. 39A-39C show the spherical aberration, astigmatism, and distortion, respectively, of Embodiment 12 of the present invention when focused at the far point on the object side, and FIGS. 39D-39F show the spherical aberration, astigmatism, and distortion, respectively, of Embodiment 12 of the present invention when focused at the near point on the object side. As shown in FIGS. 39A-39C and FIGS. 39D-39F, in Embodiment 12 these aberrations are favorably corrected.

EMBODIMENT 13

Figure 13:
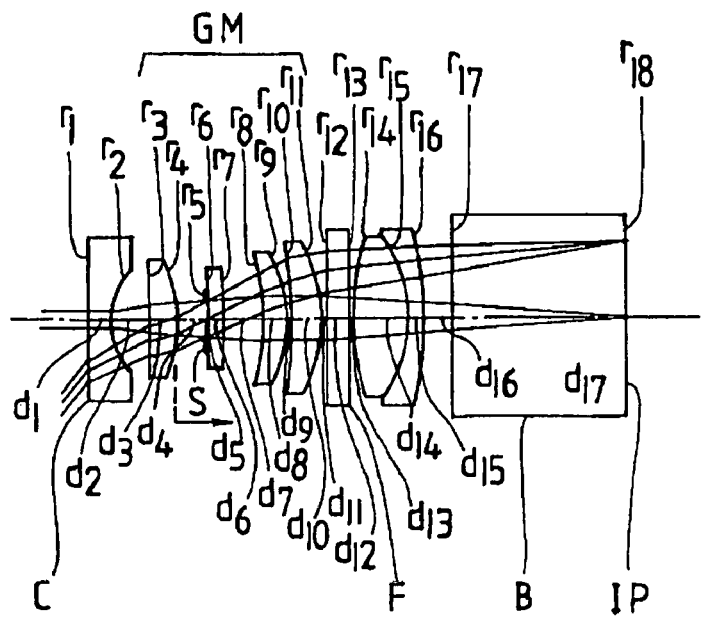
FIG. 13 is a cross-sectional view of Embodiment 13 of the present invention focused at the far point on the object side.

FIG. 13 shows a cross-sectional view of the objective optical system for an endoscope of Embodiment 13 of the present invention. Table 13 below lists the various data explained above for Embodiment 13.

TABLE 13

| Far point focused state | | | |
|---|---|---|---|
| WD = 48 | $f_{TF}$ = 1.790 | $F_{NO}$ = 4.51 | 2 ω = 98.6° |
| | Near point focused state | | |
| WD = 23 | $f_{TN}$ = 1.755 | $F_{NO}$ = 4.51 | 2 ω = 101.1° |
| $r_1 = \infty$ | $d_1$ = 0.5000 | $n_1$ = 1.76820 | $v_1$ = 71.79 |
| $r_2$ = 1.4015 | $d_2$ = 0.8000 | | |
| $r_3$ = −16.2330 | $d_3$ = 0.5800 | $n_2$ = 1.77250 | $v_2$ = 49.60 |
| $r_4$ = −2.6697 | $d_4$ = 0.5669 | | |
| $r_5 = \infty$ (stop) | $d_5$ = 0.0500 | | |
| $r_6$ = −7.6446 | $d_6$ = 0.3000 | $n_3$ = 1.72916 | $v_3$ = 54.68 |
| $r_7$ = −30.9574 | $d_7$ = 0.8248 | | |
| $r_8$ = −4.0005 | $d_8$ = 0.5000 | $n_4$ = 1.72916 | $v_4$ = 54.68 |
| $r_9$ = −2.5301 | $d_9$ = 0.1000 | | |
| $r_{10}$ = −7.5805 | $d_{10}$ = 0.6000 | $n_5$ = 1.72916 | $v_5$ = 54.68 |
| $r_{11}$ = −3.0214 | $d_{11}$ = 0.1000 | | |
| $r_{12} = \infty$ | $d_{12}$ = 0.4500 | $n_6$ = 1.51800 | $v_6$ = 75.00 |
| $r_{13} = \infty$ | $d_{13}$ = 0.1000 | | |
| $r_{14}$ = 5.5511 | $d_{14}$ = 1.1000 | $n_7$ = 1.58913 | $v_7$ = 61.14 |
| $r_{15}$ = −2.7000 | $d_{15}$ = 0.3000 | $n_8$ = 1.92286 | $v_8$ = 18.90 |
| $r_{16}$ = −7.1189 | $d_{16}$ = 0.6000 | | |
| $r_{17} = \infty$ | $d_{17}$ = 3.6000 | $n_9$ = 1.48749 | $v_9$ = 70.23 |
| $r_{18} = \infty$ (image plane) | | | |

| $|f_{UM}/f_{TF}|$ = 2.268 | $f_{U1}/f_{TF}$ = −1.019 | $f_{TN}/f_{TF}$ = 0.980 |
|---|---|---|
| $f_{U1}$ = −1.824 | $f_{U1}/f_{TF}$ = −1.02 | |
| $f_{U2}$ = 4.060 | $f_{U2}/f_{TF}$ = 2.27 | |
| $f_{U3}$ = −13.998 | $f_{U3}/f_{TF}$ = −7.82 | |
| $f_{U4}$ = 8.257 | $f_{U4}/f_{TF}$ = 4.61 | |
| $f_{U5}$ = 6.527 | $f_{U5}/f_{TF}$ = 3.65 | |
| $f_{UR}$ = 8.938 | $f_{UR}/f_{TF}$ = 4.99 | |
| $|f_U (GM, GR)|_{min}$ = 2.27 | $|R (GM, GR)|_{min}$ = 1.41 | |

TABLE 13-continued

| | |
|---|---|
| $n(GR_p) = n_7 = 1.58913$ | $n(GR_n) = n_8 = 1.92286$ |
| $v(GR_p) = v_7 = 61.14$ | $v(GR_n) = v_8 = 18.90$ |

As shown in FIG. 13, the optical system of Embodiment 13 is composed of: a front lens group that consists of a first lens component that has negative refractive power and is formed of a single lens element with lens surfaces having radii of curvature $r_1$ and $r_2$; a middle lens group that is composed of four lens components, specifically, a second lens component that has positive refractive power and is formed of a single lens element with lens surfaces having radii of curvature $r_3$ and $r_4$, a third lens component that has negative refractive power and is formed of a single lens element with lens surfaces having radii of curvature $r_6$ and $r_7$, a fourth lens component that has positive refractive power and is formed of a single lens element with lens surfaces having radii of curvature $r_8$ and $r_9$, and a fifth lens component that has positive refractive power and is formed of a single lens element with lens surfaces having radii of curvature $r_{10}$ and $r_{11}$; and a rear lens group composed of a cemented lens component formed of a biconvex lens element cemented to a meniscus lens element having negative refractive power with radii of curvature $r_{14}$, $r_{15}$, and $r_{16}$. Focusing from the far point to the near point is performed by moving the second lens component toward the image side. A stop S with radius of curvature $r_5$ for controlling image brightness is arranged between the second lens component and the third lens component, which are in the middle lens group where the ray height is relatively small.

Embodiment 13 is an example of an optical system according to the first and second modes of construction of the present invention with the middle lens group, referenced by "GM" in Table 13 above and in FIG. 13, being composed of second, fourth, and fifth lens components having positive refractive power. The correction of astigmatism and lateral color is made by using a cemented lens component as the image-side or rear lens component.

Embodiment 13 of the present invention satisfies Conditions (1) through (7) above, as shown by Table 13 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 13, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 40A:
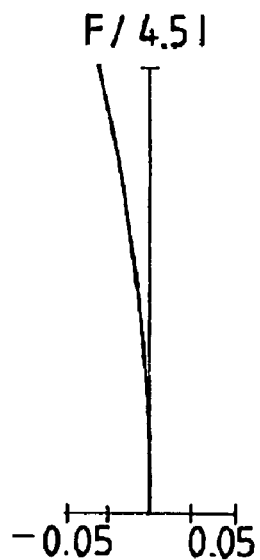
FIGS. 40A-40C show the spherical aberration, astigmatism, and distortion, respectively, of Embodiment 13 of the present invention when focused at the far point on the object side.
Figure 40B:
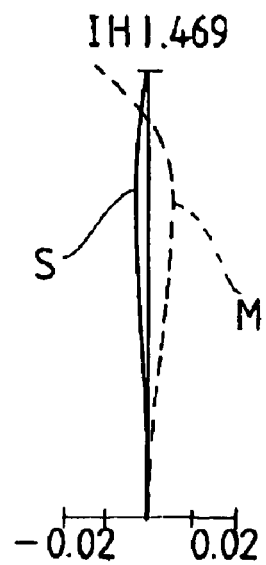
Figure 40C:
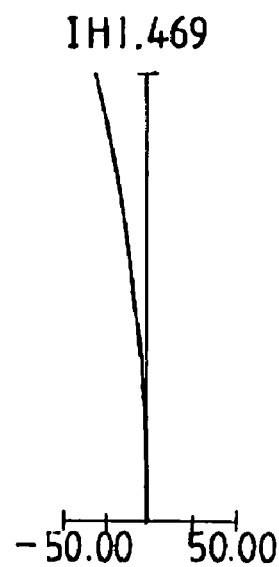
Figure 40D:
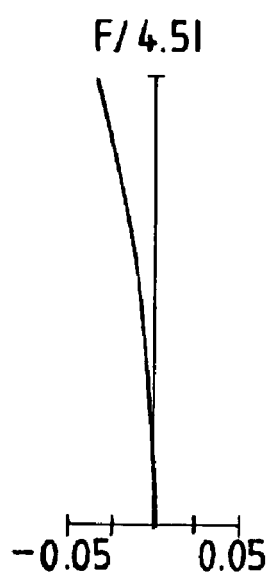
FIGS. 40D-40F show the spherical aberration, astigmatism, and distortion, respectively, of Embodiment 13 of the present invention when focused at the near point on the object side.
Figure 40E:
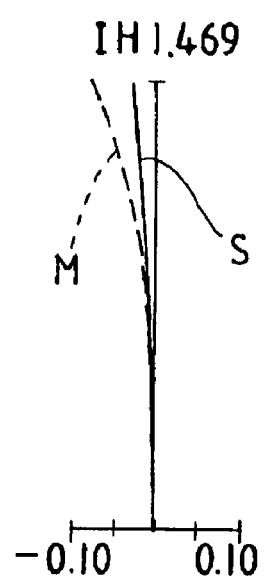
Figure 40F:
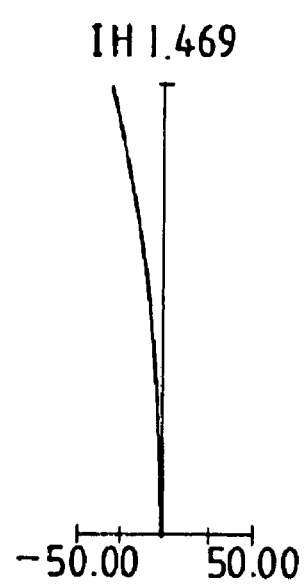

FIGS. 40A-40C show the spherical aberration, astigmatism, and distortion, respectively, of Embodiment 13 of the present invention when focused at the far point on the object side, and FIGS. 40D-40F show the spherical aberration, astigmatism, and distortion, respectively, of Embodiment 13 of the present invention when focused at the near point on the object side. As shown in FIGS. 40A-40C and FIGS. 40D-40F, in Embodiment 13 these aberrations are favorably corrected.

EMBODIMENT 14

Figure 14:
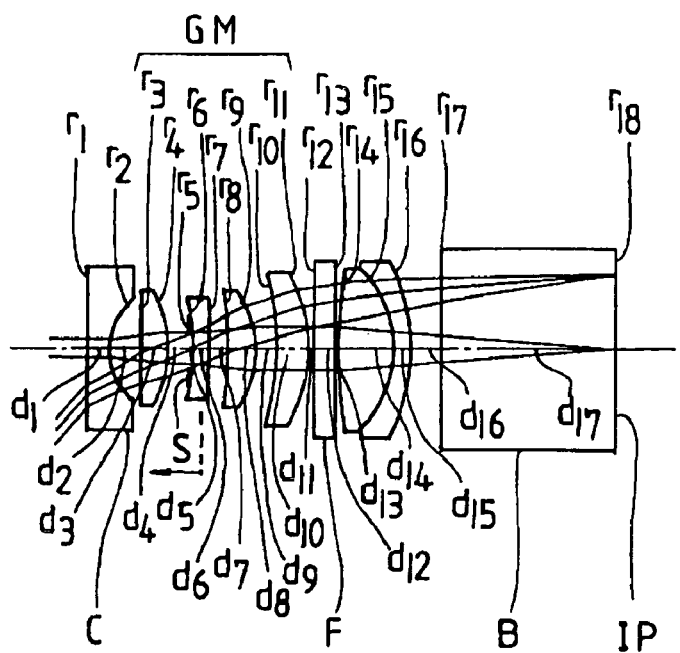
FIG. 14 is a cross-sectional view of Embodiment 14 of the present invention focused at the far point on the object side.

FIG. 14 shows a cross-sectional view of the objective optical system for an endoscope of Embodiment 14 of the present invention. Table 14 below lists the various data explained above for Embodiment 14.

TABLE 14

| Far point focused state | | | |
|---|---|---|---|
| WD = 48 | $f_{TF}$ = 1.785 | $F_{NO}$ = 4.49 | $2\omega$ = 98.6° |
| | Near point focused state | | |
| WD = 23 | $f_{TN}$ = 1.740 | $F_{NO}$ = 4.37 | $2\omega$ = 101.8° |

| | | | |
|---|---|---|---|
| $r_1 = \infty$ | $d_1 = 0.5000$ | $n_1 = 1.76820$ | $v_1 = 71.79$ |
| $r_2 = 1.2556$ | $d_2 = 0.6500$ | | |
| $r_3 = 237.2682$ | $d_3 = 0.5800$ | $n_2 = 1.78800$ | $v_2 = 47.37$ |
| $r_4 = -2.4658$ | $d_4 = 0.4852$ | | |
| $r_5 = \infty$ (stop) | $d_5 = 0.0500$ | | |
| $r_6 = -3.6904$ | $d_6 = 0.3000$ | $n_3 = 1.88300$ | $v_3 = 40.76$ |
| $r_7 = 683.8898$ | $d_7 = 0.4000$ | | |
| $r_8 = -7.7738$ | $d_8 = 0.6000$ | $n_4 = 1.72916$ | $v_4 = 54.68$ |
| $r_9 = -2.0106$ | $d_9 = 0.3967$ | | |
| $r_{10} = -6.3761$ | $d_{10} = 0.6486$ | $n_5 = 1.72916$ | $v_5 = 54.68$ |
| $r_{11} = -3.3230$ | $d_{11} = 0.1000$ | | |
| $r_{12} = \infty$ | $d_{12} = 0.4500$ | $n_6 = 1.51800$ | $v_6 = 75.00$ |
| $r_{13} = \infty$ | $d_{13} = 0.1000$ | | |
| $r_{14} = 11.0958$ | $d_{14} = 1.1000$ | $n_7 = 1.58913$ | $v_7 = 61.14$ |
| $r_{15} = -2.2011$ | $d_{15} = 0.3000$ | $n_8 = 1.92286$ | $v_8 = 18.90$ |
| $r_{16} = -4.1426$ | $d_{16} = 0.6000$ | | |
| $r_{17} = \infty$ | $d_{17} = 3.6000$ | $n_9 = 1.48749$ | $v_9 = 70.23$ |
| $r_{18} = \infty$ (image plane) | | | |

| | | |
|---|---|---|
| $|f_{UM}/f_{TF}|$ = 2.328 | $f_{U1}/f_{TF}$ = -0.916 | $f_{TN}/f_{TF}$ = 0.975 |

| | |
|---|---|
| $f_{U1}$ = -1.635 | $f_{U1}/f_{TF}$ = -0.92 |
| $f_{U2}$ = 3.100 | $f_{U2}/f_{TF}$ = 1.74 |
| $f_{U3}$ = -4.156 | $f_{U3}/f_{TF}$ = -2.33 |
| $f_{U4}$ = 3.563 | $f_{U4}/f_{TF}$ = 2.00 |
| $f_{U5}$ = 8.735 | $f_{U5}/f_{TF}$ = 4.89 |
| $f_{UR}$ = 8.009 | $f_{UR}/f_{TF}$ = 4.49 |
| $|f_U$ (GM, GR)$|_{min}$ = 1.74 | $|R$ (GM, GR)$|_{min}$ = 1.13 |
| $n(GR_p) = n_7 = 1.58913$ | $n(GR_n) = n_8 = 1.92286$ |
| $v(GR_p) = v_7 = 61.14$ | $v(GR_n) = v_8 = 18.90$ |

As shown in FIG. 14, the optical system of Embodiment 14 is composed of: a front lens group that consists of a first lens component that has negative refractive power and is formed of a single lens element with lens surfaces having radii of curvature $r_1$ and $r_2$; a middle lens group that is composed of four lens components, specifically, a second lens component that has positive refractive power and is formed of a single lens element with lens surfaces having radii of curvature $r_3$ and $r_4$, a third lens component that has negative refractive power and is formed of a single lens element with lens surfaces having radii of curvature $r_6$ and $r_7$, a fourth lens component that has positive refractive power and is formed of a single lens element with lens surfaces having radii of curvature $r_8$ and $r_9$, and a fifth lens component that has positive refractive power and is formed of a single lens element with lens surfaces having radii of curvature $r_{10}$ and $r_{11}$; and a rear lens group composed of a cemented lens component formed of a biconvex lens element cemented to a meniscus lens element having negative refractive power with radii of curvature $r_{14}$, $r_{15}$, and $r_{16}$. Focusing from the far point to the near point is performed by moving the third lens component toward the object side. A stop S with radius of curvature $r_5$ for controlling image brightness is arranged between the second lens component and the third lens component.

Embodiment 14 is an example of an optical system according to the first and third modes of construction of the present invention with the middle lens group, referenced by "GM" in Table 14 above and in FIG. 14, being composed of second and fifth lens components having positive refractive power separated by third and fourth lens components. Embodiment 14 is very similar to Embodiment 13 in construction but in Embodiment 14 the third lens component is moved for focusing instead of the second lens component and that third lens component moves toward the object side rather than toward the image side when focusing from the far point to the near point.

Embodiment 14 of the present invention satisfies Conditions (1) through (7) above, as shown by Table 14 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 14, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 41A:
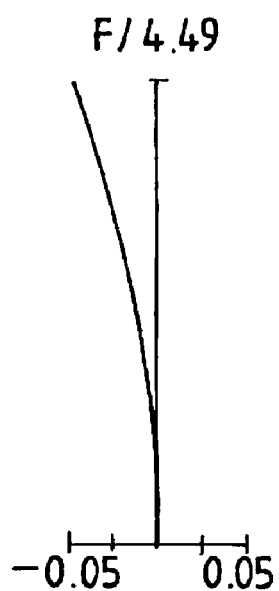
FIGS. 41A-41C show the spherical aberration, astigmatism, and distortion, respectively, of Embodiment 14 of the present invention when focused at the far point on the object side.
Figure 41B:
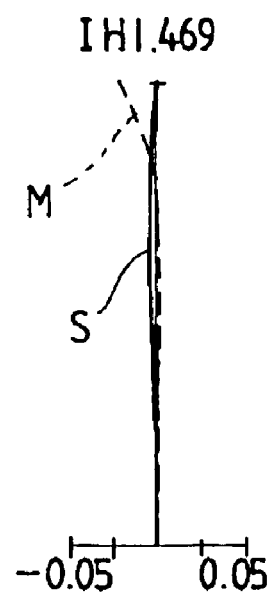
Figure 41C:
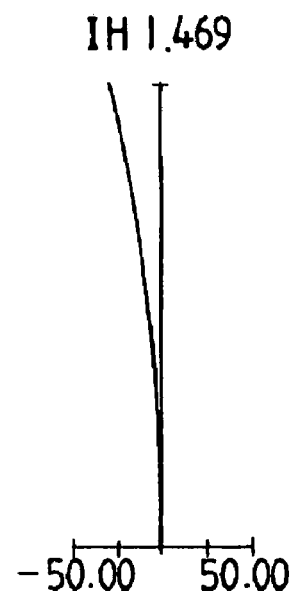
Figure 41D:
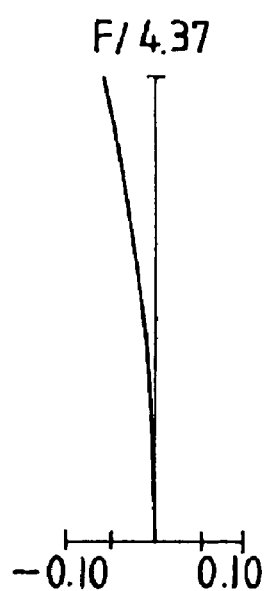
FIGS. 41D-41F show the spherical aberration, astigmatism, and distortion, respectively, of Embodiment 14 of the present invention when focused at the near point on the object side.
Figure 41E:
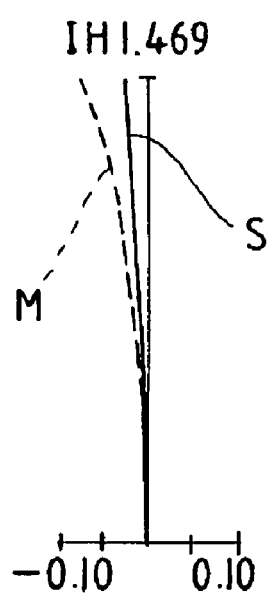
Figure 41F:

FIGS. 41A-41C show the spherical aberration, astigmatism, and distortion, respectively, of Embodiment 14 of the present invention when focused at the far point on the object side, and FIGS. 41D-41F show the spherical aberration, astigmatism, and distortion, respectively, of Embodiment 14 of the present invention when focused at the near point on the object side. As shown in FIGS. 41A-41C and FIGS. 41D-41F, in Embodiment 14 these aberrations are favorably corrected.

EMBODIMENT 15

Figure 15:
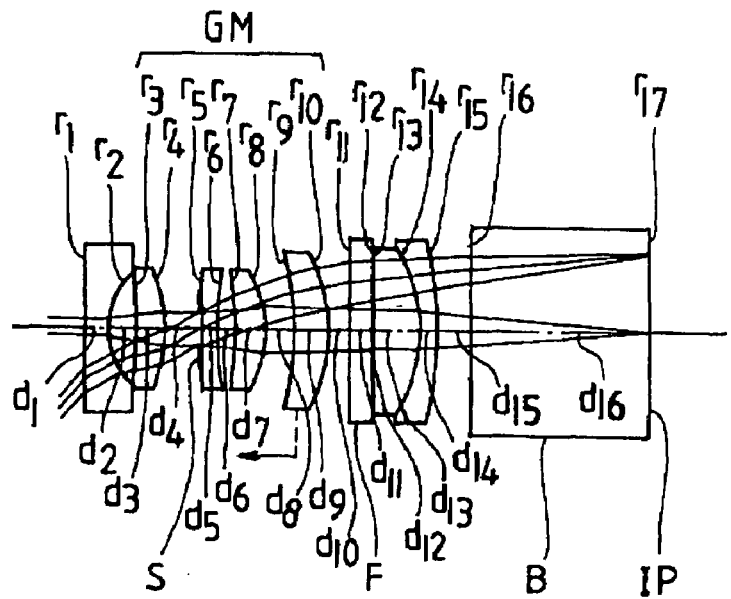
FIG. 15 is a cross-sectional view of Embodiment 15 of the present invention focused at the far point on the object side.

FIG. 15 shows a cross-sectional view of the objective optical system for an endoscope of Embodiment 15 of the present invention. Table 15 below lists the various data explained above for Embodiment 15.

TABLE 15

| Far point focused state | | | |
|---|---|---|---|
| WD = 46 | $f_{TF}$ = 1.800 | $F_{NO}$ = 4.47 | 2ω = 98.6° |
| | Near point focused state | | |
| WD = 23 | $f_{TN}$ = 1.808 | $F_{NO}$ = 4.52 | 2ω = 97.5° |
| $r_1$ = ∞ | $d_1$ = 0.5000 | $n_1$ = 1.76820 | $v_1$ = 71.79 |
| $r_2$ = 1.3600 | $d_2$ = 0.5500 | | |
| $r_3$ = −14.8406 | $d_3$ = 0.6080 | $n_2$ = 1.69895 | $v_2$ = 30.13 |
| $r_4$ = −2.8154 | $d_4$ = 0.7455 | | |
| $r_5$ = ∞ (stop) | $d_5$ = 0.3000 | $n_3$ = 1.80518 | $v_3$ = 25.42 |
| $r_6$ = 5.1000 | $d_6$ = 0.3702 | | |
| $r_7$ = −7.6195 | $d_7$ = 0.6500 | $n_4$ = 1.72916 | $v_4$ = 54.68 |
| $r_8$ = −2.0504 | $d_8$ = 0.5297 | | |
| $r_9$ = −6.5756 | $d_9$ = 0.7332 | $n_5$ = 1.72916 | $v_5$ = 54.68 |
| $r_{10}$ = −2.8745 | $d_{10}$ = 0.4000 | | |
| $r_{11}$ = ∞ | $d_{11}$ = 0.4500 | $n_6$ = 1.51800 | $v_6$ = 75.00 |
| $r_{12}$ = ∞ | $d_{12}$ = 0.0300 | | |
| $r_{13}$ = 122.5433 | $d_{13}$ = 0.9200 | $n_7$ = 1.75500 | $v_7$ = 52.32 |
| $r_{14}$ = −2.7121 | $d_{14}$ = 0.3000 | $n_8$ = 1.92286 | $v_8$ = 18.90 |
| $r_{15}$ = −6.3829 | $d_{15}$ = 0.6756 | | |
| $r_{16}$ = ∞ | $d_{16}$ = 3.6000 | $n_9$ = 1.48749 | $v_9$ = 70.23 |
| $r_{17}$ = ∞ (image plane) | | | |

| $|f_{UM}/f_{TF}|$ = 3.591 | $f_{U1}/f_{TF}$ = −0.983 | $f_{TN}/f_{TF}$ = 1.004 |
|---|---|---|
| $f_{U1}$ = −1.770 | | $f_{U1}/f_{TF}$ = −0.98 |
| $f_{U2}$ = 4.870 | | $f_{U2}/f_{TF}$ = 2.71 |
| $f_{U3}$ = −6.334 | | $f_{U3}/f_{TF}$ = −3.52 |
| $f_{U4}$ = 3.667 | | $f_{U4}/f_{TF}$ = 2.04 |

TABLE 15-continued

| $f_{U5}$ = 6.464 | $f_{U5}/f_{TF}$ = 3.59 |
|---|---|
| $f_{UR}$ = 11.131 | $f_{UR}/f_{TF}$ = 6.18 |
| $|f_U (GM, GR)|_{min}$ = 2.04 | $|R (GM, GR)|_{min}$ = 1.14 |
| $n(GR_p) = n_7$ = 1.75500 | $n(GR_n) = n_8$ = 1.92286 |
| $v(GR_p) = v_7$ = 52.32 | $v(GR_n) = v_8$ = 18.90 |

As shown in FIG. 15, the optical system of Embodiment 15 is composed of: a front lens group that consists of a first lens component that has negative refractive power and is formed of a single lens element with lens surfaces having radii of curvature $r_1$ and $r_2$; a middle lens group that is composed of four lens components, specifically, a second lens component that has positive refractive power and is formed of a single lens element with lens surfaces having radii of curvature $r_3$ and $r_4$, a third lens component that has negative refractive power and is formed of a single lens element with lens surfaces having radii of curvature $r_5$ and $r_6$, a fourth lens component that has positive refractive power and is formed of a single lens element with lens surfaces having radii of curvature $r_7$ and $r_8$, and a fifth lens component that has positive refractive power and is formed of a single lens element with lens surfaces having radii of curvature $r_9$ and $r_{10}$; and a rear lens group composed of a cemented lens component formed of a biconvex lens element cemented to a meniscus lens element having negative refractive power with radii of curvature $r_{13}$, $r_{14}$, and $r_{15}$. Focusing from the far point to the near point is performed by moving the fifth lens component toward the object side. A stop S for controlling image brightness is arranged on the object-side surface of the third lens component that has a radius of curvature $r_5$.

Embodiment 15 is an example of an optical system according to the first and third modes of construction of the present invention with the middle lens group, referenced by "GM" in Table 15 above and in FIG. 15, being composed of second and fifth lens components having positive refractive power separated by third and fourth lens components.

Embodiment 15 is very similar to Embodiments 13 and 14 in construction but in Embodiment 15 the fifth lens component is moved for focusing instead of the second or third lens component. That fifth lens component moves toward the object side during focusing from the far point to the near point.

Embodiment 15 of the present invention satisfies Conditions (1) through (7) above, as shown by Table 15 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 15, the image side lens component that forms the rear lens group is a cemented lens component, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

FIGS. 42A-42C show the spherical aberration, astigmatism, and distortion, respectively, of Embodiment 15 of the present invention when focused at the far point on the object side, and FIGS. 42D-42F show the spherical aberration, astigmatism, and distortion, respectively, of Embodiment 15 of the present invention when focused at the near point on the object side. As shown in FIGS. 42A-42C and FIGS. 42D-42F, in Embodiment 15 these aberrations are favorably corrected.

EMBODIMENT 16

Figure 16:
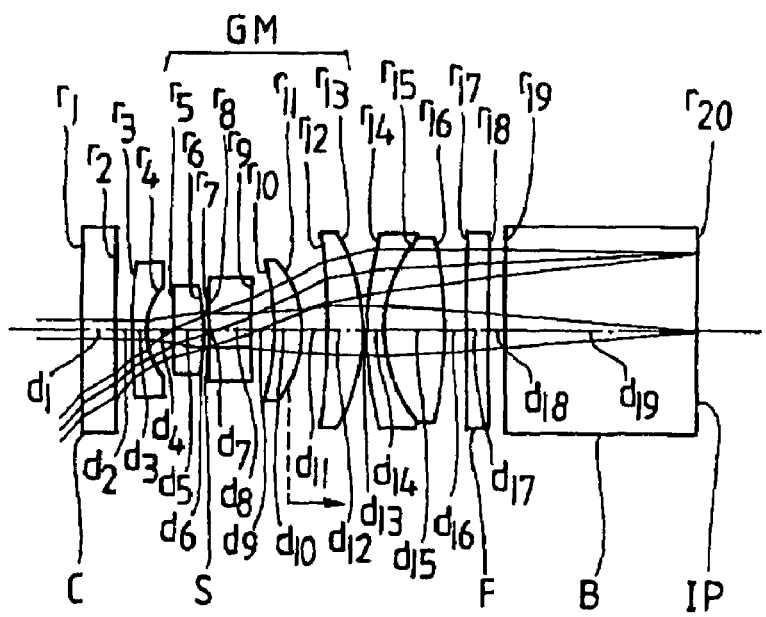
FIG. 16 is a cross-sectional view of Embodiment 16 of the present invention focused at the far point on the object side.

FIG. 16 shows a cross-sectional view of the objective optical system for an endoscope of Embodiment 16 of the present invention. Table 16 below lists the various data explained above for Embodiment 16.

TABLE 16

| Far point focused state | | | |
|---|---|---|---|
| WD = 46 | $f_{TF}$ = 1.760 | $F_{NO}$ = 4.52 | 2 ω = 101.6° |
| Near point focused state | | | |
| WD = 23 | $f_{TN}$ = 1.717 | $F_{NO}$ = 4.42 | 2 ω = 104.2° |
| $r_1$ = ∞ | $d_1$ = 0.7000 | $n_1$ = 1.76820 | $v_1$ = 71.79 |
| $r_2$ = ∞ | $d_2$ = 0.2900 | | |
| $r_3$ = 21.8706 | $d_3$ = 0.3000 | $n_2$ = 1.88300 | $v_2$ = 40.76 |
| $r_4$ = 1.2542 | $d_4$ = 0.5300 | | |
| $r_5$ = 162.1167 | $d_5$ = 0.6417 | $n_3$ = 1.78472 | $v_3$ = 25.68 |
| $r_6$ = −3.5000 | $d_6$ = 0.1000 | | |
| $r_7$ = ∞ (stop) | $d_7$ = 0.0300 | | |
| $r_8$ = ∞ | $d_8$ = 0.8361 | $n_4$ = 1.88300 | $v_4$ = 40.76 |
| $r_9$ = 10.6992 | $d_9$ = 0.4814 | | |
| $r_{10}$ = −4.5000 | $d_{10}$ = 0.6000 | $n_5$ = 1.48749 | $v_5$ = 70.23 |
| $r_{11}$ = −2.0113 | $d_{11}$ = 0.4743 | | |
| $r_{12}$ = −10.3986 | $d_{12}$ = 0.7000 | $n_6$ = 1.88300 | $v_6$ = 40.76 |
| $r_{13}$ = −3.6699 | $d_{13}$ = 0.1000 | | |
| $r_{14}$ = 7.6980 | $d_{14}$ = 0.3000 | $n_7$ = 1.92286 | $v_7$ = 18.90 |
| $r_{15}$ = 2.6490 | $d_{15}$ = 1.2000 | $n_8$ = 1.72916 | $v_8$ = 54.68 |
| $r_{16}$ = −7.9927 | $d_{16}$ = 0.4489 | | |
| $r_{17}$ = ∞ | $d_{17}$ = 0.4500 | $n_9$ = 1.51800 | $v_9$ = 75.00 |
| $r_{18}$ = ∞ | $d_{18}$ = 0.3000 | | |
| $r_{19}$ = ∞ | $d_{19}$ = 3.9000 | $n_{10}$ = 1.51633 | $v_{10}$ = 64.14 |
| $r_{20}$ = ∞ (image plane) | | | |

| $|f_{UM}/f_{TF}|$ = 3.928 | $f_{U1}/f_{TF}$ = −0.862 | $f_{TN}/f_{TF}$ = 0.976 |
|---|---|---|
| $f_{U1}$ = −1.517 | | $f_{U1}/f_{TF}$ = −0.86 |
| $f_{U2}$ = 4.373 | | $f_{U2}/f_{TF}$ = 2.49 |
| $f_{U3}$ = −12.117 | | $f_{U3}/f_{TF}$ = −6.89 |
| $f_{U4}$ = 6.914 | | $f_{U4}/f_{TF}$ = 3.93 |
| $f_{U5}$ = 6.124 | | $f_{U5}/f_{TF}$ = 3.48 |
| $f_{UR}$ = 7.429 | | $f_{UR}/f_{TF}$ = 4.22 |
| $|f_U (GM, GR)|_{min}$ = 2.48 | | $|R (GM, GR)|_{min}$ = 1.14 |
| $n(GR_p) = n_8$ = 1.72916 | | $n(GR_n) = n_7$ = 1.92286 |
| $v(GR_p) = v_8$ = 54.68 | | $v(GR_n) = v_7$ = 18.90 |

As shown in FIG. 16, the optical system of Embodiment 16 is composed of: a front lens group that consists of a first lens component that has negative refractive power and is formed of a single lens element with lens surfaces having radii of curvature $r_3$ and $r_4$; a middle lens group that is composed of four lens components, specifically, a second lens component that has positive refractive power and is formed of a single lens element with lens surfaces having radii of curvature $r_5$ and $r_6$, a third lens component that has negative refractive power and is formed of a single lens element with lens surfaces having radii of curvature $r_8$ and $r_9$, a fourth lens component that has positive refractive power and is formed of a single lens element with lens surfaces having radii of curvature $r_{10}$ and $r_{11}$, and a fifth lens component that has positive refractive power and is formed of a single lens element with lens surfaces having radii of curvature $r_{12}$ and $r_{13}$; and a rear lens group composed of a cemented lens with radii of curvature $r_{14}$, $r_{15}$, and $r_{16}$. Focusing from the far point to the near point is performed by moving the fourth lens component toward the image side, and a stop S for controlling image brightness is arranged between the second lens component and the third lens component and has a radius of curvature $r_7$.

Embodiment 16 is an example of an optical system according to the first and third modes of construction of the present invention with the middle lens group, referenced by "GM" in Table 16 above and in FIG. 16, being composed of second and fifth lens components having positive refractive power separated by third and fourth lens components.

Embodiment 16 is very similar to Embodiments 13, 14, and 15 in construction but in Embodiment 16 the fourth lens component is moved for focusing, a sapphire plane parallel plate C is arranged on the object side of the first lens component, and the first lens component is made of glass with a higher refractive index than sapphire.

Embodiment 16 of the present invention satisfies Conditions (1) through (7) above, as shown by Table 16 above. The focal lengths $f_L(GM,GR)$ of the lens components in the middle lens group and rear lens group and the radii of curvature R(GM,GR) of the lens surfaces of the lens components in the middle lens group and rear lens group also satisfy the applicable conditions and design criteria specified for them.

In Embodiment 16, the image side lens component that forms the rear lens group is a cemented lens component composed of a lens element having negative refractive power and a lens element having positive refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 43A:
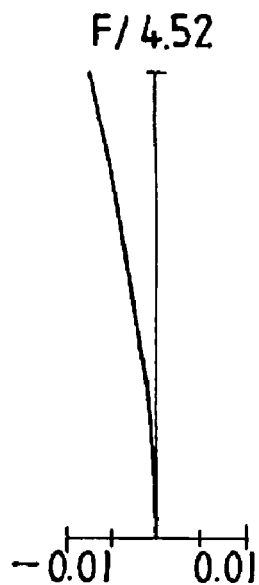
FIGS. 43A-43C show the spherical aberration, astigmatism, and distortion, respectively, of Embodiment 16 of the present invention when focused at the far point on the object side.
Figure 43B:
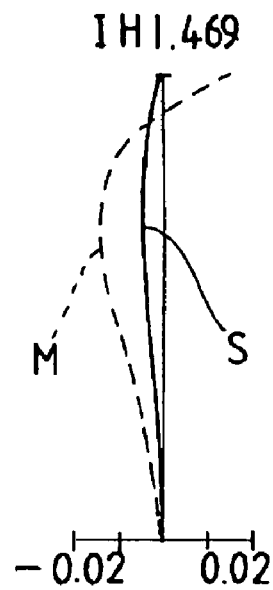
Figure 43C:
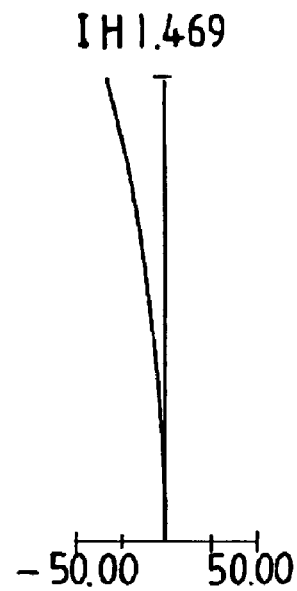
Figure 43D:
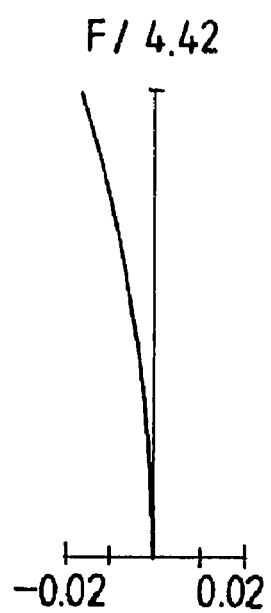
FIGS. 43D-43F show the spherical aberration, astigmatism, and distortion, respectively, of Embodiment 16 of the present invention when focused at the near point on the object side.
Figure 43E:
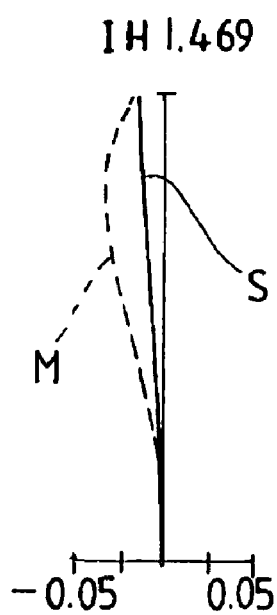
Figure 43F:
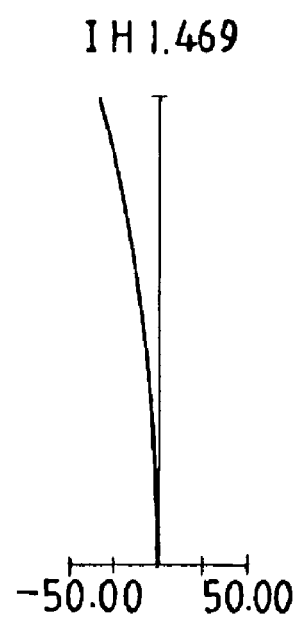

FIGS. 43A-43C show the spherical aberration, astigmatism, and distortion, respectively, of Embodiment 16 of the present invention when focused at the far point on the object side, and FIGS. 43D-43F show the spherical aberration, astigmatism, and distortion, respectively, of Embodiment 16 of the present invention when focused at the near point on the object side. As shown in FIGS. 43A-43C and FIGS. 43D-43F, in Embodiment 16 these aberrations are favorably corrected.

EMBODIMENT 17

Figure 17:
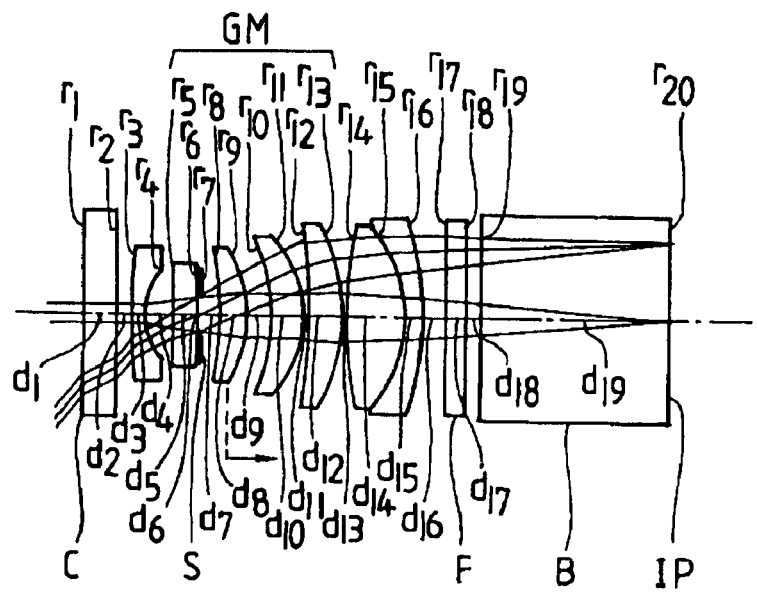
FIG. 17 is a cross-sectional view of Embodiment 17 of the present invention focused at the far point on the object side.

FIG. 17 shows a cross-sectional view of the objective optical system for an endoscope of Embodiment 17 of the present invention. Table 17 below lists the various data explained above for Embodiment 17.

TABLE 17

| Far point focused state | | | |
|---|---|---|---|
| WD = 48 | $f_{TF}$ = 1.760 | $F_{NO}$ = 4.46 | 2 ω = 104.6° |
| Near point focused state | | | |
| WD = 23 | $f_{TN}$ = 1.725 | $F_{NO}$ = 4.39 | 2 ω = 105.9° |
| $r_1$ = ∞ | $d_1$ = 0.7000 | $n_1$ = 1.76820 | $v_1$ = 71.79 |
| $r_2$ = ∞ | $d_2$ = 0.2900 | | |
| $r_3$ = 11.9476 | $d_3$ = 0.3000 | $n_2$ = 1.88300 | $v_2$ = 40.76 |
| $r_4$ = 1.1909 | $d_4$ = 0.5300 | | |
| $r_5$ = 25.1818 | $d_5$ = 0.5702 | $n_3$ = 1.92286 | $v_3$ = 18.90 |
| $r_6$ = −22.1060 | $d_6$ = 0.0300 | | |
| $r_7$ = ∞ (stop) | $d_7$ = 0.4323 | | |
| $r_8$ = −5.0000 | $d_8$ = 0.5500 | $n_4$ = 1.51742 | $v_4$ = 52.43 |
| $r_9$ = −2.5842 | $d_9$ = 0.4849 | | |
| $r_{10}$ = −4.3178 | $d_{10}$ = 0.7000 | $n_5$ = 1.51633 | $v_5$ = 64.14 |
| $r_{11}$ = −2.0618 | $d_{11}$ = 0.1000 | | |
| $r_{12}$ = −12.1564 | $d_{12}$ = 0.6500 | $n_6$ = 1.72916 | $v_6$ = 54.68 |
| $r_{13}$ = −3.8146 | $d_{13}$ = 0.1000 | | |
| $r_{14}$ = 8.6985 | $d_{14}$ = 1.2000 | $n_7$ = 1.58913 | $v_7$ = 61.14 |
| $r_{15}$ = −2.6089 | $d_{15}$ = 0.3000 | $n_8$ = 1.92286 | $v_8$ = 18.90 |
| $r_{16}$ = −6.1725 | $d_{16}$ = 0.4559 | | |
| $r_{17}$ = ∞ | $d_{17}$ = 0.4500 | $n_9$ = 1.51800 | $v_9$ = 75.00 |
| $r_{18}$ = ∞ | $d_{18}$ = 0.3000 | | |
| $r_{19}$ = ∞ | $d_{19}$ = 3.9000 | $n_{10}$ = 1.51633 | $v_{10}$ = 64.14 |
| $r_{20}$ = ∞ (image plane) | | | |

TABLE 17-continued

| $\lvert f_{UM}/f_{TF}\rvert = 5.450$ | $f_{U1}/f_{TF} = -0.863$ | $f_{TN}/f_{TF} = 0.980$ |
|---|---|---|
| $f_{U1} = -1.518$ | $f_{U1}/f_{TF} = -0.86$ | |
| $f_{U2} = 12.830$ | $f_{U2}/f_{TF} = 7.29$ | |
| $f_{U3} = 9.592$ | $f_{U3}/f_{TF} = 5.45$ | |
| $f_{U4} = 6.912$ | $f_{U4}/f_{TF} = 3.93$ | |
| $f_{U5} = 7.381$ | $f_{U5}/f_{TF} = 4.19$ | |
| $f_{UR} = 11.177$ | $f_{UR}/f_{TF} = 6.35$ | |
| $\lvert f_U\,(GM, GR)\rvert_{min} = 3.93$ | $\lvert R\,(GM, GR)\rvert_{min} = 1.17$ | |
| $n(GR_p) = n_7 = 1.58913$ | $n(GR_n) = n_8 = 1.92286$ | |
| $v(GR_p) = v_7 = 61.14$ | $v(GR_n) = v_8 = 18.90$ | |

As shown in FIG. 17, the optical system of Embodiment 17 is composed of: a front lens group that consists of a first lens component that has negative refractive power and is formed of a single lens element with lens surfaces having radii of curvature $r_3$ and $r_4$; a middle lens group that is composed of four lens components, specifically, second, third, fourth, and fifth lens components, each of which has positive refractive power and is formed of a single lens element with lens surfaces having radii of curvature $r_5$ and $r_6$, $r_8$ and $r_9$, $r_{10}$ and $r_{11}$, and $r_{12}$ and $r_{13}$, respectively; and a rear lens group composed of a cemented lens component formed of a biconvex lens element cemented to a meniscus lens element having negative refractive power with radii of curvature $r_{14}$, $r_{15}$, and $r_{16}$. Focusing from the far point to the near point is performed by moving the third lens component toward the image side, and a stop S for controlling image brightness is arranged between the second lens component and the third lens component and has a radius of curvature $r_7$. A sapphire plane parallel plate C is arranged on the object side of the first lens component.

Embodiment 17 is an example of an optical system according to the first and third modes of construction of the present invention with the middle lens group, referenced by "GM" in Table 17 above and in FIG. 17, being composed of second, third, fourth, and fifth lens components having positive refractive power.

Embodiment 17 is very similar to Embodiment 14 in construction but in Embodiment 17 the third lens component has positive refractive power.

Embodiment 17 of the present invention satisfies Conditions (1) through (7) above, as shown by Table 17 above. The focal lengths $f_U(GM,GR)$ of the lens components in the middle lens group and rear lens group and the radii of curvature $R(GM,GR)$ of the lens surfaces of the lens components in the middle lens group and rear lens group also satisfy the applicable conditions and design criteria specified for them. In Embodiment 17, the image side lens component that forms the rear lens group is a cemented lens component composed of a lens element having positive refractive power and a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 44A:
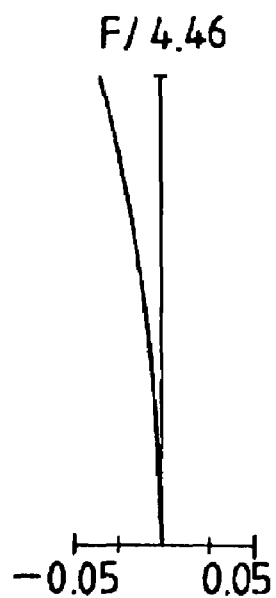
FIGS. 44A-44C show the spherical aberration, astigmatism, and distortion, respectively, of Embodiment 17 of the present invention when focused at the far point on the object side.
Figure 44B:
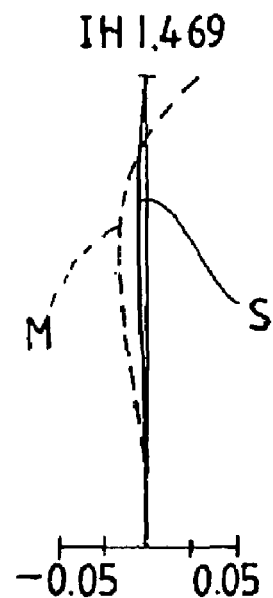
Figure 44C:
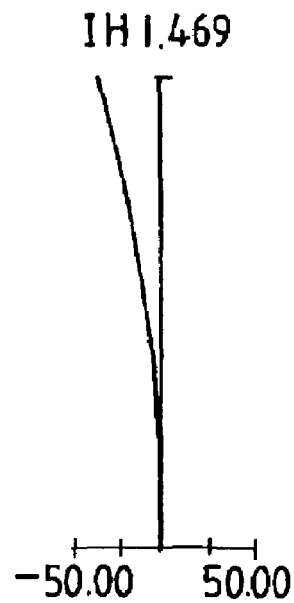
Figure 44D:
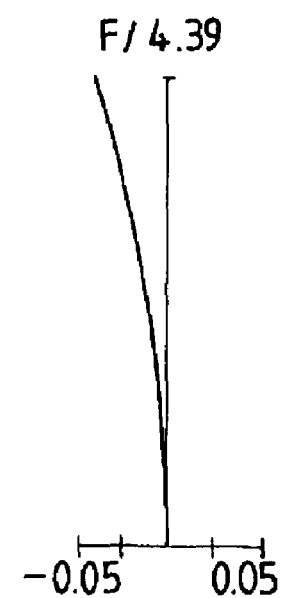
FIGS. 44D-44F show the spherical aberration, astigmatism, and distortion, respectively, of Embodiment 17 of the present invention when focused at the near point on the object side.
Figure 44E:
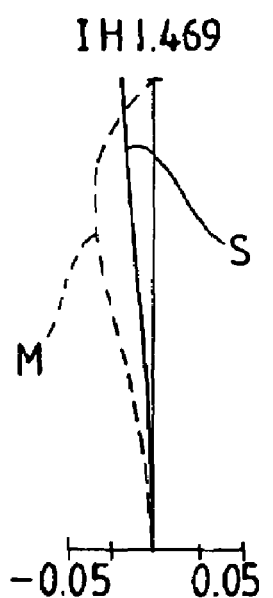
Figure 44F:
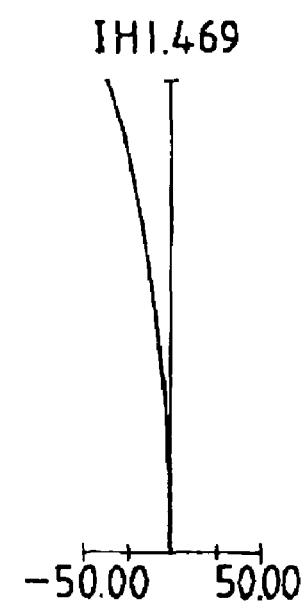

FIGS. 44A-44C show the spherical aberration, astigmatism, and distortion, respectively, of Embodiment 17 of the present invention when focused at the far point on the object side, and FIGS. 44D-44F show the spherical aberration, astigmatism, and distortion, respectively, of Embodiment 17 of the present invention when focused at the near point on the object side. As shown in FIGS. 44A-44C and FIGS. 44D-44F, in Embodiment 17 these aberrations are favorably corrected.

EMBODIMENT 18

Figure 18:
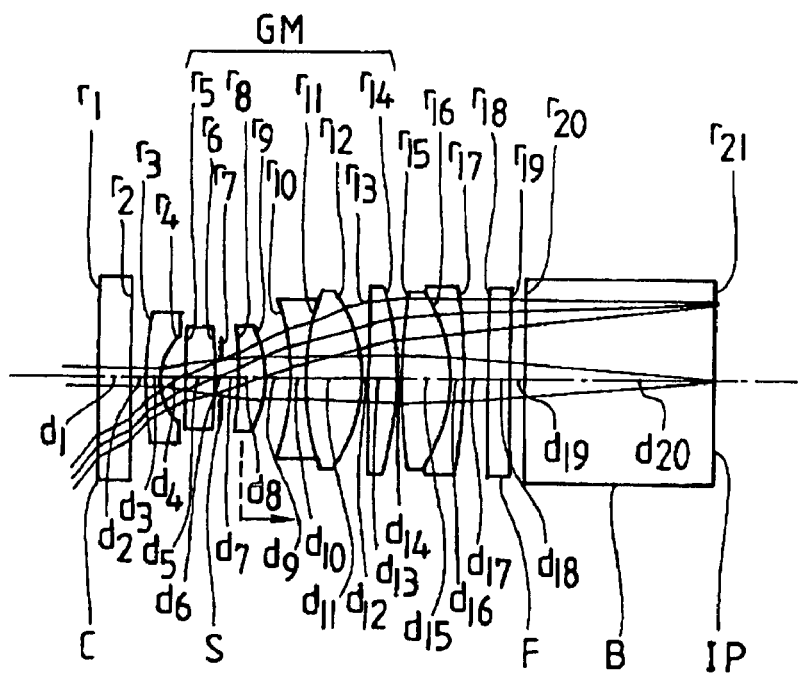
FIG. 18 is a cross-sectional view of Embodiment 18 of the present invention focused at the far point on the object side.

FIG. 18 shows a cross-sectional view of the objective optical system for an endoscope of Embodiment 18 of the present invention. Table 18 below lists the various data explained above for Embodiment 18.

TABLE 18

| Far point focused state | | | |
|---|---|---|---|
| WD = 47 | $f_{TF} = 1.750$ | $F_{NO} = 4.50$ | $2\omega = 102.5°$ |
| Near point focused state | | | |
| WD = 23 | $f_{TN} = 1.706$ | $F_{NO} = 4.40$ | $2\omega = 105.3°$ |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = 12.3202$ | $d_3 = 0.3000$ | $n_2 = 1.88300$ | $v_2 = 40.76$ |
| $r_4 = 1.1072$ | $d_4 = 0.5000$ | | |
| $r_5 = \infty$ | $d_5 = 0.6416$ | $n_3 = 1.92286$ | $v_3 = 18.90$ |
| $r_6 = -5.2798$ | $d_6 = 0.1000$ | | |
| $r_7 = \infty$ (stop) | $d_7 = 0.3788$ | | |
| $r_8 = -5.4871$ | $d_8 = 0.6000$ | $n_4 = 1.48749$ | $v_4 = 70.23$ |
| $r_9 = -1.8874$ | $d_9 = 0.4787$ | | |
| $r_{10} = -5.0755$ | $d_{10} = 0.3000$ | $n_5 = 1.88300$ | $v_5 = 40.76$ |
| $r_{11} = 5.2493$ | $d_{11} = 1.1700$ | $n_6 = 1.71999$ | $v_6 = 50.23$ |
| $r_{12} = -2.9289$ | $d_{12} = 0.1000$ | | |
| $r_{13} = \infty$ | $d_{13} = 0.6000$ | $n_7 = 1.72916$ | $v_7 = 54.68$ |
| $r_{14} = -6.1168$ | $d_{14} = 0.1000$ | | |
| $r_{15} = 14.0575$ | $d_{15} = 0.9500$ | $n_8 = 1.71999$ | $v_8 = 50.23$ |
| $r_{16} = -3.1558$ | $d_{16} = 0.3000$ | $n_9 = 1.92286$ | $v_9 = 18.90$ |
| $r_{17} = -10.2587$ | $d_{17} = 0.4710$ | | |
| $r_{18} = \infty$ | $d_{18} = 0.4500$ | $n_{10} = 1.51800$ | $v_{10} = 75.00$ |
| $r_{19} = \infty$ | $d_{19} = 0.3000$ | | |
| $r_{20} = \infty$ | $d_{20} = 3.9000$ | $n_{11} = 1.51633$ | $v_{11} = 64.14$ |
| $r_{21} = \infty$ (image plane) | | | |

| $\lvert f_{UM}/f_{TF}\rvert = 3.198$ | $f_{U1}/f_{TF} = -0.797$ | $f_{TN}/f_{TF} = 0.975$ |
|---|---|---|
| $f_{U1} = -1.395$ | $f_{U1}/f_{TF} = -0.80$ | |
| $f_{U2} = 5.721$ | $f_{U2}/f_{TF} = 3.27$ | |
| $f_{U3} = 5.596$ | $f_{U3}/f_{TF} = 3.20$ | |
| $f_{U4} = 12.318$ | $f_{U4}/f_{TF} = 7.04$ | |
| $f_{U5} = 8.389$ | $f_{U5}/f_{TF} = 4.79$ | |
| $f_{UR} = 13.102$ | $f_{UR}/f_{TF} = 7.49$ | |
| $\lvert f_U\,(GM, GR)\rvert_{min} = 3.20$ | $\lvert R\,(GM, GR)\rvert_{min} = 1.08$ | |
| $n(GR_p) = n_8 = 1.71999$ | $n(GR_n) = n_9 = 1.92286$ | |
| $v(GR_p) = v_8 = 50.23$ | $v(GR_n) = v_9 = 18.90$ | |

As shown in FIG. 18, the optical system of Embodiment 18 is composed of: a front lens group that consists of a first lens component that has negative refractive power and is formed of a single lens element with lens surfaces having radii of curvature $r_3$ and $r_4$; a middle lens group that is composed of four lens components, specifically, a second lens component that has positive refractive power and is formed of a single lens element with lens surfaces having radii of curvature $r_5$ and $r_6$, a third lens component that has positive refractive power and is formed of a single lens element with lens surfaces having radii of curvature $r_8$ and $r_9$, a cemented fourth lens component that has positive refractive power and is formed of a biconcave lens element cemented to a biconvex lens element and having radii of curvature $r_{10}$, $r_{11}$, and $r_{12}$, and a fifth lens component that has positive refractive power and is formed of a single lens element with lens surfaces having radii of curvature $r_{13}$ and $r_{14}$; and a rear lens group composed of a cemented lens component formed of a biconvex lens element cemented to a meniscus lens element having negative refractive power with radii of curvature $r_{15}$, $r_{16}$, and $r_{17}$. Focusing from the far point to the near point is performed by moving the third lens component toward the image side, and a stop S for controlling image brightness is arranged between the second lens component and the third lens component.

Embodiment 18 is an example of an optical system according to the first and third modes of construction of the present invention with the middle lens group, referenced by "GM" in Table 18 above and in FIG. 18, being composed of second, third, fourth, and fifth lens components having positive refractive power.

Embodiment 18 is very similar to Embodiment 17 in construction but in Embodiment 18 the fourth lens component is a cemented lens component.

Embodiment 18 of the present invention satisfies Conditions (1) through (7) above, as shown by Table 18 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. In Embodiment 18, the image side lens component that forms the rear lens group is a cemented lens component composed of a lens element having positive refractive power cemented to a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

FIGS. 45A-45C show the spherical aberration, astigmatism, and distortion, respectively, of Embodiment 18 of the present invention when focused at the far point on the object side, and FIGS. 45D-45F show the spherical aberration, astigmatism, and distortion, respectively, of Embodiment 18 of the present invention when focused at the near point on the object side. As shown in FIGS. 45A-45C and FIGS. 45D-45F, in Embodiment 18 these aberrations are favorably corrected.

EMBODIMENT 19

Figure 19:
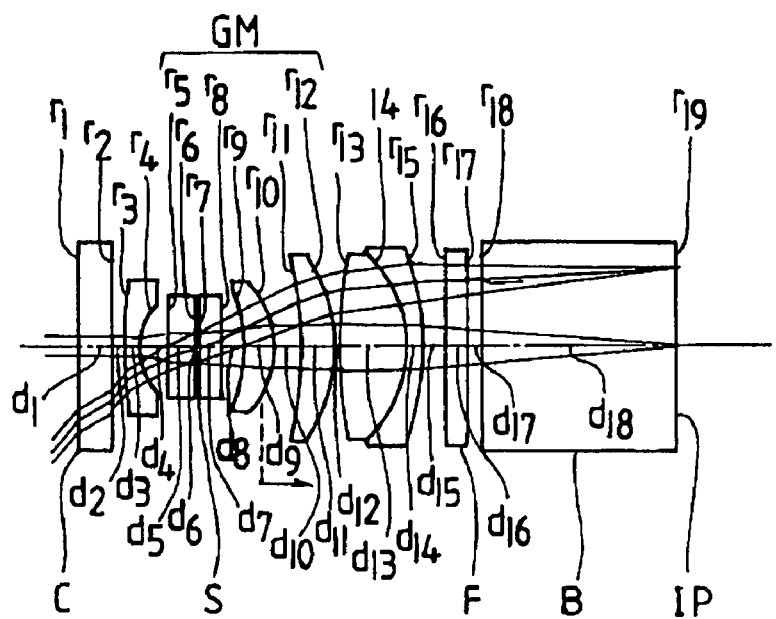
FIG. 19 is a cross-sectional view of Embodiment 19 of the present invention focused at the far point on the object side.

FIG. 19 shows a cross-sectional view of the objective optical system for an endoscope of Embodiment 19 of the present invention. Table 19 below lists the various data explained above for Embodiment 19.

TABLE 19

| | Far point focused state | | |
|---|---|---|---|
| WD = 48 | $f_{TF}$ = 1.770 | $F_{NO}$ = 4.48 | 2 ω = 103.2° |
| | Near point focused state | | |
| WD = 23 | $f_{TN}$ = 1.725 | $F_{NO}$ = 4.38 | 2 ω = 105.7° |
| $r_1$ = ∞ | $d_1$ = 0.7000 | $n_1$ = 1.76820 | $v_1$ = 71.79 |
| $r_2$ = ∞ | $d_2$ = 0.2900 | | |
| $r_3$ = 11.6817 | $d_3$ = 0.3000 | $n_2$ = 1.88300 | $v_2$ = 40.76 |
| $r_4$ = 1.2075 | $d_4$ = 0.5300 | | |
| $r_5$ = 13.1653 | $d_5$ = 0.5550 | $n_3$ = 1.92286 | $v_3$ = 18.90 |
| $r_6$ = ∞ | $d_6$ = 0.0300 | | |
| $r_7$ = ∞ (stop) | $d_7$ = 0.4994 | $n_4$ = 1.84666 | $v_4$ = 23.78 |
| $r_8$ = −14.8388 | $d_8$ = 0.4380 | | |
| $r_9$ = −2.8722 | $d_9$ = 0.6000 | $n_5$ = 1.51742 | $v_5$ = 52.43 |
| $r_{10}$ = −1.7104 | $d_{10}$ = 0.4834 | | |
| $r_{11}$ = −7.9606 | $d_{11}$ = 0.7000 | $n_6$ = 1.77250 | $v_6$ = 49.60 |
| $r_{12}$ = −3.0691 | $d_{12}$ = 0.1000 | | |
| $r_{13}$ = 11.5500 | $d_{13}$ = 1.3300 | $n_7$ = 1.72916 | $v_7$ = 54.68 |
| $r_{14}$ = −2.3253 | $d_{14}$ = 0.3000 | $n_8$ = 1.92286 | $v_8$ = 18.90 |
| $r_{15}$ = −5.4291 | $d_{15}$ = 0.4639 | | |
| $r_{16}$ = ∞ | $d_{16}$ = 0.4500 | $n_9$ = 1.51800 | $v_9$ = 75.00 |
| $r_{17}$ = ∞ | $d_{17}$ = 0.3000 | | |
| $r_{18}$ = ∞ | $d_{18}$ = 3.9000 | $n_{10}$ = 1.51633 | $v_{10}$ = 64.14 |
| $r_{19}$ = ∞ (image plane) | | | |

TABLE 19-continued

| $|f_{UM}/f_{TF}|$ = 3.926 | $f_{U1}/f_{TF}$ = −0.873 | $f_{TN}/f_{TF}$ = 0.975 |
|---|---|---|
| $f_{U1}$ = −1.546 | | $f_{U1}/f_{TF}$ = −0.87 |
| $f_{U2}$ = 14.266 | | $f_{U2}/f_{TF}$ = 8.06 |
| $f_{U3}$ = 17.526 | | $f_{U3}/f_{TF}$ = 9.90 |
| $f_{U4}$ = 6.949 | | $f_{U4}/f_{TF}$ = 3.93 |
| $f_{U5}$ = 6.086 | | $f_{U5}/f_{TF}$ = 3.44 |
| $f_{UR}$ = 6.848 | | $f_{UR}/f_{TF}$ = 3.87 |
| $|f_U$ (GM, GR)$|_{min}$ = 3.44 | | $|R$ (GM, GR)$|_{min}$ = 0.97 |
| $n(GR_p) = n_7$ = 1.72916 | | $n(GR_n) = n_8$ = 1.92286 |
| $v(GR_p) = v_7$ = 54.68 | | $v(GR_n) = v_8$ = 18.90 |

As shown in FIG. 19, the optical system of Embodiment 19 is composed of: a front lens group that consists of a first lens component that has negative refractive power and is formed of a single lens element with lens surfaces having radii of curvature $r_3$ and $r_4$; a middle lens group that is composed of four lens components, specifically, second, third, fourth, and fifth lens components, each of which has positive refractive power and is formed of a single lens element with lens surfaces having radii of curvature $r_5$ and $r_6$, $r_7$ and $r_8$, $r_9$ and $r_{10}$, and $r_{11}$ and $r_{12}$, respectively; and a rear lens group composed of a cemented lens component formed of a biconvex lens element cemented to a meniscus lens element having negative refractive power with radii of curvature $r_{13}$, $r_{14}$, and $r_{15}$. Focusing from the far point to the near point is performed by moving the fourth lens component toward the image side, and a stop S for controlling image brightness is arranged on the object-side surface of the third lens component and has a radius of curvature $r_7$. A sapphire plane parallel plate C is arranged on the object side of the first lens component.

Embodiment 19 is an example of an optical system according to the first and third modes of construction of the present invention with the middle lens group, referenced by "GM" in Table 19 above and in FIG. 19, being composed of second, third, fourth, and fifth lens components having positive refractive power.

Embodiment 19 is very similar to Embodiment 17 in construction but in Embodiment 19 the fourth lens component moves for focusing.

Embodiment 19 of the present invention satisfies Conditions (1) through (7) above, as shown by Table 19 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. In Embodiment 19, the image side lens component that forms the rear lens group is a cemented lens component composed of a lens element having positive refractive power and a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 46A:
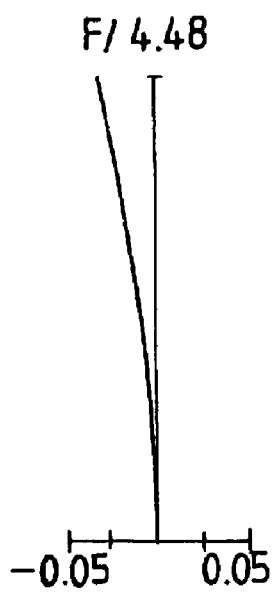
FIGS. 46A-46C show the spherical aberration, astigmatism, and distortion, respectively, of Embodiment 19 of the present invention when focused at the far point on the object side.
Figure 46B:
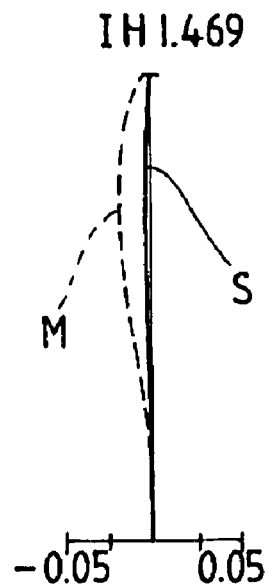
Figure 46C:
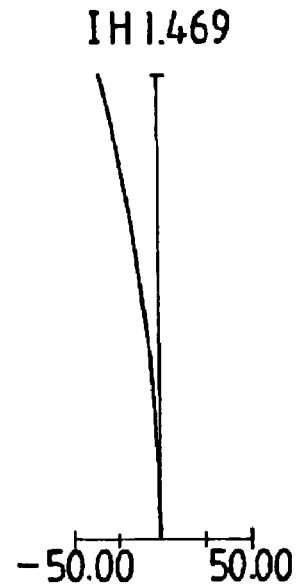
Figure 46D:
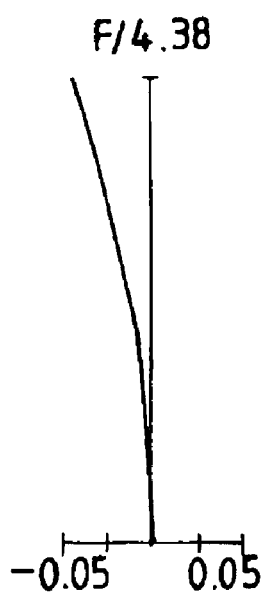
FIGS. 46D-46F show the spherical aberration, astigmatism, and distortion, respectively, of Embodiment 19 of the present invention when focused at the near point on the object side.
Figure 46E:
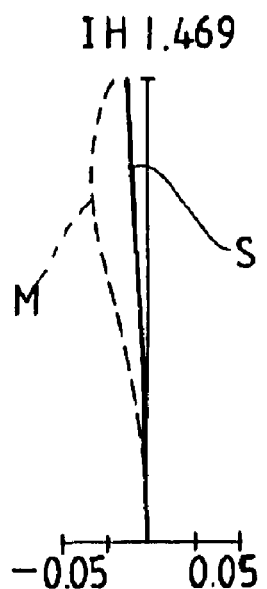
Figure 46F:
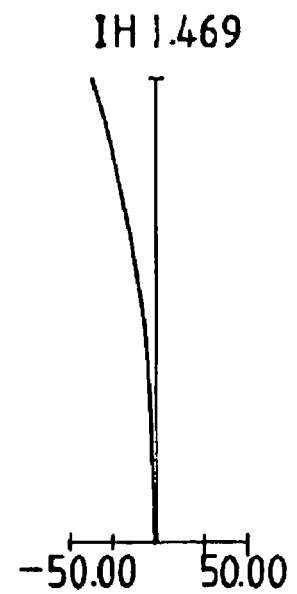

FIGS. 46A-46C show the spherical aberration, astigmatism, and distortion, respectively, of Embodiment 19 of the present invention when focused at the far point on the object side, and FIGS. 46D-46F show the spherical aberration, astigmatism, and distortion, respectively, of Embodiment 19 of the present invention when focused at the near point on the object side. As shown in FIGS. 46A-46C and FIGS. 46D-46F, in Embodiment 19 these aberrations are favorably corrected.

EMBODIMENT 20

Figure 20:
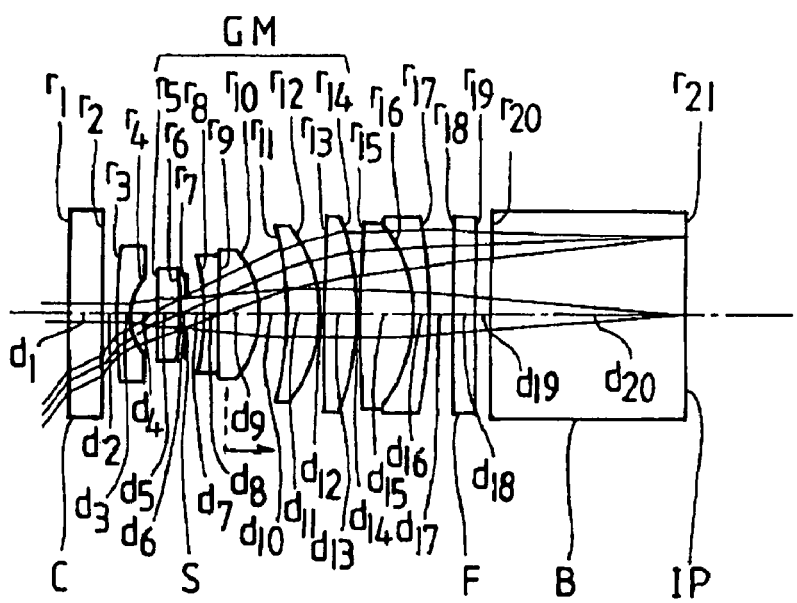
FIG. 20 is a cross-sectional view of Embodiment 20 of the present invention focused at the far point on the object side.

FIG. 20 shows a cross-sectional view of the objective optical system for an endoscope of Embodiment 20 of the present invention. Table 20 below lists the various data explained above for Embodiment 20.

TABLE 20

| Far point focused state | | | |
|---|---|---|---|
| WD = 45 | $f_{TF} = 1.740$ | $F_{NO} = 4.52$ | $2\omega = 104.1°$ |
| | Near point focused state | | |
| WD = 23 | $f_{TN} = 1.700$ | $F_{NO} = 4.42$ | $2\omega = 106.2°$ |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = 9.2269$ | $d_3 = 0.3000$ | $n_2 = 1.88300$ | $v_2 = 40.76$ |
| $r_4 = 1.0952$ | $d_4 = 0.5000$ | | |
| $r_5 = \infty$ | $d_5 = 0.4535$ | $n_3 = 1.92286$ | $v_3 = 18.90$ |
| $r_6 = -5.6726$ | $d_6 = 0.1000$ | | |
| $r_7 = \infty$ (stop) | $d_7 = 0.3867$ | | |
| $r_8 = -4.2341$ | $d_8 = 0.3000$ | $n_4 = 1.88300$ | $v_4 = 40.76$ |
| $r_9 = \infty$ | $d_9 = 0.8000$ | $n_5 = 1.51742$ | $v_5 = 52.43$ |
| $r_{10} = -1.8200$ | $d_{10} = 0.4852$ | | |
| $r_{11} = -6.9666$ | $d_{11} = 0.7000$ | $n_6 = 1.51742$ | $v_6 = 52.43$ |
| $r_{12} = -2.7028$ | $d_{12} = 0.1000$ | | |
| $r_{13} = \infty$ | $d_{13} = 0.6000$ | $n_7 = 1.71999$ | $v_7 = 50.23$ |
| $r_{14} = -6.3085$ | $d_{14} = 0.1000$ | | |
| $r_{15} = 26.7285$ | $d_{15} = 1.0700$ | $n_8 = 1.72916$ | $v_8 = 54.68$ |
| $r_{16} = -2.7215$ | $d_{16} = 0.3000$ | $n_9 = 1.92286$ | $v_9 = 18.90$ |
| $r_{17} = -7.9625$ | $d_{17} = 0.4748$ | | |
| $r_{18} = \infty$ | $d_{18} = 0.4500$ | $n_{10} = 1.51800$ | $v_{10} = 75.00$ |
| $r_{19} = \infty$ | $d_{19} = 0.3000$ | | |
| $r_{20} = \infty$ | $d_{20} = 3.9000$ | $n_{11} = 1.51633$ | $v_{11} = 64.14$ |
| $r_{21} = \infty$ (image plane) | | | |

| $|f_{UM}/f_{TF}| = 4.935$ | $f_{U1}/f_{TF} = -0.83$ | $f_{TN}/f_{TF} = 0.977$ |
|---|---|---|
| $f_{U1} = -1.432$ | | $f_{U1}/f_{TF} = -0.82$ |
| $f_{U2} = 6.147$ | | $f_{U2}/f_{TF} = 3.53$ |
| $f_{U3} = 8.587$ | | $f_{U3}/f_{TF} = 4.94$ |
| $f_{U4} = 8.082$ | | $f_{U4}/f_{TF} = 4.65$ |
| $f_{U5} = 8.762$ | | $f_{U5}/f_{TF} = 5.04$ |
| $f_{UR} = 13.884$ | | $f_{UR}/f_{TF} = 7.98$ |
| $|f_U (GM, GR)|_{min} = 3.69$ | | $|R (GM, GR)|_{min} = 1.05$ |
| $n(GR_p) = n_8 = 1.72916$ | | $n(GR_n) = n_9 = 1.92286$ |
| $v(GR_p) = v_8 = 54.68$ | | $v(GR_n) = v_9 = 18.90$ |

As shown in FIG. 20, the optical system of Embodiment 20 is composed of: a front lens group that consists of a first lens component that has negative refractive power and is formed of a single lens element with lens surfaces having radii of curvature $r_3$ and $r_4$; a middle lens group that is composed of four lens components, specifically, a second lens component that has positive refractive power and is formed of a single lens element with lens surfaces having radii of curvature $r_5$ and $r_6$, a cemented third lens component that is formed of a lens element having negative refractive power cemented to a lens element having positive refractive power and having radii of curvature $r_8$, $r_9$ and $r_{10}$, a fourth lens component that has positive refractive power and is formed of a single lens element and having radii of curvature $r_{11}$ and $r_{12}$, and a fifth lens component that has positive refractive power and is formed of a single lens element with lens surfaces having radii of curvature $r_{13}$ and $r_{14}$; and a rear lens group composed of a cemented lens component formed of a biconvex lens element cemented to a meniscus lens element having negative refractive power with radii of curvature $r_{15}$, $r_{16}$, and $r_{17}$. Focusing from the far point to the near point is performed by moving the third lens component toward the image side, and a stop S for controlling image brightness is arranged between the second lens component and the third lens component and has a radius of curvature $r_7$.

Embodiment 20 is an example of an optical system according to the first and third modes of construction of the present invention with the middle lens group, referenced by "GM" in Table 20 above and in FIG. 20, being composed of the second lens component having positive refractive power, third and fourth lens components, and the fifth lens component having positive refractive power.

Embodiment 20 is very similar to Embodiment 17 in construction but in Embodiment 20 the third lens component is a cemented lens component.

Embodiment 20 of the present invention satisfies Conditions (1) through (7) above, as shown by Table 20 above. The focal lengths $f_U(GM,GR)$ of the lens components in the middle lens group and rear lens group and the radii of curvature R(GM,GR) of the lens surfaces of the lens components in the middle lens group and rear lens group also satisfy the applicable conditions and design criteria specified for them. In Embodiment 20, the image side lens component that forms the rear lens group is a cemented lens component composed of a lens element having positive refractive power cemented to a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

FIGS. 47A-47C show the spherical aberration, astigmatism, and distortion, respectively, of Embodiment 20 of the present invention when focused at the far point on the object side, and FIGS. 47D-47F show the spherical aberration, astigmatism, and distortion, respectively, of Embodiment 20 of the present invention when focused at the near point on the object side. As shown in FIGS. 47A-47C and FIGS. 47D-47F, in Embodiment 20 these aberrations are favorably corrected.

EMBODIMENT 21

Figure 21:
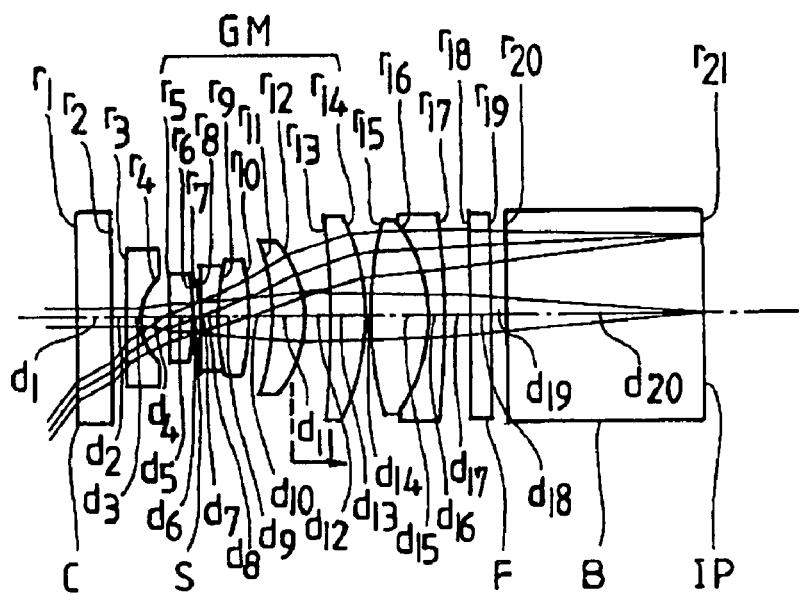
FIG. 21 is a cross-sectional view of Embodiment 21 of the present invention focused at the far point on the object side.

FIG. 21 shows a cross-sectional view of the objective optical system for an endoscope of Embodiment 21 of the present invention. Table 21 below lists the various data explained above for Embodiment 21.

TABLE 21

| Far point focused state | | | |
|---|---|---|---|
| WD = 48 | $f_{TF} = 1.760$ | $F_{NO} = 4.51$ | $2\omega = 104.0°$ |
| | Near point focused state | | |
| WD = 23 | $f_{TN} = 1.714$ | $F_{NO} = 4.41$ | $2\omega = 106.7°$ |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = 14.9688$ | $d_3 = 0.3000$ | $n_2 = 1.88300$ | $v_2 = 40.76$ |
| $r_4 = 1.1155$ | $d_4 = 0.5000$ | | |
| $r_5 = 8.0101$ | $d_5 = 0.5062$ | $n_3 = 1.84666$ | $v_3 = 23.78$ |
| $r_6 = -5.6893$ | $d_6 = 0.1000$ | | |
| $r_7 = \infty$ (stop) | $d_7 = 0.0800$ | | |
| $r_8 = -7.7719$ | $d_8 = 0.3000$ | $n_4 = 1.88300$ | $v_4 = 40.76$ |
| $r_9 = 4.4560$ | $d_9 = 0.6000$ | $n_5 = 1.51742$ | $v_5 = 52.43$ |
| $r_{10} = -4.3915$ | $d_{10} = 0.4318$ | | |
| $r_{11} = -4.5639$ | $d_{11} = 0.6800$ | $n_6 = 1.51742$ | $v_6 = 52.43$ |
| $r_{12} = -2.0715$ | $d_{12} = 0.4871$ | | |
| $r_{13} = -21.0210$ | $d_{13} = 0.7000$ | $n_7 = 1.88300$ | $v_7 = 40.76$ |
| $r_{14} = -4.2364$ | $d_{14} = 0.1000$ | | |
| $r_{15} = 7.6233$ | $d_{15} = 1.1500$ | $n_8 = 1.72916$ | $v_8 = 54.68$ |
| $r_{16} = -3.0536$ | $d_{16} = 0.3000$ | $n_9 = 1.92286$ | $v_9 = 18.90$ |
| $r_{17} = -16.0160$ | $d_{17} = 0.4868$ | | |

TABLE 21-continued

| | | | |
|---|---|---|---|
| $r_{18} = \infty$ | $d_{18} = 0.4500$ | $n_{10} = 1.51800$ | $v_{10} = 75.00$ |
| $r_{19} = \infty$ | $d_{19} = 0.3000$ | | |
| $r_{20} = \infty$ | $d_{20} = 3.9000$ | $n_{11} = 1.51633$ | $v_{11} = 64.14$ |
| $r_{21} = \infty$ (image plane) | | | |

| | | |
|---|---|---|
| $\|f_{UM}/f_{TF}\| = 3.811$ | $f_{U1}/f_{TF} = -0.784$ | $f_{TN}/f_{TF} = 0.974$ |

| | |
|---|---|
| $f_{U1} = -1.379$ | $f_{U1}/f_{TF} = -0.78$ |
| $f_{U2} = 3.997$ | $f_{U2}/f_{TF} = 2.27$ |
| $f_{U3} = -14.706$ | $f_{U3}/f_{TF} = -8.36$ |
| $f_{U4} = 6.707$ | $f_{U4}/f_{TF} = 3.81$ |
| $f_{U5} = 5.894$ | $f_{U5}/f_{TF} = 3.35$ |
| $f_{UR} = 11.126$ | $f_{UR}/f_{TF} = 6.32$ |
| $\|f_U (GM, GR)\|_{min} = 2.27$ | $\|R (GM, GR)\|_{min} = 1.18$ |
| $n(GR_p) = n_8 = 1.72916$ | $n(GR_n) = n_9 = 1.92286$ |
| $v(GR_p) = v_8 = 54.68$ | $v(GR_n) = v_9 = 18.90$ |

As shown in FIG. 21, the optical system of Embodiment 21 is composed of: a front lens group that consists of a first lens component that has negative refractive power and is formed of a single lens element with lens surfaces having radii of curvature $r_3$ and $r_4$; a middle lens group that is composed of four lens components, specifically, a second lens component that has positive refractive power and is formed of a single lens element with lens surfaces having radii of curvature $r_5$ and $r_6$, a cemented third lens component that is formed of a biconcave lens element cemented to a biconvex lens element and having radii of curvature $r_8$, $r_9$ and $r_{10}$, a fourth lens component of meniscus shape that has positive refractive power and is formed of a single lens element having radii of curvature $r_{11}$ and $r_{12}$, and a fifth lens component of meniscus shape that has positive refractive power and is formed of a single lens element with lens surfaces having radii of curvature $r_{13}$ and $r_{14}$; and a rear lens group composed of a cemented lens component formed of a biconvex lens element cemented to a meniscus lens element having negative refractive power with radii of curvature $r_{15}$, $r_{16}$, and $r_{17}$. Focusing from the far point to the near point is performed by moving the fourth lens component toward the image side, and a stop S for controlling image brightness is arranged between the second lens component and the third lens component and has a radius of curvature $r_7$.

Embodiment 21 is an example of an optical system according to the first and third modes of construction of the present invention with the middle lens group, referenced by "GM" in Table 21 above and in FIG. 21, being composed of the second lens component having positive refractive power, third and fourth lens components, and the fifth lens component having positive refractive power.

Embodiment 21 is very similar to Embodiment 16 in construction but in Embodiment 21 the third lens component is a cemented lens component.

Embodiment 21 of the present invention satisfies Conditions (1) through (7) above, as shown by Table 21 above. The focal lengths $f_U(GM,GR)$ of the lens components in the middle lens group and rear lens group and the radii of curvature R(GM,GR) of the lens surfaces of the lens components in the middle lens group and rear lens group also satisfy the applicable conditions and design criteria specified for them. In Embodiment 21, the image side lens component that forms the rear lens group is a cemented lens component composed of a lens element having positive refractive power cemented to a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 48A:
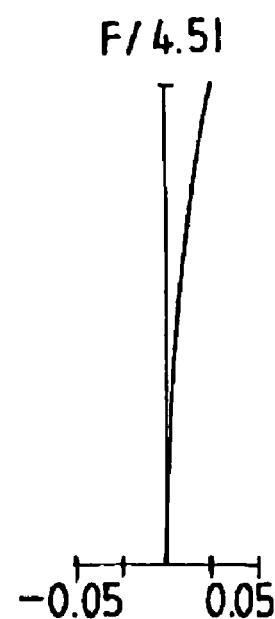
FIGS. 48A-48C show the spherical aberration, astigmatism, and distortion, respectively, of Embodiment 21 of the present invention when focused at the far point on the object side.
Figure 48B:
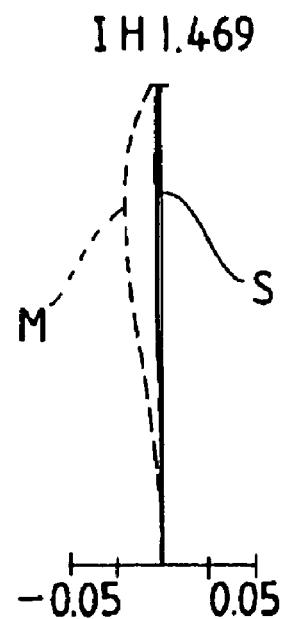
Figure 48C:
Figure 48D:
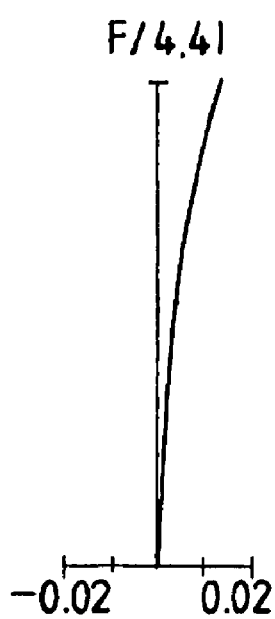
FIGS. 48D-48F show the spherical aberration, astigmatism, and distortion, respectively, of Embodiment 21 of the present invention when focused at the near point on the object side.
Figure 48E:
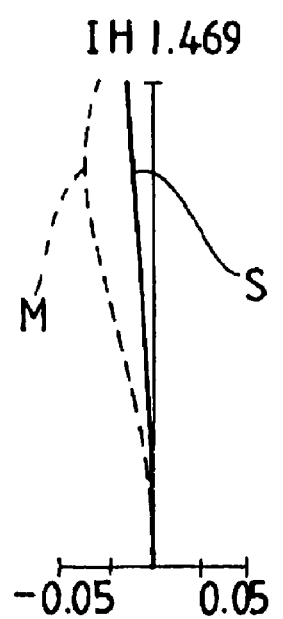
Figure 48F:
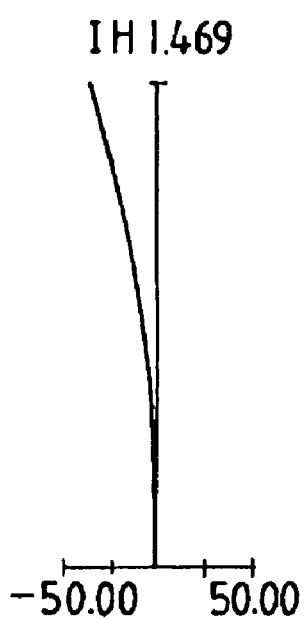

FIGS. 48A-48C show the spherical aberration, astigmatism, and distortion, respectively, of Embodiment 21 of the present invention when focused at the far point on the object side, and FIGS. 48D-48F show the spherical aberration, astigmatism, and distortion, respectively, of Embodiment 21 of the present invention when focused at the near point on the object side. As shown in FIGS. 48A-48C and FIGS. 48D-48F, in Embodiment 21 these aberrations are favorably corrected.

EMBODIMENT 22

Figure 22:
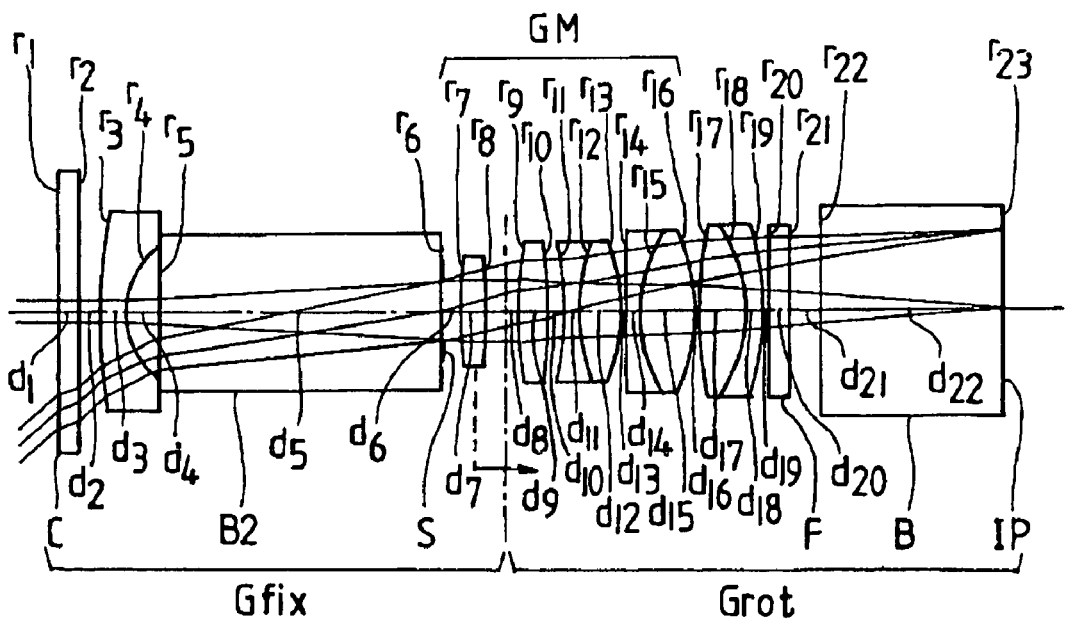
FIG. 22 is a cross-sectional view of Embodiment 22 of the present invention focused at the far point on the object side.

FIG. 22 shows a cross-sectional view of the objective optical system for an endoscope of Embodiment 22 of the present invention. Table 22 below lists the various data explained above for Embodiment 22.

The object-side surface of the first lens component of Embodiment 22 is an aspheric surface expressed by the following equation:

$$Z = \frac{Y^2 R}{1 + \{1 - (K+1) \cdot (Y/R)^2\}^{-1/2}} + \sum_{n=2}^{10} (A_{2n} \cdot Y^{2n}) \qquad \text{Equation (A)}$$

where
Z is the length (in mm) of a line drawn from a point on the aspheric lens surface at a distance Y from the optical axis to the tangential plane of the aspheric surface vertex,
R is the radius of curvature (in mm) of the aspheric lens surface on the optical axis,
Y is the distance (in mm) from the optical axis,
K is the eccentricity, and
$A_{2n}$ is the ith aspheric coefficient and the summation extends over 2n from n equals two to ten.

In Embodiment 22 of the present invention, only aspheric coefficients $A_4$, $A_6$, and $A_8$ are non-zero. These non-zero values and other values related to Equation (A) above with regard to the lens surface with radius of curvature $r_3$ above are shown in the middle of Table 22 below.

TABLE 22

| Far point focused state | | | |
|---|---|---|---|
| WD = 48 | $f_{TF} = 1.804$ | $F_{NO} = 4.48$ | $2\omega = 82.0°$ |
| Near point focused state | | | |
| WD = 22.5 | $f_{TN} = 1.764$ | $F_{NO} = 4.40$ | $2\omega = 83.4°$ |
| $r_1 = \infty$ | $d_1 = 0.4000$ | $n_1 = 1.76820$ | $v_1 = 71.79$ |
| $r_2 = \infty$ | $d_2 = 0.5000$ | | |
| $r_3 = 100$ (aspheric) | $d_3 = 0.5000$ | $n_2 = 1.80610$ | $v_2 = 40.88$ |
| $r_4 = 1.6055$ | $d_4 = 0.6500$ | | |
| $r_5 = \infty$ | $d_5 = 5.5000$ | $n_3 = 1.88300$ | $v_3 = 40.76$ |
| $r_6 = \infty$ (stop) | $d_6 = 0.4000$ | | |
| $r_7 = 8.6334$ | $d_7 = 0.5000$ | $n_4 = 1.88300$ | $v_4 = 40.76$ |
| $r_8 = -8.6334$ | $d_8 = 0.6347$ | | |
| $r_9 = 6.1623$ | $d_9 = 0.6000$ | $n_5 = 1.80100$ | $v_5 = 34.97$ |
| $r_{10} = -10.9223$ | $d_{10} = 0.3398$ | | |
| $r_{11} = -5.3215$ | $d_{11} = 0.3000$ | $n_6 = 1.88300$ | $v_6 = 40.76$ |
| $r_{12} = 3.8000$ | $d_{12} = 0.8500$ | $n_7 = 1.48749$ | $v_7 = 70.23$ |
| $r_{13} = -3.4079$ | $d_{13} = 0.1230$ | | |
| $r_{14} = 50.0407$ | $d_{14} = 0.3000$ | $n_8 = 1.88300$ | $v_8 = 40.76$ |
| $r_{15} = 2.9659$ | $d_{15} = 1.0500$ | $n_9 = 1.48749$ | $v_9 = 70.23$ |
| $r_{16} = -3.8154$ | $d_{16} = 0.1000$ | | |
| $r_{17} = 7.9926$ | $d_{17} = 0.9500$ | $n_{10} = 1.48749$ | $v_{10} = 70.23$ |
| $r_{18} = -2.6500$ | $d_{18} = 0.3000$ | $n_{11} = 1.84666$ | $v_{11} = 23.78$ |

TABLE 22-continued

| | | | |
|---|---|---|---|
| $r_{19} = -5.6345$ | $d_{19} = 0.1000$ | | |
| $r_{20} = \infty$ | $d_{20} = 0.4500$ | $n_{12} = 1.51800$ | $v_{12} = 75.00$ |
| $r_{21} = \infty$ | $d_{21} = 0.6000$ | | |
| $r_{22} = \infty$ | $d_{22} = 3.6000$ | $n_{13} = 1.48749$ | $v_{13} = 70.23$ |
| $r_{23} = \infty$ (image plane) | | | |

$R = r_3 = 100 \quad K = 0$
$A_4 = 1.8935 \times 10^{-2}$
$A_6 = -3.9808 \times 10^{-3}$
$A_8 = 5.5246 \times 10^{-4}$

| $|f_{UM}/f_{TF}| = 2.747$ | $f_{U1}/f_{TF} = -1.125$ | $f_{TN}/f_{TF} = 0.978$ |
|---|---|---|

| | |
|---|---|
| $f_{U1} = -2.029$ | $f_{U1}/f_{TF} = -1.13$ |
| $f_{U2} = 4.956$ | $f_{U2}/f_{TF} = 2.75$ |
| $f_{U3} = 4.996$ | $f_{U3}/f_{TF} = 2.77$ |
| $f_{U4} = -9.649$ | $f_{U4}/f_{TF} = -5.35$ |
| $f_{U5} = 44.483$ | $f_{U5}/f_{TF} = 24.66$ |
| $f_{UR} = 13.015$ | $f_{UR}/f_{TF} = 7.22$ |
| $|f_U (GM, GR)|_{min} = 2.75$ | $|R (GM, GR)|_{min} = 1.47$ |
| $n(GR_p) = n_{10} = 1.48749$ | $n(GR_n) = n_{11} = 1.84666$ |
| $v(GR_p) = v_{10} = 70.23$ | $v(GR_n) = v_{11} = 23.78$ |

As shown in FIG. 22, the optical system of Embodiment 22 is composed of: a front lens group that consists of a first lens component that has negative refractive power and is formed of a single lens element with lens surfaces having radii of curvature $r_3$ and $r_4$; a middle lens group that is composed of four lens components, specifically, second and third lens components that have positive refractive power and are each formed of a single lens element with lens surfaces having radii of curvature ($r_7$ and $r_8$) and ($r_9$ and $r_{10}$) respectively, and cemented fourth and fifth lens components, each of which is formed of a biconcave lens element cemented to a biconvex lens element and having radii of curvature ($r_{11}$, $r_{12}$ and $r_{13}$) and ($r_{14}$, $r_{15}$ and $r_{16}$), respectively; and a rear lens group composed of a cemented lens component formed of a biconvex lens element cemented to a meniscus lens element having negative refractive power with radii of curvature $r_{17}$, $r_{18}$, and $r_{19}$.

Embodiment 22 is an example of an optical system according to the first and third modes of construction of the present invention with the middle lens group, referenced by "GM" in Table 22 above and in FIG. 22, being composed of the second lens component having positive refractive power, third and fourth lens components, and the fifth lens component having positive refractive power.

Embodiment 22 is designed for use in a videoscope that includes an oblique view. Therefore, Embodiment 22 has a narrower field of view than in Embodiments 1-21. However, astigmatism is reduced by using an aspheric surface at the object-side surface with radius of curvature $r_3$ of the first lens component so that it embodies an optical system with a focal length that is nearly the same as in Embodiments 1-21, described above.

In Embodiment 22, a stop S for controlling image brightness and having a radius of curvature $r_6$ is arranged between the first lens component and the second lens component, and a glass block B2 having radii of curvature $r_5$ and $r_6$ and having a long glass length is arranged between the first lens component and the stop S. Additionally, Embodiment 22 can be made into an objective optical system with an oblique view by changing this glass block into an oblique viewing prism.

In Embodiment 22, when it is used in a videoscope with an oblique view, for example, a videoscope being used in endoscope surgery, a rotating mechanism for rotating a monitor picture in the direction of observation for the convenience of visual field viewing becomes necessary.

In Embodiment 22, the objective optical system is divided between the second lens component and the third lens component as shown in FIG. 22 so as to define on the object side a fixed lens group $G_{fix}$ and on the image side a rotational lens group Got, as indicated by brackets at the bottom of FIG. 22. The fixed lens group $G_{fix}$ is fixed in an insertion part, and the rotational lens group $G_{rot}$ is constructed so as to be rotatable in the insertion part. In this case, the rotation of the monitor picture is made possible only by rotating a solid-state image pickup element, but this is undesirable because image quality problems, such as focus deviation, occur during rotation. Moreover, the division of the fixed lens group $G_{fix}$ and the rotational lens group $G_{rot}$ at a position where the light in the light path is nearly a focal, as illustrated, is desirable.

In Embodiment 22, the second lens component that is on the image side end of the fixed lens group $G_{fix}$ and that is in the middle group is used as the lens component that is moved for focusing, and an actuator for moving this lens component is fixed and arranged in the insertion part.

Embodiment 22 of the present invention satisfies Conditions (1) through (7) above, as shown by Table 22 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. In Embodiment 22, the image side lens component that forms the rear lens group is a cemented lens component composed of a lens element having positive refractive power cemented to a lens element having negative refractive power, and, as described above, the refractive indices n($GR_p$) and n($GR_n$) and the Abbe numbers v($GR_p$) and v($GR_n$) of the lens materials of the cemented lens component that is the last lens component satisfy the applicable conditions and design criteria of the present invention.

Figure 49A:
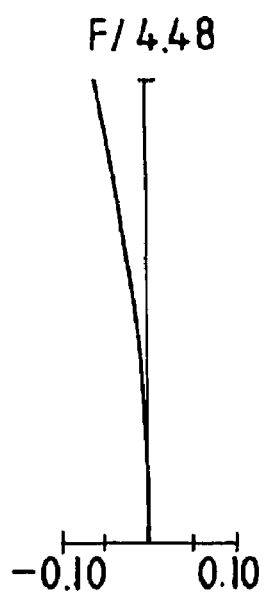
FIGS. 49A-49C show the spherical aberration, astigmatism, and distortion, respectively, of Embodiment 22 of the present invention when focused at the far point on the object side.
Figure 49B:
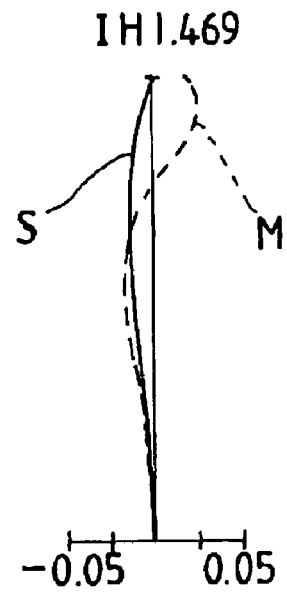
Figure 49C:
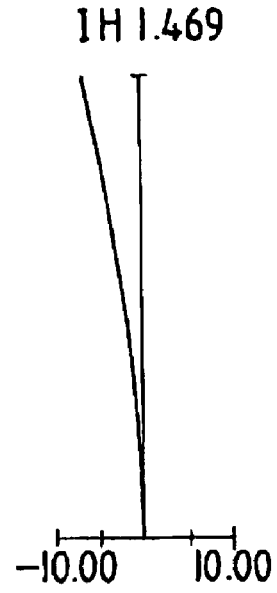
Figure 49D:
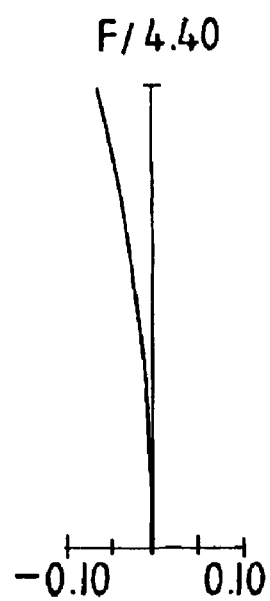
FIGS. 49D-49F show the spherical aberration, astigmatism, and distortion, respectively, of Embodiment 22 of the present invention when focused at the near point on the object side.
Figure 49E:
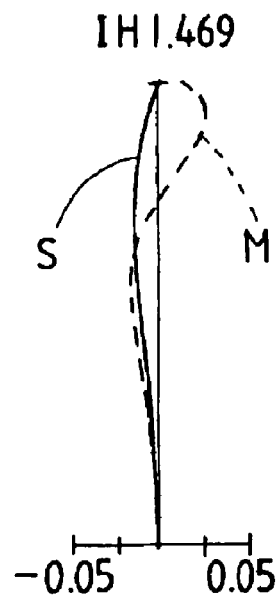
Figure 49F:
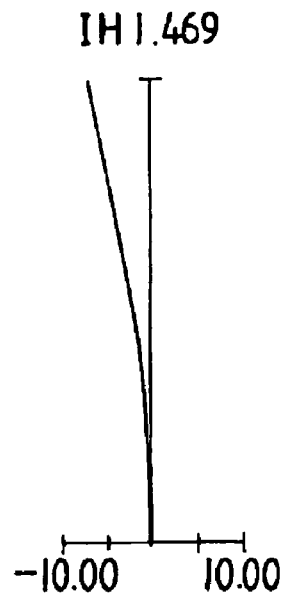

FIGS. 49A-49C show the spherical aberration, astigmatism, and distortion, respectively, of Embodiment 22 of the present invention when focused at the far point on the object side, and FIGS. 49D-49F show the spherical aberration, astigmatism, and distortion, respectively, of Embodiment 22 of the present invention when focused at the near point on the object side. As shown in FIGS. 49A-49C and FIGS. 49D-49F, in Embodiment 22 these aberrations are favorably corrected.

EMBODIMENT 23

Figure 23:
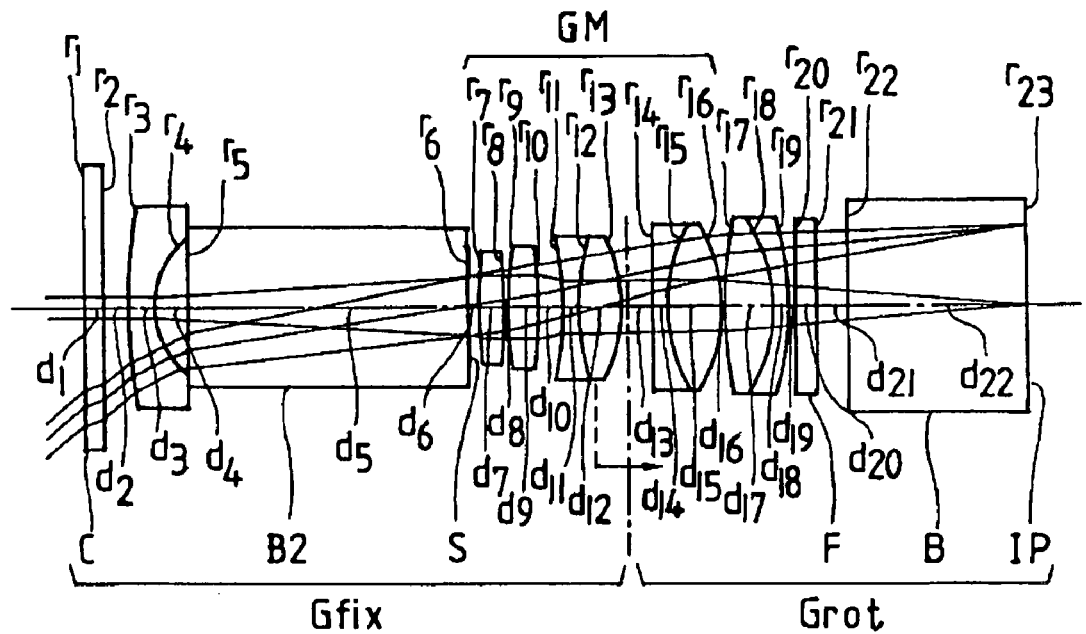
FIG. 23 is a cross-sectional view of Embodiment 23 of the present invention focused at the far point on the object side.

FIG. 23 shows a cross-sectional view of the objective optical system for an endoscope of Embodiment 23 of the present invention. Table 23 below lists the various data explained above for Embodiment 23.

The object-side surface of the first lens component of Embodiment 23 is an aspheric surface expressed by Equation (A) described above with regard to Embodiment 22. In Embodiment 23 of the present invention, only aspheric coefficients $A_4$, $A_6$, and $A_8$ are non-zero. These non-zero values and other values related to Equation (A) above with regard to the lens surface with radius of curvature $r_3$ are shown in the middle of Table 23 below.

TABLE 23

| | Far point focused state | | |
|---|---|---|---|
| WD = 48 | $f_{TF} = 1.804$ | $F_{NO} = 4.48$ | $2\omega = 82.0°$ |
| | Near point focused state | | |
| WD = 22.5 | $f_{TN} = 1.808$ | $F_{NO} = 4.51$ | $2\omega = 81.4°$ |
| $r_1 = \infty$ | $d_1 = 0.4000$ | $n_1 = 1.76820$ | $v_1 = 71.79$ |
| $r_2 = \infty$ | $d_2 = 0.5000$ | | |
| $r_3 = 100$ (aspheric) | $d_3 = 0.5000$ | $n_2 = 1.80610$ | $v_2 = 40.88$ |

TABLE 23-continued

| | | | |
|---|---|---|---|
| $r_4 = 1.6090$ | $d_4 = 0.6500$ | | |
| $r_5 = \infty$ | $d_5 = 5.5000$ | $n_3 = 1.88300$ | $v_3 = 40.76$ |
| $r_6 = \infty$ (stop) | $d_6 = 0.2000$ | | |
| $r_7 = 9.7009$ | $d_7 = 0.5000$ | $n_4 = 1.88300$ | $v_4 = 40.76$ |
| $r_8 = -9.7009$ | $d_8 = 0.1000$ | | |
| $r_9 = 9.0734$ | $d_9 = 0.6000$ | $n_5 = 1.80100$ | $v_5 = 34.97$ |
| $r_{10} = -8.8591$ | $d_{10} = 0.4834$ | | |
| $r_{11} = -5.8965$ | $d_{11} = 0.3000$ | $n_6 = 1.88300$ | $v_6 = 40.76$ |
| $r_{12} = 4.1000$ | $d_{12} = 0.8500$ | $n_7 = 1.48749$ | $v_7 = 70.23$ |
| $r_{13} = -3.2639$ | $d_{13} = 0.6026$ | | |
| $r_{14} = -241.5149$ | $d_{14} = 0.3000$ | $n_8 = 1.88300$ | $v_8 = 40.76$ |
| $r_{15} = 3.0356$ | $d_{15} = 1.0500$ | $n_9 = 1.58913$ | $v_9 = 61.14$ |
| $r_{16} = -3.6847$ | $d_{16} = 0.1000$ | | |
| $r_{17} = 9.8915$ | $d_{17} = 0.9500$ | $n_{10} = 1.48749$ | $v_{10} = 70.23$ |
| $r_{18} = -2.6760$ | $d_{18} = 0.3000$ | $n_{11} = 1.84666$ | $v_{11} = 23.78$ |
| $r_{19} = -5.9533$ | $d_{19} = 0.1000$ | | |
| $r_{20} = \infty$ | $d_{20} = 0.4500$ | $n_{12} = 1.51800$ | $v_{12} = 75.00$ |
| $r_{21} = \infty$ | $d_{21} = 0.6000$ | | |
| $r_{22} = \infty$ | $d_{22} = 3.6000$ | $n_{13} = 1.48749$ | $v_{13} = 70.23$ |
| $r_{23} = \infty$ (image plane) | | | |

$R = r_3 = 100 \; K = 0$
$A_4 = 1.9065 \times 10^{-2}$
$A_6 = -4.2103 \times 10^{-3}$
$A_8 = 6.1429 \times 10^{-4}$

| | | |
|---|---|---|
| $|f_{UM}/f_{TF}| = 7.452$ | $f_{U1}/f_{TF} = -1.127$ | $f_{TN}/f_{TF} = 1.002$ |

| | |
|---|---|
| $f_{U1} = -2.033$ | $f_{U1}/f_{TF} = -1.13$ |
| $f_{U2} = 5.560$ | $f_{U2}/f_{TF} = 3.08$ |
| $f_{U3} = 5.681$ | $f_{U3}/f_{TF} = 3.15$ |
| $f_{U4} = -13.443$ | $f_{U4}/f_{TF} = -7.45$ |
| $f_{U5} = 14.270$ | $f_{U5}/f_{TF} = 7.91$ |
| $f_{UR} = 16.980$ | $f_{UR}/f_{TF} = 9.41$ |
| $|f_U (GM, GR)|_{min} = 3.08$ | $|R (GM, GR)|_{min} = 1.48$ |
| $n(GR_p) = n_{10} = 1.48749$ | $n(GR_n) = n_{11} = 1.84666$ |
| $v(GR_p) = v_{10} = 70.23$ | $v(GR_n) = v_{11} = 23.78$ |

Embodiment 23 is designed for use in a videoscope that includes an oblique view, similar to Embodiment 22 described above.

Embodiment 23 is an example of an optical system according to the first and third modes of construction of the present invention with the middle lens group, referenced by "GM" in Table 23 above and in FIG. 23, being composed of the second lens component having positive refractive power, third and fourth lens components, and the fifth lens component being a cemented lens component having positive refractive power.

Embodiment 23 is different from Embodiment 22 in that in Embodiment 23 the fourth lens component is moved for focusing, and that movement is toward the image side.

When the objective optical system of Embodiment 23 is used for oblique viewing and divided into a fixed lens group $G_{fix}$ that is fixed in the insertion part of the endoscope and a rotational lens group $G_{rot}$, the optical system is divided between the fourth lens component and the fifth lens component, as illustrated in FIG. 23, with the fixed lens group $G_{fix}$ on the object side and the rotational lens group $G_{rot}$ on the image side, as indicated by brackets at the bottom of FIG. 23. Then, an image can be rotated by rotating the rotational group $G_{rot}$ around the insertion part. The fourth lens component is the lens component that is moved for focusing and, as in Embodiment 22, it forms part of the fixed lens group $G_{fix}$. Therefore, an actuator for moving the focusing lens component is fixed and arranged in the insertion part.

Embodiment 23 of the present invention satisfies Conditions (1) through (7) above, as shown by Table 23 above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. In Embodiment 23, the image side lens component that forms the rear lens group is a cemented lens component composed of a lens element having positive refractive power cemented to a lens element having negative refractive power, and, as described above, the refractive indices $n(GR_p)$ and $n(GR_n)$ and the Abbe numbers $v(GR_p)$ and $v(GR_n)$ of the lens materials of the cemented lens component that is the last lens component satisfy the applicable conditions and design criteria of the present invention.

Figure 50A:
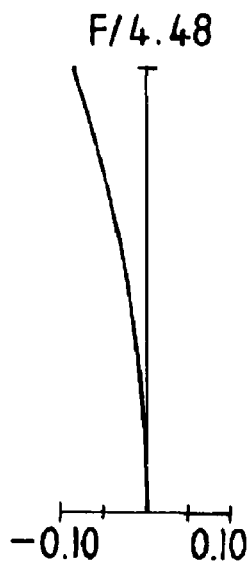
FIGS. 50A-50C show the spherical aberration, astigmatism, and distortion, respectively, of Embodiment 23 of the present invention when focused at the far point on the object side.
Figure 50B:
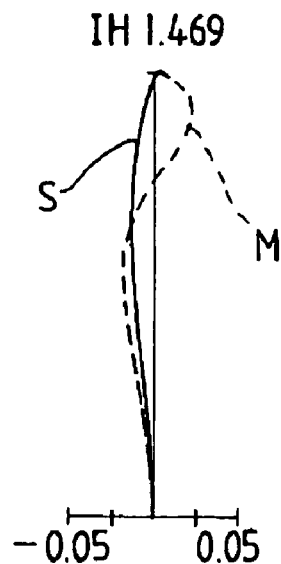
Figure 50C:
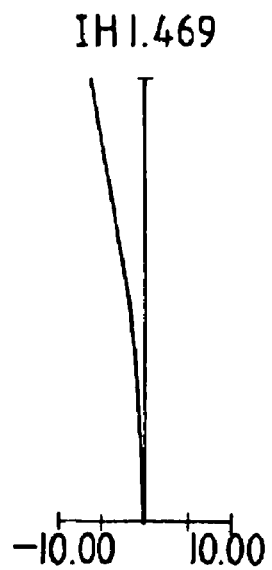
Figure 50D:
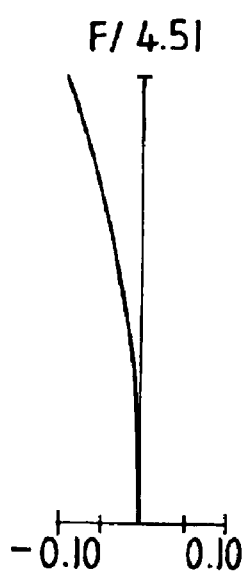
FIGS. 50D-50F show the spherical aberration, astigmatism, and distortion, respectively, of Embodiment 23 of the present invention when focused at the near point on the object side.
Figure 50E:
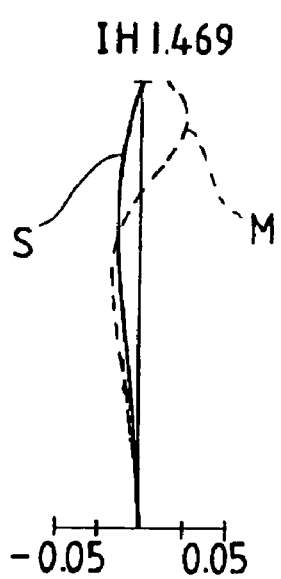
Figure 50F:
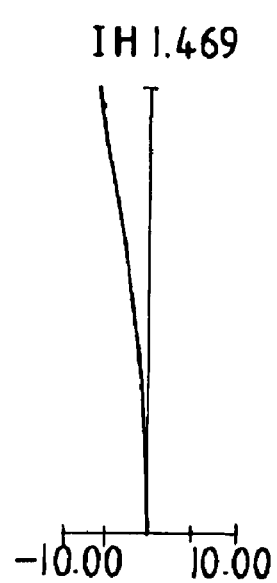

FIGS. 50A-50C show the spherical aberration, astigmatism, and distortion, respectively, of Embodiment 23 of the present invention when focused at the far point on the object side, and FIGS. 50D-50F show the spherical aberration, astigmatism, and distortion, respectively, of Embodiment 23 of the present invention when focused at the near point on the object side. As shown in FIGS. 50A-50C and FIGS. 50D-50F, in Embodiment 23 these aberrations are favorably corrected.

EMBODIMENT 24

Figure 24:
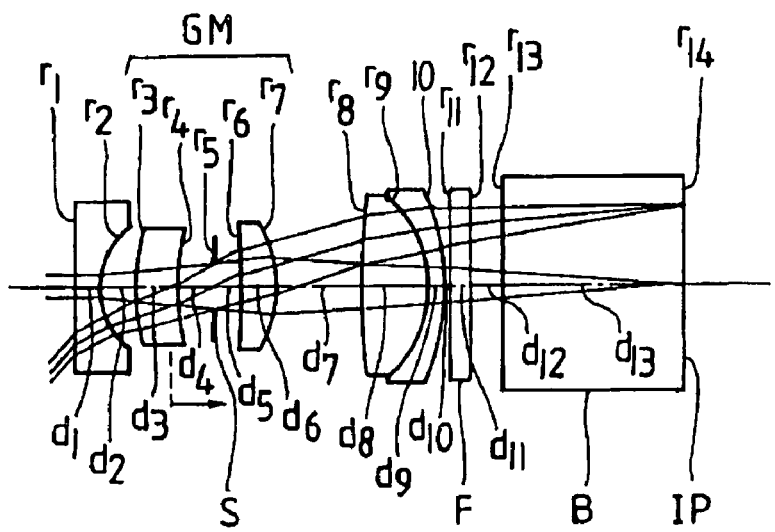
FIG. 24 is a cross-sectional view of Embodiment 24 of the present invention focused at the far point on the object side.

FIG. 24 shows a cross-sectional view of the objective optical system for an endoscope of Embodiment 24 of the present invention. Table 24 below lists the various data explained above for Embodiment 24.

TABLE 24

| Far point focused state | | | |
|---|---|---|---|
| WD = 46 | $f_{TF} = 1.900$ | $F_{NO} = 4.51$ | $2\omega = 98.6°$ |
| | Near point focused state | | |
| WD = 23 | $f_{TN} = 1.898$ | $F_{NO} = 4.51$ | $2\omega = 97.2°$ |

| | | | |
|---|---|---|---|
| $r_1 = \infty$ | $d_1 = 0.5000$ | $n_1 = 1.76820$ | $v_1 = 71.79$ |
| $r_2 = 1.3668$ | $d_2 = 0.6677$ | | |
| $r_3 = 3.0512$ | $d_3 = 0.8469$ | $n_2 = 1.59270$ | $v_2 = 35.31$ |
| $r_4 = 4.1365$ | $d_4 = 0.7515$ | | |
| $r_5 = \infty$ (stop) | $d_5 = 0.4801$ | | |
| $r_6 = -35.9069$ | $d_6 = 0.7000$ | $n_3 = 1.77250$ | $v_3 = 49.60$ |
| $r_7 = -2.3945$ | $d_7 = 1.6607$ | | |
| $r_8 = 12.3406$ | $d_8 = 1.3500$ | $n_4 = 1.71999$ | $v_4 = 50.23$ |
| $r_9 = -2.1108$ | $d_9 = 0.3000$ | $n_5 = 1.92286$ | $v_5 = 18.90$ |
| $r_{10} = -4.3910$ | $d_{10} = 0.1000$ | | |
| $r_{11} = \infty$ | $d_{11} = 0.4500$ | $n_6 = 1.51800$ | $v_6 = 75.00$ |
| $r_{12} = \infty$ | $d_{12} = 0.6000$ | | |
| $r_{13} = \infty$ | $d_{13} = 3.6000$ | $n_7 = 1.48749$ | $v_7 = 70.23$ |
| $r_{14} = \infty$ (image plane) | | | |

| | | |
|---|---|---|
| $|f_{UM}/f_{TF}| = 8.003$ | $f_{U1}/f_{TF} = -0.936$ | $f_{TN}/f_{TF} = 0.999$ |

| | |
|---|---|
| $f_{U1} = -1.779$ | $f_{U1}/f_{TF} = -0.94$ |
| $f_{U2} = 15.206$ | $f_{U2}/f_{TF} = 8.00$ |
| $f_{U3} = 3.291$ | $f_{U3}/f_{TF} = 1.73$ |
| $f_{UR} = 5.943$ | $f_{UR}/f_{TF} = 3.13$ |
| $|f_U (GM, GR)|_{min} = 1.73$ | $|R (GM, GR)|_{min} = 1.11$ |
| $n(GR_p) = n_4 = 1.71999$ | $n(GR_n) = n_5 = 1.92286$ |
| $v(GR_p) = v_4 = 50.23$ | $v(GR_n) = v_5 = 18.90$ |

The optical system of Embodiment 24, as shown in FIG. 24, is composed of: a front lens group that consists of a first lens component that has negative refractive power and is formed of a single lens element with lens surfaces having radii of curvature $r_1$ and $r_2$; a middle lens group that is composed of two lens components, specifically, second and third lens components that have positive refractive power and are each formed of a single lens element with lens surfaces having radii of curvature ($r_3$ and $r_4$) and ($r_6$ and $r_7$), respectively; and a rear lens group composed of a fourth cemented lens component formed of a biconvex lens element cemented to a meniscus lens element having negative refractive power with radii of curvature $r_8$, $r_9$ and $r_{10}$. A stop S for controlling image brightness and having a radius of curvature $r_5$ is arranged between the second lens component and the third lens component in the middle lens group at a position providing a lower ray height. In Embodiment 24, the second lens component is the lens component that moves for focusing and it moves toward the image side during focusing from the far point to the near point.

Embodiment 24 is an example of an optical system according to the fourth mode of construction of the present invention described above with regard to the middle lens group, referenced by "GM" in Table 24 above and in FIG. 24, and is composed of second and third lens components, each of which is formed as a single lens element.

The fourth or rear lens component is formed as a cemented lens component in order to correct astigmatism and lateral color.

Embodiment 24 has a longer far point focal length $f_{TF}$ than Embodiments 1-23 above, and has relatively large astigmatism resulting in unfavorable depth of field, but operates satisfactorily when in use.

Embodiment 24 of the present invention satisfies Conditions (1) through (7) above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. As described above, the refractive indices $n(GR_p)$ and $n(GR_n)$ and the Abbe numbers $v(GR_p)$ and $v(GR_n)$ of the lens materials of the cemented lens component that is the last lens component also satisfy the applicable conditions and design criteria of the present invention.

FIGS. 51A-51C show the spherical aberration, astigmatism, and distortion, respectively, of Embodiment 24 of the present invention when focused at the far point on the object side, and FIGS. 51D-51F show the spherical aberration, astigmatism, and distortion, respectively, of Embodiment 24 of the present invention when focused at the near point on the object side. As shown in FIGS. 51A-51C and FIGS. 51D-51F, in Embodiment 24 these aberrations are favorably corrected.

EMBODIMENT 25

Figure 25:
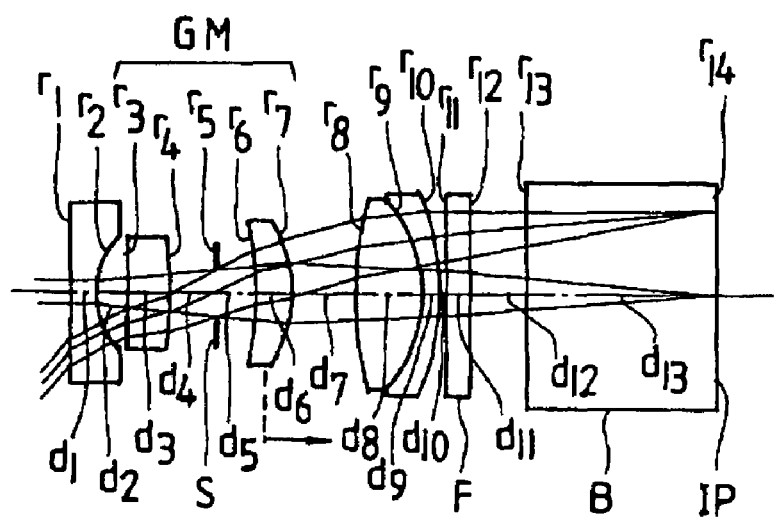
FIG. 25 is a cross-sectional view of Embodiment 25 of the present invention focused at the far point on the object side.

FIG. 25 shows a cross-sectional view of the objective optical system for an endoscope of Embodiment 25 of the present invention. Table 25 below lists the various data explained above for Embodiment 25.

TABLE 25

| Far point focused state | | | |
|---|---|---|---|
| WD = 46 | $f_{TF} = 1.900$ | $F_{NO} = 4.51$ | $2\omega = 98.6°$ |
| | Near point focused state | | |
| WD = 23 | $f_{TN} = 1.833$ | $F_{NO} = 4.37$ | $2\omega = 102.6°$ |
| $r_1 = \infty$ | $d_1 = 0.5000$ | $n_1 = 1.76820$ | $v_1 = 71.79$ |
| $r_2 = 1.3870$ | $d_2 = 0.5500$ | | |
| $r_3 = 29.8167$ | $d_3 = 0.8000$ | $n_2 = 1.74077$ | $v_2 = 27.79$ |
| $r_4 = -11.0393$ | $d_4 = 0.8931$ | | |
| $r_5 = \infty$ (stop) | $d_5 = 0.7281$ | | |
| $r_6 = -6.1867$ | $d_6 = 0.7000$ | $n_3 = 1.72916$ | $v_3 = 54.68$ |
| $r_7 = -2.2463$ | $d_7 = 1.1458$ | | |
| $r_8 = 5.2651$ | $d_8 = 1.3000$ | $n_4 = 1.58913$ | $v_4 = 61.14$ |
| $r_9 = -2.4546$ | $d_9 = 0.3000$ | $n_5 = 1.92286$ | $v_5 = 18.90$ |
| $r_{10} = -4.5363$ | $d_{10} = 0.1000$ | | |
| $r_{11} = \infty$ | $d_{11} = 0.4500$ | $n_6 = 1.51800$ | $v_6 = 75.00$ |
| $r_{12} = \infty$ | $d_{12} = 1.0729$ | | |

TABLE 25-continued

| $r_{13} = \infty$ | $d_{13} = 3.6000$ | $n_7 = 1.48749$ | $v_7 = 70.23$ |
|---|---|---|---|
| $r_{14} = \infty$ (image plane) | | | |
| $|f_{UM}/f_{TF}| = 2.368$ | $f_{U1}/f_{TF} = -0.951$ | | $f_{TN}/f_{TF} = 0.965$ |
| $f_{U1} = -1.806$ | | $f_{U1}/f_{TF} = -0.95$ | |
| $f_{U2} = 10.967$ | | $f_{U2}/f_{TF} = 5.77$ | |
| $f_{U3} = 4.500$ | | $f_{U3}/f_{TF} = 2.37$ | |
| $f_{UR} = 5.762$ | | $f_{UR}/f_{TF} = 3.03$ | |
| $|f_U (GM, GR)|_{min} = 2.37$ | | $|R (GM, GR)|_{min} = 1.18$ | |
| $n(GR_p) = n_4 = 1.58913$ | | $n(GR_n) = n_5 = 1.92286$ | |
| $v(GR_p) = v_4 = 61.14$ | | $v(GR_n) = v_5 = 18.90$ | |

Embodiment 25 is an optical system that is similar to Embodiment 24, but in Embodiment 25 the lens component that moves for focusing is the third lens component and it moves toward the image side during focusing from the far point to the near point. Thus, Embodiment 25 is also, as with Embodiment 24, an example of an optical system according to the fourth mode of construction of the present invention described above.

Embodiment 25 of the present invention satisfies Conditions (1) through (7) above. The focal lengths $f_U$(GM,GR) of the lens components in the middle lens group and rear lens group and the radii of curvature R(GM,GR) of the lens surfaces of the lens components in the middle lens group and rear lens group also satisfy the applicable conditions and design criteria specified for them. As described above, the refractive indices $n(GR_p)$ and $n(GR_n)$ and the Abbe numbers $v(GR_p)$ and $v(GR_n)$ of the lens materials of the cemented lens component that is the last lens component also satisfy the applicable conditions and design criteria of the present invention.

Figure 52A:
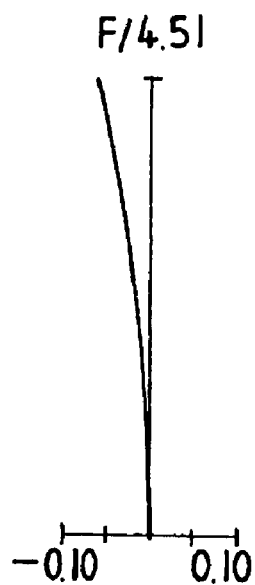
FIGS. 52A-52C show the spherical aberration, astigmatism, and distortion, respectively, of Embodiment 25 of the present invention when focused at the far point on the object side.
Figure 52B:
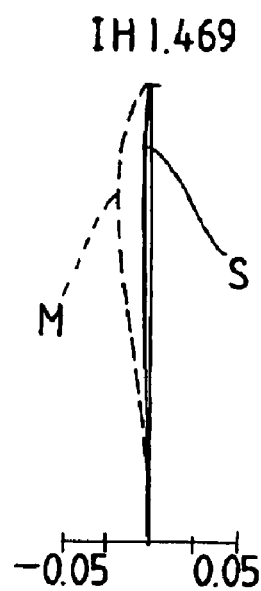
Figure 52C:
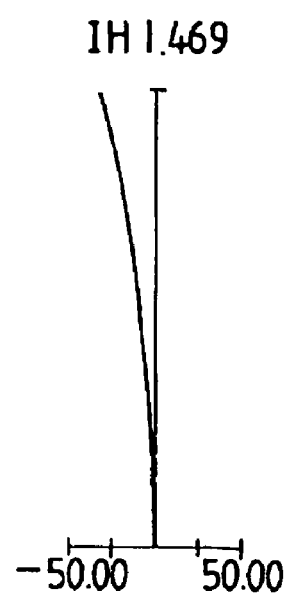
Figure 52D:
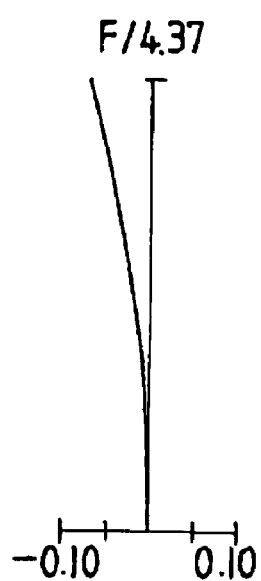
FIGS. 52D-52F show the spherical aberration, astigmatism, and distortion, respectively, of Embodiment 25 of the present invention when focused at the near point on the object side.
Figure 52E:
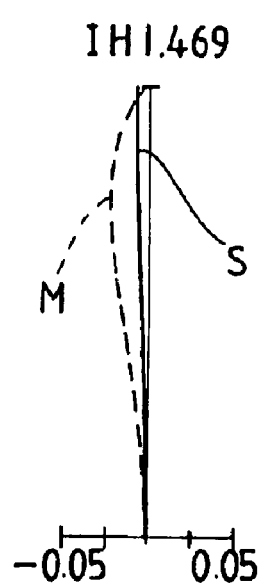
Figure 52F:
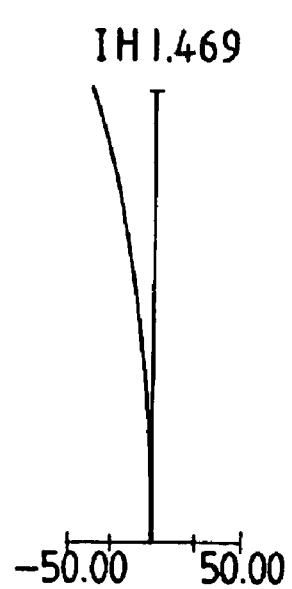

FIGS. 52A-52C show the spherical aberration, astigmatism, and distortion, respectively, of Embodiment 25 of the present invention when focused at the far point on the object side, and FIGS. 52D-52F show the spherical aberration, astigmatism, and distortion, respectively, of Embodiment 25 of the present invention when focused at the near point on the object side. As shown in FIGS. 52A-52C and FIGS. 52D-52F, in Embodiment 25 these aberrations are favorably corrected.

EMBODIMENT 26

Figure 26:
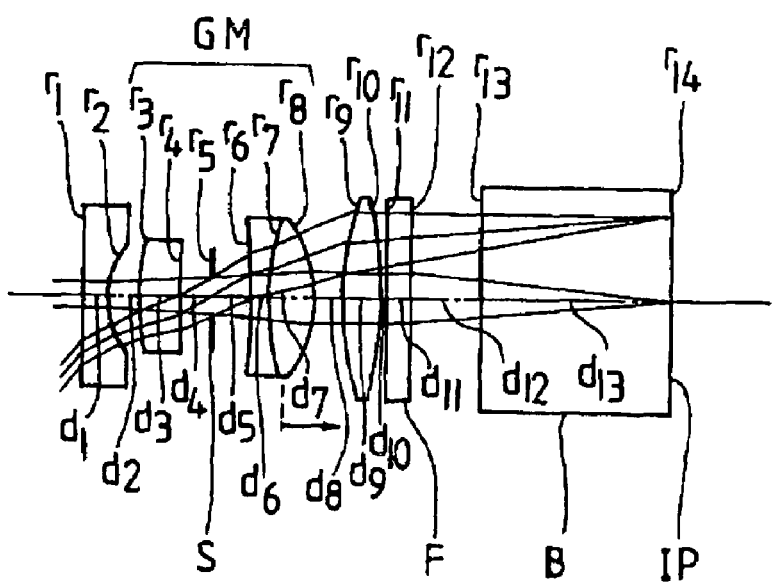
FIG. 26 is a cross-sectional view of Embodiment 26 of the present invention focused at the far point on the object side.

FIG. 26 shows a cross-sectional view of the objective optical system for an endoscope of Embodiment 26 of the present invention. Table 26 below lists the various data explained above for Embodiment 26.

TABLE 26

| Far point focused state | | | |
|---|---|---|---|
| WD = 46 | $f_{TF} = 1.939$ | $F_{NO} = 4.50$ | $2\omega = 98.6°$ |
| | Near point focused state | | |
| WD = 23 | $f_{TN} = 1.858$ | $F_{NO} = 4.34$ | $2\omega = 103.3°$ |
| $r_1 = \infty$ | $d_1 = 0.5000$ | $n_1 = 1.76820$ | $v_1 = 71.79$ |
| $r_2 = 1.4602$ | $d_2 = 0.5500$ | | |
| $r_3 = 3.9082$ | $d_3 = 0.8000$ | $n_2 = 1.92286$ | $v_2 = 18.90$ |
| $r_4 = 9.8536$ | $d_4 = 0.6318$ | | |
| $r_5 = \infty$ (stop) | $d_5 = 0.7290$ | | |
| $r_6 = -9.6808$ | $d_6 = 0.3000$ | $n_3 = 1.92286$ | $v_3 = 18.90$ |
| $r_7 = 4.2583$ | $d_7 = 0.8500$ | $n_4 = 1.72916$ | $v_4 = 54.68$ |
| $r_8 = -2.3985$ | $d_8 = 0.5502$ | | |
| $r_9 = 5.5309$ | $d_9 = 0.6906$ | $n_5 = 1.72916$ | $v_5 = 54.68$ |
| $r_{10} = -9.4912$ | $d_{10} = 0.1000$ | | |
| $r_{11} = \infty$ | $d_{11} = 0.4500$ | $n_6 = 1.51800$ | $v_6 = 75.00$ |
| $r_{12} = \infty$ | $d_{12} = 1.2697$ | | |

TABLE 26-continued

| | | | |
|---|---|---|---|
| $r_{13} = \infty$ | $d_{13} = 3.6000$ | $n_7 = 1.48749$ | $v_7 = 70.23$ |
| $r_{14} = \infty$ (image plane) | | | |

| $|f_{UM}/f_{TF}| = 2.741$ | $f_{U1}/f_{TF} = -0.980$ | $f_{TN}/f_{TF} = 0.958$ |
|---|---|---|
| $f_{U1} = -1.901$ | $f_{U1}/f_{TF} = -0.98$ | |
| $f_{U2} = 6.593$ | $f_{U2}/f_{TF} = 3.40$ | |
| $f_{U3} = 5.314$ | $f_{U3}/f_{TF} = 2.74$ | |
| $f_{UR} = 4.887$ | $f_{UR}/f_{TF} = 2.52$ | |
| $|f_U (GM, GR)|_{min} = 2.52$ | $|R (GM, GR)|_{min} = 1.24$ | |

As shown in FIG. 26, Embodiment 26 is an optical system that is similar to Embodiment 25, but in Embodiment 26 the third lens component that moves for focusing is composed of a biconcave lens element cemented to a biconvex lens element while, on the other hand, the last or rear lens component that forms the rear lens group is a single lens element. Thus, Embodiment 26 is an example of an optical system according to the fourth mode of construction of the present invention described above.

Embodiment 26 of the present invention satisfies Conditions (1) through (7) above. The focal lengths $f_U(GM,GR)$ of the lens components in the middle lens group and rear lens group and the radii of curvature R(GM,GR) of the lens surfaces of the lens components in the middle lens group and rear lens group also satisfy the applicable conditions and design criteria specified for them.

Figure 53A:
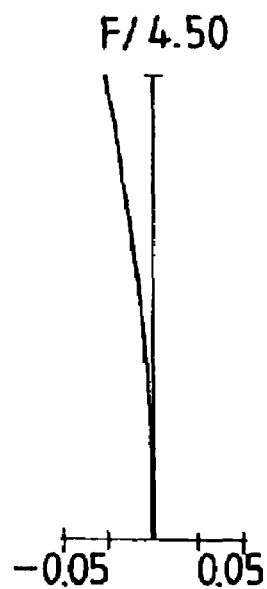
FIGS. 53A-53C show the spherical aberration, astigmatism, and distortion, respectively, of Embodiment 26 of the present invention when focused at the far point on the object side.
Figure 53B:
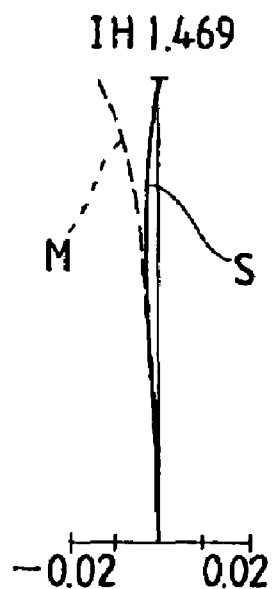
Figure 53C:
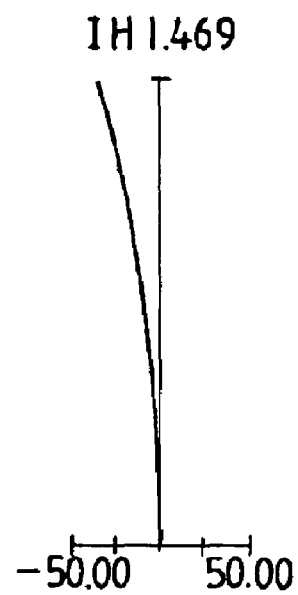
Figure 53D:
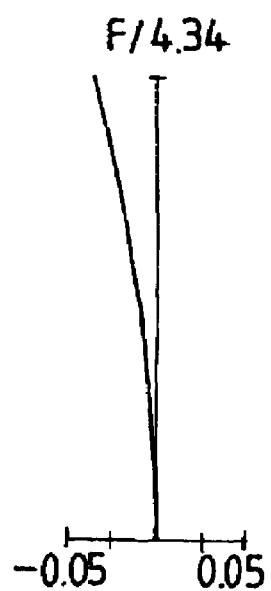
FIGS. 53D-53F show the spherical aberration, astigmatism, and distortion, respectively, of Embodiment 26 of the present invention when focused at the near point on the object side.
Figure 53E:
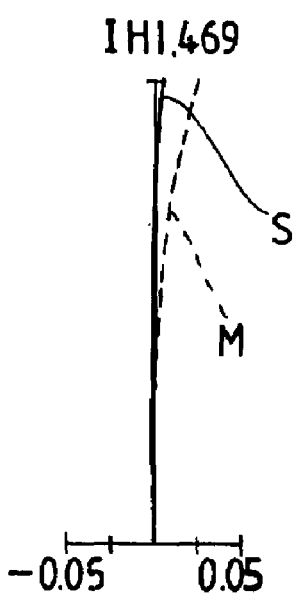
Figure 53F:
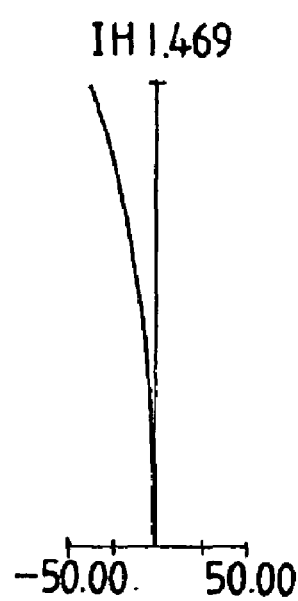

FIGS. 53A-53C show the spherical aberration, astigmatism, and distortion, respectively, of Embodiment 26 of the present invention when focused at the far point on the object side, and FIGS. 53D-53F show the spherical aberration, astigmatism, and distortion, respectively, of Embodiment 26 of the present invention when focused at the near point on the object side. As shown in FIGS. 53A-53C and FIGS. 53D-53F, in Embodiment 26 these aberrations are favorably corrected.

EMBODIMENT 27

Figure 27:
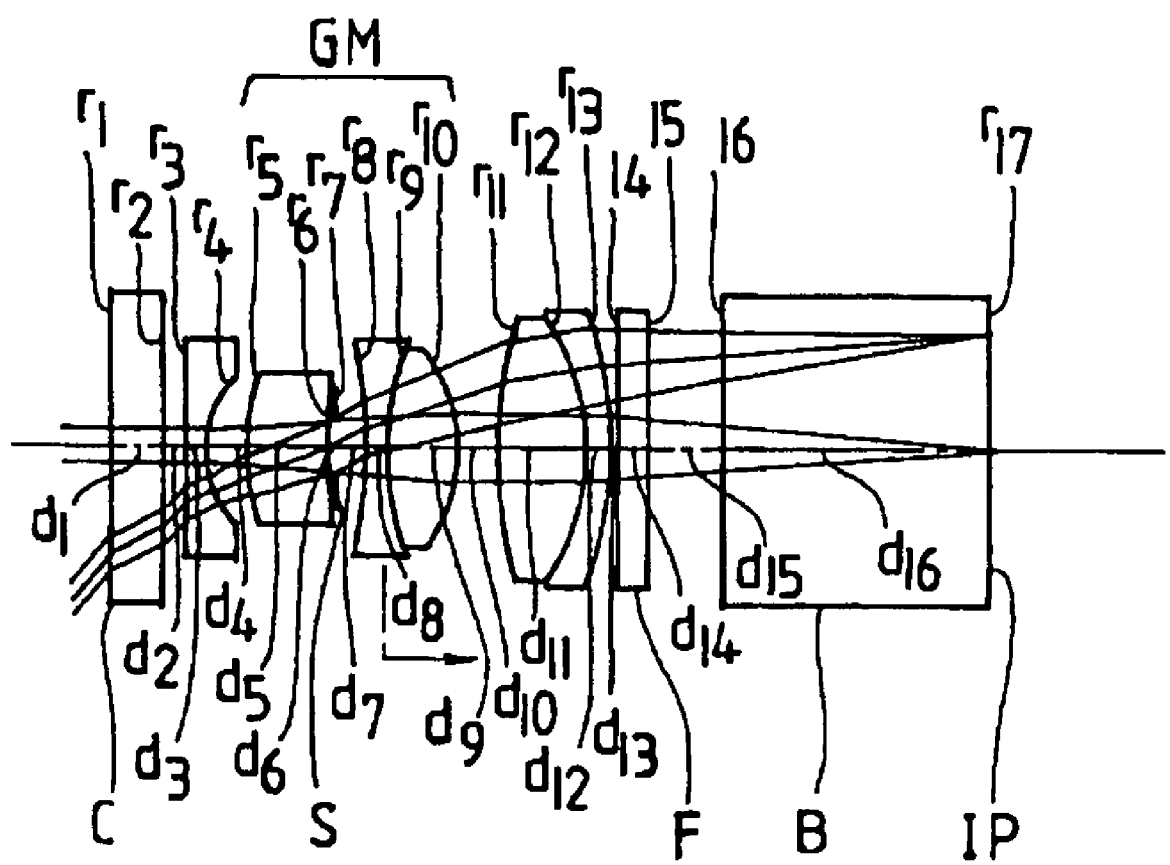
FIG. 27 is a cross-sectional view of Embodiment 27 of the present invention focused at the far point on the object side.

FIG. 27 shows a cross-sectional view of the objective optical system for an endoscope of Embodiment 27 of the present invention. Table 27 below lists the various data explained above for Embodiment 27.

TABLE 27

| Far point focused state | | | |
|---|---|---|---|
| WD = 46 | $f_{TF} = 1.931$ | $F_{NO} = 4.45$ | $2\omega = 98.6°$ |
| Near point focused state | | | |
| WD = 23 | $f_{TN} = 1.863$ | $F_{NO} = 4.32$ | $2\omega = 102.5°$ |
| $r_1 = \infty$ | $d_1 = 0.7000$ | $n_1 = 1.76820$ | $v_1 = 71.79$ |
| $r_2 = \infty$ | $d_2 = 0.2900$ | | |
| $r_3 = \infty$ | $d_3 = 0.3000$ | $n_2 = 1.88300$ | $v_2 = 40.76$ |
| $r_4 = 1.3698$ | $d_4 = 0.5500$ | | |
| $r_5 = 2.7509$ | $d_5 = 1.0923$ | $n_3 = 1.92286$ | $v_3 = 18.90$ |
| $r_6 = 6.0400$ | $d_6 = 0.0913$ | | |
| $r_7 = \infty$ (stop) | $d_7 = 0.4068$ | | |
| $r_8 = -5.9929$ | $d_8 = 0.3000$ | $n_4 = 1.88300$ | $v_4 = 40.76$ |
| $r_9 = 3.8118$ | $d_9 = 0.9500$ | $n_5 = 1.72916$ | $v_5 = 54.68$ |
| $r_{10} = -2.0854$ | $d_{10} = 0.5046$ | | |
| $r_{11} = 5.7672$ | $d_{11} = 1.2000$ | $n_6 = 1.72916$ | $v_6 = 54.68$ |
| $r_{12} = -2.7668$ | $d_{12} = 0.3000$ | $n_7 = 1.92286$ | $v_7 = 18.90$ |
| $r_{13} = -5.0472$ | $d_{13} = 0.1000$ | | |
| $r_{14} = \infty$ | $d_{14} = 0.4500$ | $n_8 = 1.51800$ | $v_8 = 75.00$ |
| $r_{15} = \infty$ | $d_{15} = 0.9776$ | | |
| $r_{16} = \infty$ | $d_{16} = 3.6000$ | $n_9 = 1.48749$ | $v_9 = 70.23$ |
| $r_{17} = \infty$ (image plane) | | | |

TABLE 27-continued

| $|f_{UM}/f_{TF}| = 2.521$ | $f_{U1}/f_{TF} = -0.803$ | $f_{TN}/f_{TF} = 0.965$ |
|---|---|---|
| $f_{U1} = -1.551$ | $f_{U1}/f_{TF} = -0.80$ | |
| $f_{U2} = 4.721$ | $f_{U2}/f_{TF} = 2.44$ | |
| $f_{U3} = 4.868$ | $f_{U3}/f_{TF} = 2.52$ | |
| $f_{UR} = 4.394$ | $f_{UR}/f_{TF} = 2.28$ | |
| $|f_U (GM, GR)|_{min} = 2.28$ | $|R (GM, GR)|_{min} = 1.08$ | |
| $n(GR_p) = n_6 = 1.72916$ | $n(GR_n) = n_7 = 1.92286$ | |
| $v(GR_p) = v_6 = 54.68$ | $v(GR_n) = v_7 = 18.90$ | |

As shown in FIG. 27, Embodiment 27 is an optical system that is similar to Embodiment 25 shown in FIG. 25, but with the third lens component in Embodiment 27 being a cemented lens component. Thus, Embodiment 27 is an example of an optical system according to the fourth mode of construction of the present invention described above.

Embodiment 27 of the present invention satisfies Conditions (1) through (7) above. The focal lengths $f_U(GM,GR)$ of the lens components in the middle lens group and rear lens group and the radii of curvature R(GM,GR) of the lens surfaces of the lens components in the middle lens group and rear lens group also satisfy the applicable conditions and design criteria specified for them. As described above, the refractive indices $n(GR_p)$ and $n(GR_n)$ and the Abbe numbers $v(GR_p)$ and $v(GR_n)$ of the lens materials of the cemented lens component that is the last lens component also satisfy the applicable conditions and design criteria of the present invention.

Figure 54A:
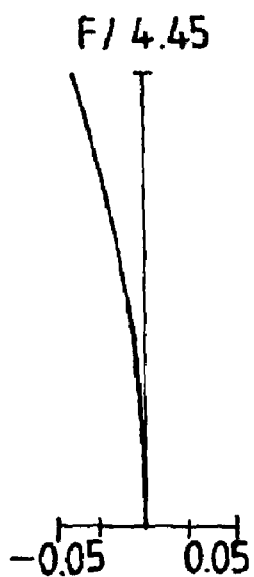
FIGS. 54A-54C show the spherical aberration, astigmatism, and distortion, respectively, of Embodiment 27 of the present invention when focused at the far point on the object side.
Figure 54B:
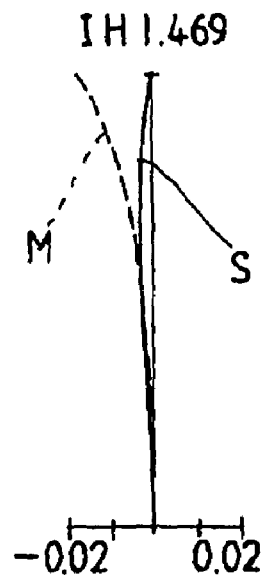
Figure 54C:
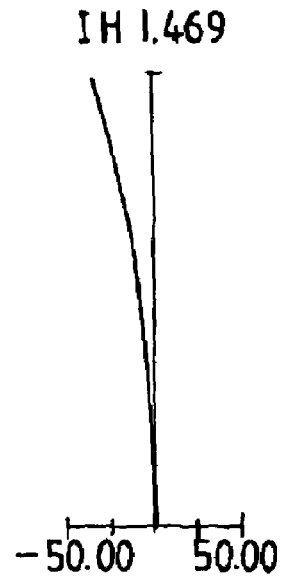
Figure 54D:
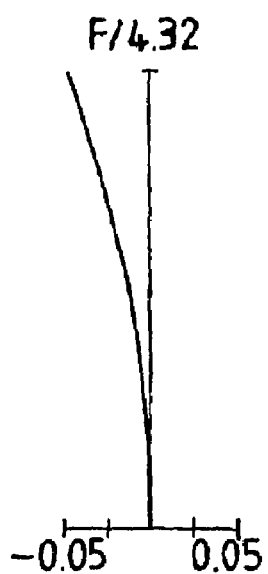
FIGS. 54D-54F show the spherical aberration, astigmatism, and distortion, respectively, of Embodiment 27 of the present invention when focused at the near point on the object side.
Figure 54E:
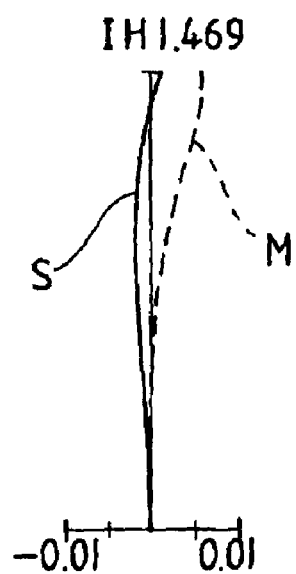
Figure 54F:
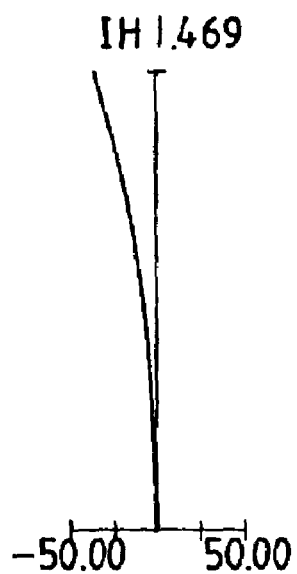

FIGS. 54A-54C show the spherical aberration, astigmatism, and distortion, respectively, of Embodiment 27 of the present invention when focused at the far point on the object side, and FIGS. 54D-54F show the spherical aberration, astigmatism, and distortion, respectively, of Embodiment 27 of the present invention when focused at the near point on the object side. As shown in FIGS. 54A-54C and FIGS. 54D-54F, in Embodiment 27 these aberrations are favorably corrected.

All of Embodiments 1-27 above may be used with image pickup elements having a pixel pitch of 2.1 μm arranged on the image plane. The maximum image height is 1.469 mm, and the f-number is about 4.5. When a cover glass C is arranged on the object-most side it is made of sapphire. When a cover glass is not used, sapphire is used as the material for the object-most side lens element. An absorption type infrared cutoff filter F is arranged in the optical system, and a prism for horizontally placing the image pickup elements and/or a glass block B representing a multiplate prism unit are arranged on the image-most side.

The objective optical system for an endoscope of the present invention is suited to a high-precision endoscope having a focusing function performed by movement of a lens component, and it is an optical system in which the lens component that moves for focusing is small, aberrations are favorably corrected and fluctuate little with focusing movement of the focusing lens component.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An objective optical system for an endoscope having an object side and an image side and comprising, arranged along an optical axis in order from the object side, as follows:

a front lens group having negative refractive power and consisting of a first lens component;

a middle lens group having positive refractive power and including at least two lens components, each of said at least two lens components having positive refractive power; and a rear lens group having positive refractive power and consisting of one lens component; wherein only one lens component of said middle lens group moves in the direction of the optical axis during focusing;

a stop for controlling image brightness is positioned within said middle lens group or between said front lens group and said middle lens group; and the following conditions are satisfied:

$$2<|f_{UM}/f_{TF}|<10$$

$$-1.25<f_{U1}/f_{TF}<-0.6$$

where $f_{UM}$ is the focal length of said only one lens component;

$f_{TF}$ is the focal length of the entire objective optical system for an endoscope focused at the far point on the object side; and $f_{U1}$ is the focal length of said first lens component.

2. The objective optical system for an endoscope of claim 1, wherein said middle lens group is formed of at least three lens components.

3. The objective optical system for an endoscope of claim 2, wherein said middle lens group consists of, arranged in the following order from the object side, a second lens component having positive refractive power, a third lens component, and a fourth lens component having positive refractive power.

4. The objective optical system for an endoscope of claim 2, wherein said middle lens group consists of, arranged in the following order from the object side, a second lens component having positive refractive power, a third lens component, a fourth lens component having positive refractive power, and a fifth lens component having positive refractive power.

5. The objective optical system for an endoscope of claim 1, wherein said middle lens group consists of, arranged in the following order from the object side, a second lens component having positive refractive power, said stop, and a third lens component having positive refractive power.

6. The objective optical system for an endoscope of claim 1, wherein the following condition is satisfied:

$$0.85<f_{TN}/f_{TF}<1.15$$

where $f_{TN}$ is the focal length of the entire objective optical system for an endoscope focused at the near point on the object side.

7. The objective optical system for an endoscope of claim 1, wherein the following condition is satisfied:

$$0.85<f_{TN}/f_{TF}<1$$

where $f_{TN}$ is the focal length of the entire objective optical system for an endoscope focused at the near point on the object side.

8. The objective optical system for an endoscope of claim 1, wherein the following conditions are satisfied:

$$n_{U1}>1.7$$

$$v_{U1}>38$$

where $n_{U1}$ is the refractive index at the d-line of said first lens component; and $v_{U1}$ is the Abbe number at the d-line of said first lens component.

9. The objective optical system for an endoscope of claim 1, wherein said first lens component consists of a plano-concave lens element formed of sapphire material.

10. The objective optical system for an endoscope of claim 1, wherein the following condition is satisfied:

$$|f_U(GM,GR)|\geq 1.4 f_{TF}$$

where $f_U(GM,GR)$ is the focal length of each of the lens components of each of said middle lens group and of said rear lens group.

11. The objective optical system for an endoscope of claim 1, wherein the following condition is satisfied:

$$|R(GM,GR)|>0.8 f_{TF}$$

where $R(GM,GR)$ is the radius of curvature of each lens surface of each lens element of each of the lens components of each of said middle lens group and of said rear lens group.

12. The objective optical system for an endoscope of claim 1, wherein said rear lens group consists of a cemented lens component formed of a lens element having negative refractive power and a lens element having positive refractive power that satisfy the following conditions:

$$n(GR_n)>1.82$$

$$v(GR_n)<26$$

$$n(GR_p)<1.78$$

$$v(GR_p)>49$$

where $n(GR_n)$ is the refractive index at the d-line of said lens element having negative refractive power;

$v(GR_n)$ is the Abbe number at the d-line of said lens element having negative refractive power;

$n(GR_p)$ is the refractive index at the d-line of said lens element having positive refractive power; and $v(GR_p)$ is the Abbe number at the d-line of said lens element having positive refractive power.

13. The objective optical system for an endoscope of claim 1, wherein the following condition is satisfied:

$$2<f_{UR}/f_{TF}<12$$

where $f_{UR}$ is the focal length of the lens component of said rear lens group.

14. The objective optical system for an endoscope of claim 1, wherein each of at least two lens components consists of a lens element having negative refractive power that is cemented to a lens element having positive refractive power and having a refractive index that is at least 0.1 less than the refractive index of said lens element having negative refractive power.

15. The objective optical system for an endoscope of claim 1, wherein said only one lens component consists of a single lens element having positive refractive power and a refractive index of 1.75 or less.

16. The objective optical system for an endoscope of claim 1, wherein said only one lens component has positive refractive power and consists of a lens element having negative refractive power and a lens element having positive refractive power, with the lens element having positive refractive power having a refractive index that is at least 0.1 less than the refractive index of said lens element having negative refractive power.

17. The objective optical system for an endoscope of claim 1, wherein said only one lens component is adjacent said stop.

18. The objective optical system for an endoscope of claim 1, wherein the one lens component of the middle lens group that moves in the direction of the optical axis during focusing is other than the object-side lens component or the image-side lens component of said middle lens group.

19. The objective optical system for an endoscope of claim 1, wherein each of the object-side lens component of said middle lens group and the image-side lens component of said middle lens group has positive refractive power.

* * * * *